US011472866B2

(12) United States Patent
Khan et al.

(10) Patent No.: US 11,472,866 B2
(45) Date of Patent: Oct. 18, 2022

(54) ADENO-ASSOCIATED VIRUS ANTIBODIES, FRAGMENTS THEREOF AND ENCODING POLYNUCLEOTIDES

(71) Applicant: Sarepta Therapeutics, Inc., Cambridge, MA (US)

(72) Inventors: Sohrab Khan, Cambridge, MA (US); Danielle Griffin, Cambridge, MA (US); Louise Rodino-Klapac, Cambridge, MA (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/478,645

(22) Filed: Sep. 17, 2021

(65) Prior Publication Data

US 2022/0033478 A1 Feb. 3, 2022

Related U.S. Application Data

(63) Continuation of application No. 17/348,356, filed on Jun. 15, 2021.

(60) Provisional application No. 63/038,957, filed on Jun. 15, 2020.

(51) Int. Cl.
*C07K 16/08* (2006.01)
*A01K 67/027* (2006.01)
*G01N 33/543* (2006.01)

(52) U.S. Cl.
CPC ............ *C07K 16/08* (2013.01); *A01K 67/027* (2013.01); *G01N 33/54306* (2013.01); *A01K 2217/05* (2013.01)

(58) Field of Classification Search
CPC .. C07K 16/08; A01K 67/027; A01K 2217/05; G01N 33/54306
See application file for complete search history.

(56) References Cited

U.S. PATENT DOCUMENTS

| | | | |
|---|---|---|---|
| 4,816,567 A | 3/1989 | Cabilly et al. | |
| 5,225,539 A | 7/1993 | Winter | |
| 5,530,101 A | 6/1996 | Queen et al. | |
| 5,585,089 A | 12/1996 | Queen et al. | |
| 5,693,762 A | 12/1997 | Queen et al. | |
| 6,180,370 B1 | 1/2001 | Queen et al. | |
| 2021/0388064 A1 | 12/2021 | Khan et al. | |

FOREIGN PATENT DOCUMENTS

| | | |
|---|---|---|
| WO | WO-2013123503 A1 | 8/2013 |
| WO | WO-2016176212 A1 | 11/2016 |
| WO | WO-2021257497 A1 | 12/2021 |

OTHER PUBLICATIONS

Bird, R. E., et al., "Single-chain antigen-binding proteins," *Science* 242(4877):423-426, Association for the Advancement of Science, United States (Oct. 1988).

Blacklow, N. R., et al., "Serologic evidence for human infection with adenovirus-associated viruses," *J Natl Cancer Inst* 40(2):319-327, Oxford University Press, United Kingdom (Febmary 1968).

Boutin, S., et al., "Prevalence of serum IgG and neutralizing factors against adeno-associated virus (AAV) types 1, 2, 5, 6, 8, and 9 in the healthy population: implications for gene therapy using AAV vectors," *Hum Gene Ther* 21(6):704-712, Mary Ann Liebert Inc., United States (Jun. 2010).

Brennan, M., et al., "Preparation of bispecific antibodies by chemical recombination of monoclonal immunoglobulin G1 fragments," *Science* 229(4708):81-83, American Association for the Advancement of Science, United States (Jul. 1985).

Carter, P., et al., "High level *Escherichia coli* expression and production of a bivalent humanized antibody fragment," *Biotechnology (N Y)* 10(2):163-167, Wiley-Blackwell, United States (Feb. 1992).

Chirmule, N., et al., "Immune responses to adenovirus and adeno-associated virus in humans," *Gene Ther* 6(9):1574-1583, Nature Publishing Group, United Kingdom (Sep. 1999).

Chothia, C., and Lesk, A. M., "Canonical structures for the hypervariable regions of immunoglobulins," *J Mol Biol* 196(4):901-917, Elsevier Science, United States (Aug. 1987).

Erles, K., et al., "Update on the prevalence of serum antibodies (IgG and IgM) to adeno-associated virus (AAV)," *J Med Virol* 59(3):406-411, Wiley, United States (Nov. 1999).

Harlow, E., and Lane, D., eds., "Chapter 14: Immunoassays," pp. 553-612, Cold Spring Harbor Laboratory, United States (1988).

Huston, J. S., et al., "Protein engineering of antibody binding sites: recovery of specific activity in an anti-digoxin single-chain Fv analogue produced in *Escherichia coli*," *Proc Natl Acad Sci USA* 85(16):5879-5883, National Academy of Sciences, United States (Aug. 1988).

Kabat, E. A., et al., "Unusual distributions of amino acids in complementarity-determining (hypervariable) segments of heavy and light chains of immunoglobulins and their possible roles in specificity of antibody-combining sites," *J Biol Chem* 252(19):6609-6616, Elsevier, Netherlands (Oct. 1977).

Kabat et al., "Sequences of proteins of immunological interest," U.S. Dept. of Health and Human Services, United States (1991).

Maccallum, R. M., et al., "Antibody-antigen interactions: contact analysis and binding site topography," *J Mol Biol* 262(5):732-745, Academic Press, United Kingdom (Oct. 1996).

(Continued)

*Primary Examiner* — Robert S Landsman
(74) *Attorney, Agent, or Firm* — Sterne, Kessler, Goldstein & Fox P.L.L.C.

(57) ABSTRACT

The present disclosure relates to an isolated anti-AAV (adeno-associated virus) antibody or an antigen-binding fragment thereof capable of specifically binding an epitope of AAVrh74 capsid protein and uses thereof.

19 Claims, 18 Drawing Sheets

Specification includes a Sequence Listing.

(56) References Cited

OTHER PUBLICATIONS

Mayor, H. D., et al., "Antibodies to adeno-associated satellite virus and herpes simplex in sera from cancer patients and normal adults," *Am J Obstet Gynecol* 126(1):100-104, Elsevier, Netherlands (Sep. 1976).

Mccafferty, J., et al., "Phage antibodies: filamentous phage displaying antibody variable domains," *Nature* 348(6301):552-554, Nature Publishing Group, United Kingdom (Dec. 1990).

Morimoto, K., and Inouye, K., "Single-step purification of F(ab')2 fragments of mouse monoclonal antibodies (immunoglobulins G1) by hydrophobic interaction high performance liquid chromatography using TSKgel Phenyl-5PW," *J Biochem Biophys Methods* 24(1-2):107-117, Elsevier, Netherlands (Mar. 1992).

Morrison, S. L., "Transfectomas provide novel chimeric antibodies," *Science* 229(4719):1202-1207, American Association for the Advancement of Science, United States (Sep. 1985).

Parks, W. P., et al., "Seroepidemiological and ecological studies of the adenovirus-associated satellite viruses," *Infect Immun* 2(6):716-722, American Association for Microbiology, United States (Dec. 1970).

International Search Report and Written Opinion for International Application No. PCT/US2021/037314, European Patent Office, Netherlands, dated Sep. 29, 2021, 10 pages.

**Antibody: Ms-Hu IgG chimera 10D2
Antigen: AAVrh74**

**Antibody: Ms-Hu IgG chimera 10D2
Antigen: AAV8**

SEQUENCE LISTING

```
<160> NUMBER OF SEQ ID NOS: 63

<210> SEQ ID NO 1
<211> LENGTH: 142
<212> TYPE: PRT
<213> ORGANISM: Artificial Sequence
<220> FEATURE:
<223> OTHER INFORMATION: 10D2-1 Heavy chain variable region

<400> SEQUENCE: 1
```

```
Met Asp Trp Leu Trp Asn Leu Leu Phe Leu Met Ala Ala Ala Gln Ser
1               5                   10                  15

Ala Gln Thr Gln Ile Gln Leu Val Gln Ser Gly Pro Glu Leu Arg Lys
            20                  25                  30

Pro Gly Glu Thr Val Lys Ile Ser Cys Lys Ala Ser Gly Tyr Ser Phe
        35                  40                  45

Thr Asn Tyr Gly Met Asn Trp Val Lys Gln Thr Pro Gly Lys Asp Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Ala Ser Ala Asn
                85                  90                  95

Thr Ala Tyr Leu Gln Ile Asn Asp Leu Lys Asn Glu Asp Met Ala Thr
            100                 105                 110

Tyr Phe Cys Ala Arg Gly Val Ala His Tyr Ser Asp Ser Arg Phe Ala
        115                 120                 125

Phe Asp Tyr Trp Gly Gln Gly Thr Thr Leu Thr Val Pro Ser
    130                 135                 140

<210> SEQ ID NO 2
<211> LENGTH: 128
<212> TYPE: PRT
<213> ORGANISM: Artificial Sequence
<220> FEATURE:
<223> OTHER INFORMATION: 10D2-1 Light chain variable region

<400> SEQUENCE: 2

Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Val Ser
        35                  40                  45

Ser Ser Val Ser Tyr Met His Trp Phe Gln Gln Lys Pro Gly Thr Ser
    50                  55                  60

Pro Lys Leu Trp Ile Tyr Tyr Thr Ser Asn Leu Ala Ser Gly Val Pro
65                  70                  75                  80

Gly Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Ser Ser Tyr Pro Phe Thr Phe Gly Ser Gly Thr Lys Leu Glu Ile Lys
        115                 120                 125

<210> SEQ ID NO 3
<211> LENGTH: 426
<212> TYPE: DNA
<213> ORGANISM: Artificial Sequence
<220> FEATURE:
<223> OTHER INFORMATION: 10D2-1 Heavy chain variable region full
      nucleotide

<400> SEQUENCE: 3
atggattggc tgtggaactt gctattcctg atggcagctg cccaaagtgc ccaaacacag      60
atccagttgg tgcagtctgg acctgagttg aggaagcctg gagagacagt caagatctcc     120
tgcaaggctt ctggatattc cttcacaaac tatggaatga actgggtgaa gcagactcca     180
ggaaaggatt taaagtggat gggctggata aacacctaca ctggagagcc aacatatgct     240
```

```
gatgacttca agggacggtt cgccttctct ctggaagcct ctgccaacac tgcctatttg    300
cagatcaacg acctcaaaaa tgaggacatg gctacatatt tctgtgcaag gggtgtggct    360
cattactccg atagtaggtt cgcctttgac tactggggcc aaggaaccac tctcacagtc    420
ccctcc                                                               426
```

<210> SEQ ID NO 4
<211> LENGTH: 384
<212> TYPE: DNA
<213> ORGANISM: Artificial Sequence
<220> FEATURE:
<223> OTHER INFORMATION: 10D2-1 Light chain variable region full
      nucleotide sequence

<400> SEQUENCE: 4

```
atgcattttc aagtgcagat tttcagcttc ctgctaatca gtgcctcagt cataatgtcc     60
agaggacaaa ttgttctcac ccagtcacca gcaatcatgt ctgcatctcc aggggagaag    120
gtcaccataa cctgcagtgt cagctcaagt gttagttaca tgcactggtt ccagcagaag    180
ccaggcactt ctcccaaact ctggatttat tacacatcca acctggcttc tggagtccct    240
ggtcgcttca gtggcagtgg atctgggacc tcttactccc tcacaatcag ccgaatggag    300
gctgaagatg ctgccactta ttactgccag caaaggagta gttacccatt cacgttcggc    360
tcggggacaa agttggaaat aaaa                                           384
```

<210> SEQ ID NO 5
<211> LENGTH: 140
<212> TYPE: PRT
<213> ORGANISM: Artificial Sequence
<220> FEATURE:
<223> OTHER INFORMATION: 28D8-1 Heavy chain variable region full amino
      acid sequence

<400> SEQUENCE: 5

Met Asp Trp Leu Trp Asn Leu Leu Phe Leu Met Ala Ala Ala Gln Ser
1               5                   10                  15

Ala Gln Thr Gln Ile Gln Leu Val Gln Ser Gly Pro Glu Leu Lys Lys
            20                  25                  30

Pro Gly Glu Thr Val Lys Ile Ser Cys Lys Ala Ala Gly Tyr Thr Phe
        35                  40                  45

Thr Asp Tyr Gly Met Asn Trp Val Lys Gln Ala Pro Gly Glu Gly Leu
    50                  55                  60

Lys Trp Met Gly Trp Ile Asn Thr Asn Thr Gly Glu Pro Thr Tyr Gly
65                  70                  75                  80

Asp Asp Phe Lys Gly Arg Phe Ala Phe Ser Leu Glu Ala Ser Ala Ser
                85                  90                  95

Thr Ala His Leu Gln Ile Asn Asn Leu Lys Asn Asp Asp Met Ala Ile
            100                 105                 110

Tyr Phe Cys Ala Arg Gly Asn Ala His Pro Gly Gly Ser Ala Phe Val
        115                 120                 125

Tyr Trp Gly Gln Gly Thr Leu Val Thr Val Ser Ala
    130                 135                 140

<210> SEQ ID NO 6
<211> LENGTH: 128
<212> TYPE: PRT
<213> ORGANISM: Artificial Sequence
<220> FEATURE:
<223> OTHER INFORMATION: 28D8-1 Light chain variable region full amino -continued acid sequence

<400> SEQUENCE: 6

Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Ser Val Thr Ile Thr Cys Ser Ala Ser
        35                  40                  45

Ser Gly Val Thr Tyr Met His Trp Phe Gln Gln Lys Pro Gly Thr Ser
    50                  55                  60

Pro Lys Asn Trp Ile Tyr Arg Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Ser Ser Tyr Pro Phe Thr Phe Gly Ser Gly Thr Lys Leu Glu Ile Lys
        115                 120                 125

<210> SEQ ID NO 7
<211> LENGTH: 420
<212> TYPE: DNA
<213> ORGANISM: Artificial Sequence
<220> FEATURE:
<223> OTHER INFORMATION: 28D8-1 Heavy chain variable region full
      nucleotide sequence

<400> SEQUENCE: 7
atggattggc tgtggaactt gctattcctg atggcagcag cccaaagcgc ccaaacacag      60
atccagttgg tgcagtctgg acctgagctg aagaagcctg gagagacagt caagatctcc    120
tgcaaggctg ctgggtatac cttcacagac tatggaatga actgggtgaa gcaggctcca    180
ggagagggtt taaagtggat gggctggata acaccaata ctggagagcc aacatatggt     240
gatgacttca agggacggtt tgccttctct ttggaagcct ctgccagcac tgcccatttg    300
cagatcaaca acctcaaaaa tgacgacatg gcaatatatt tctgtgcaag agggaacgct    360 catccccggtg gtagtgcgtt tgtttactgg ggccaaggga ctctggtcac tgtctctgca    420

<210> SEQ ID NO 8
<211> LENGTH: 384
<212> TYPE: DNA
<213> ORGANISM: Artificial Sequence
<220> FEATURE:
<223> OTHER INFORMATION: 28D8-1 Light chain variable region full
      nucleotide sequence

<400> SEQUENCE: 8
atgcattttc aagtgcagat tttcagcttc ctgctaatca gtgcctcagt cataatgtcc      60
agaggacaaa ttgttctcac ccagtctcca gcaatcatgt ctgcatctcc aggggagagt    120
gtcaccataa cctgcagtgc cagctcaggt gtcacttaca tgcactggtt ccagcagaag    180
ccaggcactt ctcccaaaaa ctggatttat agaacatcca atctggcttc tggagtccct    240
gctcgcttca gtggcagtgg atctgggacc tcttactctc tcacaatcag ccgaatggag    300
gctgaagatg ctgccactta ttactgccag caaaggagta gttacccatt cacattcggc    360
tcggggacaa agttggaaat aaaa                                            384

```
<210> SEQ ID NO 9
<211> LENGTH: 121
<212> TYPE: PRT
<213> ORGANISM: Artificial Sequence
<220> FEATURE:
<223> OTHER INFORMATION: 6E10B5 Heavy chain variable region full amino
      acid sequence

<400> SEQUENCE: 9

Gln Val Lys Leu Gln Glu Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Pro Gly Glu Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Lys Thr Ser Ala Ser Thr Ala Tyr
65                  70                  75                  80

Leu Gln Ile Asn Asn Leu Lys Asn Glu Gly Thr Thr Thr Tyr Phe Cys
                85                  90                  95

Ala Arg Gly Val Asp Ser Ser Gly Tyr Gly Ala Phe Ala Tyr Trp Gly
            100                 105                 110

Gln Gly Thr Leu Val Thr Val Ser Ala
        115                 120

<210> SEQ ID NO 10
<211> LENGTH: 107
<212> TYPE: PRT
<213> ORGANISM: Artificial Sequence
<220> FEATURE:
<223> OTHER INFORMATION: 6E10B5 Light chain variable region full amino
      acid sequence

<400> SEQUENCE: 10

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Phe Tyr Pro Phe Thr
                85                  90                  95

Phe Gly Ser Gly Thr Lys Leu Glu Ile Lys Arg
            100                 105

<210> SEQ ID NO 11
<211> LENGTH: 363
<212> TYPE: DNA
<213> ORGANISM: Artificial Sequence
<220> FEATURE:
<223> OTHER INFORMATION: 6E10B5 Heavy chain variable region full
      nucleotide sequence

<400> SEQUENCE: 11
caagttaagc tgcaggagtc tggacctgag ctgaagaagc ctggagagac agtcaagatc     60
```

```
tcctgcaagg cttctgggta taccttcaca aagtatggaa tgaactgggt gaagcaggct    120
ccaggagagg gtttaaagtg gatgggctgg ataaacacct acactggaga gccaacatat    180
gctgatgact tcaagggacg gtttgccttc tctttgaaaa cctctgccag tactgcctat    240
ttgcagatca caaccctcaa aaatgagggc acgactacta tttctgtgc aagagggta     300 gacagctcgg gctacggcgc ctttgcttac tggggccaag ggactctggt cactgtctct    360
gca                                                                  363

<210> SEQ ID NO 12
<211> LENGTH: 321
<212> TYPE: DNA
<213> ORGANISM: Artificial Sequence
<220> FEATURE:
<223> OTHER INFORMATION: 6E10B5 Light chain variable region full
      nucleotide sequence

<400> SEQUENCE: 12
caaattgttc tcacccagtc tccagcaatc atgtctgcat ctccagggga gaaggtcacc     60
ataacctgca gtgccagctc aagtgtaagt tacatgcact ggttccagca gaagccaggc    120
acttctccca aactctggat ttatagcaca tccaacctgg cttctggagt ccctgctcgc    180
ttcagtggca gtggatctgg gacctcttac tctctcacaa tcagccgaat ggaggctgaa    240
gatgcagcca cttattactg ccagcaaagg agttttacc cattcacgtt cggctcgggg     300
acaaagttgg aaataaaacg g                                              321

<210> SEQ ID NO 13
<211> LENGTH: 123
<212> TYPE: PRT
<213> ORGANISM: Artificial Sequence
<220> FEATURE:
<223> OTHER INFORMATION: 1C4F4 Heavy chain variable region full amino
      acid sequence

<400> SEQUENCE: 13

Gln Val Lys Leu Glu Glu Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Arg Lys Val Tyr
65                  70                  75                  80

Leu Gln Ile Asn Asn Leu Lys Asn Glu Asp Met Ala Thr Tyr Phe Cys
                85                  90                  95

Ala Arg Gly Ser Tyr Tyr Tyr Asp Ser Ser Pro Ala Trp Phe Ala Tyr
            100                 105                 110

Trp Gly Gln Gly Thr Leu Val Thr Val Ser Ala
        115                 120

<210> SEQ ID NO 14
<211> LENGTH: 107
<212> TYPE: PRT
<213> ORGANISM: Artificial Sequence
<220> FEATURE:
<223> OTHER INFORMATION: 1C4F4 Heavy chain variable region full
      nucleotide sequence
```

<400> SEQUENCE: 14

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Thr Tyr Pro Phe Thr
                85                  90                  95

Phe Gly Ser Gly Thr Lys Leu Glu Ile Lys Arg
            100                 105

<210> SEQ ID NO 15
<211> LENGTH: 369
<212> TYPE: DNA
<213> ORGANISM: Artificial Sequence
<220> FEATURE:
<223> OTHER INFORMATION: 1C4F4 Heavy chain variable region full
      nucleotide sequence

<400> SEQUENCE: 15
caggtgaagc tggaggagtc tggacctgag ctgaagaagc ctggagagac agtcaagatc    60
tcctgcaagg cttctgggta taccttcaca aactatggaa tgaactgggt gaagcaggct   120
ccaggaaagg gtttaaagtg gatgggctgg ataaacacct acactggaga gccaacatat   180
gctgatgact caagggacg gtttgccttc tctttggaaa cctctgccag gaaagtctat   240
ttgcagatca caacctcaa aaatgaggac atggctacat atttctgtgc aagggggttct   300 tattactacg acagtagccc tgcctggttt gcttactggg ccaagggac tctggtcact   360 gtctctgca                                                           369

<210> SEQ ID NO 16
<211> LENGTH: 321
<212> TYPE: DNA
<213> ORGANISM: Artificial Sequence
<220> FEATURE:
<223> OTHER INFORMATION: 1C4F4 Light chain variable region full
      nucleotide sequence

<400> SEQUENCE: 16
caaattgttc tcacccagtc tccagcaatc atgtctgcat ctccagggga aaggtcacc    60 ataacctgca gtgccagttc aagtgtaagt tacatgcact ggttccagca gaagccaggc   120
acttctccca aactctggat ttatagcaca tccaacctgg cttctggagt ccctgctcgc   180
ttcagtggca gtggatctgg gacctcttac tctctcacaa tcagccgaat ggaggctgag   240
gatgctgcca cttattactg ccagcaaagg agtacttacc cattcacgtt cggctcgggg   300
acaaagttgg aaataaaacg g                                             321

<210> SEQ ID NO 17
<211> LENGTH: 122
<212> TYPE: PRT
<213> ORGANISM: Artificial Sequence
<220> FEATURE:
<223> OTHER INFORMATION: 7D4B9 Heavy chain variable region full amino
      acid sequence

<400> SEQUENCE: 17

```
Glu Val Gln Leu Gln Glu Ser Gly Ser Asp Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Tyr Glu Asp Thr Gly Thr Tyr Phe Cys
                85                  90                  95

Thr Arg Gly Thr Ser Thr Met Ile Ser Thr Phe Ala Phe Val Tyr Trp
            100                 105                 110

Gly Gln Gly Thr Leu Val Thr Val Ser Ala
        115                 120
```

<210> SEQ ID NO 18
<211> LENGTH: 107
<212> TYPE: PRT
<213> ORGANISM: Artificial Sequence
<220> FEATURE:
<223> OTHER INFORMATION: 7D4B9 Light chain variable region full amino
      acid sequence

<400> SEQUENCE: 18

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Arg Tyr Met
            20                  25                  30

His Trp Phe Gln Gln Lys Pro Gly Thr Ser Pro Lys Val Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Thr Tyr Tyr Pro Phe Thr
                85                  90                  95

Phe Gly Ser Gly Thr Lys Leu Glu Ile Lys Arg
            100                 105
```

<210> SEQ ID NO 19
<211> LENGTH: 366
<212> TYPE: DNA
<213> ORGANISM: Artificial Sequence
<220> FEATURE:
<223> OTHER INFORMATION: 7D4B9 Heavy chain variable region full
      nucleotide sequence

<400> SEQUENCE: 19

```
gaagttcagc tgcaggagtc tggatctgac ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ataaacacct acactggaga gccaacatat     180
gctgatgact tcaagggacg gtttgccttc tctttggaaa cctctgccag cactgccttt     240
ttgcaaatca acaacctcaa atatgaggac acgggtacat atttctgtac aagagggact     300
```

```
tctactatga tttcgacgtt cgcgtttgtt tactggggcc aagggactct ggtcaccgtc    360
tctgcg                                                                366
```

<210> SEQ ID NO 20
<211> LENGTH: 321
<212> TYPE: DNA
<213> ORGANISM: Artificial Sequence
<220> FEATURE:
<223> OTHER INFORMATION: 7D4B9 Light chain variable region full
      nucleotide sequence

<400> SEQUENCE: 20

```
caaattgttc tcacccagtc tccagcaatc atgtctgcat ctccagggga gaaggtcacc     60
ataacctgca gtgccagctc aagtgtacgt tacatgcact ggttccagca gaagccaggc    120
acttctccca agtctggatt tatagcaca tccaacctgg cttctggagt ccctgctcgc    180
ttcagtggca gtggatctgg gacctcttac tctctcacaa tcagccgaat ggaggctgaa    240
gatgctgcca cttattactg ccagcaaagg acttattacc cattcacgtt cggctcgggg    300
acaaagttgg aaataaaacg g                                              321
```

<210> SEQ ID NO 21
<211> LENGTH: 472
<212> TYPE: PRT
<213> ORGANISM: Artificial Sequence
<220> FEATURE:
<223> OTHER INFORMATION: 10D2-1 IgG1 Heavy chain variable region full
      amino acid sequence

<400> SEQUENCE: 21

```
Met Gly Trp Ser Cys Ile Ile Leu Phe Leu Val Ala Thr Ala Thr Gly
1               5                   10                  15

Val His Ser Gln Ile Gln Leu Val Gln Ser Gly Pro Glu Leu Arg Lys
            20                  25                  30

Pro Gly Glu Thr Val Lys Ile Ser Cys Lys Ala Ser Gly Tyr Ser Phe
        35                  40                  45

Thr Asn Tyr Gly Met Asn Trp Val Lys Gln Thr Pro Gly Lys Asp Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Ala Ser Ala Asn
                85                  90                  95

Thr Ala Tyr Leu Gln Ile Asn Asp Leu Lys Asn Glu Asp Met Ala Thr
            100                 105                 110

Tyr Phe Cys Ala Arg Gly Val Ala His Tyr Ser Asp Ser Arg Phe Ala
        115                 120                 125

Phe Asp Tyr Trp Gly Gln Gly Thr Thr Leu Thr Val Pro Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
```

```
            210                 215                 220
Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
                290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 22
<211> LENGTH: 232
<212> TYPE: PRT
<213> ORGANISM: Artificial Sequence
<220> FEATURE:
<223> OTHER INFORMATION: 10D2-1 IgG1 Light chain variable region full
      amino acid sequence

<400> SEQUENCE: 22

Met Gly Trp Ser Cys Ile Ile Leu Phe Leu Val Ala Thr Ala Thr Gly
1               5                   10                  15

Val His Ser Gln Ile Val Leu Thr Gln Ser Pro Ala Ile Met Ser Ala
                20                  25                  30

Ser Pro Gly Glu Lys Val Thr Ile Thr Cys Ser Val Ser Ser Ser Val
                35                  40                  45

Ser Tyr Met His Trp Phe Gln Gln Lys Pro Gly Thr Ser Pro Lys Leu
                50                  55                  60

Trp Ile Tyr Tyr Thr Ser Asn Leu Ala Ser Gly Val Pro Gly Arg Phe
65              70                  75                  80

Ser Gly Ser Gly Ser Gly Thr Ser Tyr Ser Leu Thr Ile Ser Arg Met
                85                  90                  95
```

Glu Ala Glu Asp Ala Ala Thr Tyr Tyr Cys Gln Gln Arg Ser Ser Tyr
            100                 105                 110

Pro Phe Thr Phe Gly Ser Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 23
<211> LENGTH: 495
<212> TYPE: PRT
<213> ORGANISM: Artificial Sequence
<220> FEATURE:
<223> OTHER INFORMATION: 10D2-1 IgA Heavy chain variable region full
      amino acid sequence

<400> SEQUENCE: 23

Met Gly Trp Ser Cys Ile Ile Leu Phe Leu Val Ala Thr Ala Thr Gly
1               5                   10                  15

Val His Ser Gln Ile Gln Leu Val Gln Ser Gly Pro Glu Leu Arg Lys
            20                  25                  30

Pro Gly Glu Thr Val Lys Ile Ser Cys Lys Ala Ser Gly Tyr Ser Phe
        35                  40                  45

Thr Asn Tyr Gly Met Asn Trp Val Lys Gln Thr Pro Gly Lys Asp Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Ala Ser Ala Asn
                85                  90                  95

Thr Ala Tyr Leu Gln Ile Asn Asp Leu Lys Asn Glu Asp Met Ala Thr
            100                 105                 110

Tyr Phe Cys Ala Arg Gly Val Ala His Tyr Ser Asp Ser Arg Phe Ala
        115                 120                 125

Phe Asp Tyr Trp Gly Gln Gly Thr Thr Leu Thr Val Pro Ser Ala Ser
    130                 135                 140

Pro Thr Ser Pro Lys Val Phe Pro Leu Ser Leu Cys Ser Thr Gln Pro
145                 150                 155                 160

Asp Gly Asn Val Val Ile Ala Cys Leu Val Gln Gly Phe Phe Pro Gln
                165                 170                 175

Glu Pro Leu Ser Val Thr Trp Ser Glu Ser Gly Gln Gly Val Thr Ala
            180                 185                 190

Arg Asn Phe Pro Pro Ser Gln Asp Ala Ser Gly Asp Leu Tyr Thr Thr
        195                 200                 205

Ser Ser Gln Leu Thr Leu Pro Ala Thr Gln Cys Leu Ala Gly Lys Ser
    210                 215                 220

```
Val Thr Cys His Val Lys His Tyr Thr Asn Pro Ser Gln Asp Val Thr
225                 230                 235                 240

Val Pro Cys Pro Val Pro Ser Thr Pro Pro Thr Pro Ser Pro Ser Thr
                245                 250                 255

Pro Pro Thr Pro Ser Pro Ser Cys Cys His Pro Arg Leu Ser Leu His
            260                 265                 270

Arg Pro Ala Leu Glu Asp Leu Leu Leu Gly Ser Glu Ala Asn Leu Thr
        275                 280                 285

Cys Thr Leu Thr Gly Leu Arg Asp Ala Ser Gly Val Thr Phe Thr Trp
    290                 295                 300

Thr Pro Ser Ser Gly Lys Ser Ala Val Gln Gly Pro Pro Glu Arg Asp
305                 310                 315                 320

Leu Cys Gly Cys Tyr Ser Val Ser Ser Val Leu Pro Gly Cys Ala Glu
                325                 330                 335

Pro Trp Asn His Gly Lys Thr Phe Thr Cys Thr Ala Ala Tyr Pro Glu
            340                 345                 350

Ser Lys Thr Pro Leu Thr Ala Thr Leu Ser Lys Ser Gly Asn Thr Phe
        355                 360                 365

Arg Pro Glu Val His Leu Leu Pro Pro Ser Glu Glu Leu Ala Leu
370                 375                 380

Asn Glu Leu Val Thr Leu Thr Cys Leu Ala Arg Gly Phe Ser Pro Lys
385                 390                 395                 400

Asp Val Leu Val Arg Trp Leu Gln Gly Ser Gln Glu Leu Pro Arg Glu
                405                 410                 415

Lys Tyr Leu Thr Trp Ala Ser Arg Gln Glu Pro Ser Gln Gly Thr Thr
            420                 425                 430

Thr Phe Ala Val Thr Ser Ile Leu Arg Val Ala Ala Glu Asp Trp Lys
        435                 440                 445

Lys Gly Asp Thr Phe Ser Cys Met Val Gly His Glu Ala Leu Pro Leu
    450                 455                 460

Ala Phe Thr Gln Lys Thr Ile Asp Arg Leu Ala Gly Lys Pro Thr His
465                 470                 475                 480

Val Asn Val Ser Val Val Met Ala Glu Val Asp Gly Thr Cys Tyr
                485                 490                 495

<210> SEQ ID NO 24
<211> LENGTH: 232
<212> TYPE: PRT
<213> ORGANISM: Artificial Sequence
<220> FEATURE:
<223> OTHER INFORMATION: 10D2-1 IgA  Light chain variable region full
    amino acid sequence

<400> SEQUENCE: 24

Met Gly Trp Ser Cys Ile Ile Leu Phe Leu Val Ala Thr Ala Thr Gly
1               5                   10                  15

Val His Ser Gln Ile Val Leu Thr Gln Ser Pro Ala Ile Met Ser Ala
            20                  25                  30

Ser Pro Gly Glu Lys Val Thr Ile Thr Cys Ser Val Ser Ser Ser Val
        35                  40                  45

Ser Tyr Met His Trp Phe Gln Gln Lys Pro Gly Thr Ser Pro Lys Leu
    50                  55                  60

Trp Ile Tyr Tyr Thr Ser Asn Leu Ala Ser Gly Val Pro Gly Arg Phe
65                  70                  75                  80

Ser Gly Ser Gly Ser Gly Thr Ser Tyr Ser Leu Thr Ile Ser Arg Met
```

```
                    85                  90                  95
Glu Ala Glu Asp Ala Ala Thr Tyr Tyr Cys Gln Gln Arg Ser Ser Tyr
                100                 105                 110

Pro Phe Thr Phe Gly Ser Gly Thr Lys Leu Glu Ile Lys Arg Thr Val
            115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
                180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
        210                 215                 220

Lys Ser Phe Asn Arg Gly Glu Cys
225                 230

<210> SEQ ID NO 25
<211> LENGTH: 470
<212> TYPE: PRT
<213> ORGANISM: Artificial Sequence
<220> FEATURE:
<223> OTHER INFORMATION: 28D8-1 IgG1 Heavy chain variable region full
      amino acid sequence

<400> SEQUENCE: 25

Met Gly Trp Ser Cys Ile Ile Leu Phe Leu Val Ala Thr Ala Thr Gly
1               5                   10                  15

Val His Ser Gln Ile Gln Leu Val Gln Ser Gly Pro Glu Leu Lys Lys
                20                  25                  30

Pro Gly Glu Thr Val Lys Ile Ser Cys Lys Ala Ala Gly Tyr Thr Phe
            35                  40                  45

Thr Asp Tyr Gly Met Asn Trp Val Lys Gln Ala Pro Gly Glu Gly Leu
        50                  55                  60

Lys Trp Met Gly Trp Ile Asn Thr Asn Thr Gly Glu Pro Thr Tyr Gly
65                  70                  75                  80

Asp Asp Phe Lys Gly Arg Phe Ala Phe Ser Leu Glu Ala Ser Ala Ser
                85                  90                  95

Thr Ala His Leu Gln Ile Asn Asn Leu Lys Asn Asp Asp Met Ala Ile
                100                 105                 110

Tyr Phe Cys Ala Arg Gly Asn Ala His Pro Gly Gly Ser Ala Phe Val
            115                 120                 125

Tyr Trp Gly Gln Gly Thr Leu Val Thr Val Ser Ala Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205
```

Val Thr Val Pro Ser Ser Leu Gly Thr Gln Thr Tyr Ile Cys Asn
210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 26
<211> LENGTH: 232
<212> TYPE: PRT
<213> ORGANISM: Artificial Sequence
<220> FEATURE:
<223> OTHER INFORMATION: 28D8-1 IgG1 Light chain variable region full
      amino acid sequence

<400> SEQUENCE: 26

Met Gly Trp Ser Cys Ile Ile Leu Phe Leu Val Ala Thr Ala Thr Gly
1               5                   10                  15

Val His Ser Gln Ile Val Leu Thr Gln Ser Pro Ala Ile Met Ser Ala
                20                  25                  30

Ser Pro Gly Glu Ser Val Thr Ile Thr Cys Ser Ala Ser Ser Gly Val
            35                  40                  45

Thr Tyr Met His Trp Phe Gln Gln Lys Pro Gly Thr Ser Pro Lys Asn
        50                  55                  60

Trp Ile Tyr Arg Thr Ser Asn Leu Ala Ser Gly Val Pro Ala Arg Phe
65                  70                  75                  80

Ser Gly Ser Gly Ser Gly Thr Ser Tyr Ser Leu Thr Ile Ser Arg Met
                85                  90                  95

Glu Ala Glu Asp Ala Ala Thr Tyr Tyr Cys Gln Gln Arg Ser Ser Tyr
            100                 105                 110

Pro Phe Thr Phe Gly Ser Gly Thr Lys Leu Glu Ile Lys Arg Thr Val
            115                 120                 125

Ala Ala Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
            165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
            210                 215                 220

Lys Ser Phe Asn Arg Gly Glu Cys
225                 230

<210> SEQ ID NO 27
<211> LENGTH: 493
<212> TYPE: PRT
<213> ORGANISM: Artificial Sequence
<220> FEATURE:
<223> OTHER INFORMATION: 28D8-1 IgA Heavy chain variable region full
      amino acid sequence

<400> SEQUENCE: 27

Met Gly Trp Ser Cys Ile Ile Leu Phe Leu Val Ala Thr Ala Thr Gly
1               5                   10                  15

Val His Ser Gln Ile Gln Leu Val Gln Ser Gly Pro Glu Leu Lys Lys
            20                  25                  30

Pro Gly Glu Thr Val Lys Ile Ser Cys Lys Ala Ala Gly Tyr Thr Phe
            35                  40                  45

Thr Asp Tyr Gly Met Asn Trp Val Lys Gln Ala Pro Gly Glu Gly Leu
50                  55                  60

Lys Trp Met Gly Trp Ile Asn Thr Asn Thr Gly Glu Pro Thr Tyr Gly
65                  70                  75                  80

Asp Asp Phe Lys Gly Arg Phe Ala Phe Ser Leu Glu Ala Ser Ala Ser
            85                  90                  95

Thr Ala His Leu Gln Ile Asn Asn Leu Lys Asn Asp Asp Met Ala Ile
            100                 105                 110

Tyr Phe Cys Ala Arg Gly Asn Ala His Pro Gly Gly Ser Ala Phe Val
            115                 120                 125

Tyr Trp Gly Gln Gly Thr Leu Val Thr Val Ser Ala Ala Ser Pro Thr
130                 135                 140

Ser Pro Lys Val Phe Pro Leu Ser Leu Cys Ser Thr Gln Pro Asp Gly
145                 150                 155                 160

Asn Val Val Ile Ala Cys Leu Val Gln Gly Phe Phe Pro Gln Glu Pro
            165                 170                 175

Leu Ser Val Thr Trp Ser Glu Ser Gly Gln Gly Val Thr Ala Arg Asn
            180                 185                 190

Phe Pro Pro Ser Gln Asp Ala Ser Gly Asp Leu Tyr Thr Thr Ser Ser
            195                 200                 205

Gln Leu Thr Leu Pro Ala Thr Gln Cys Leu Ala Gly Lys Ser Val Thr

```
            210                 215                 220
Cys His Val Lys His Tyr Thr Asn Pro Ser Gln Asp Val Thr Val Pro
225                 230                 235                 240

Cys Pro Val Pro Ser Thr Pro Pro Thr Pro Ser Pro Ser Thr Pro Pro
                245                 250                 255

Thr Pro Ser Pro Ser Cys Cys His Pro Arg Leu Ser Leu His Arg Pro
                260                 265                 270

Ala Leu Glu Asp Leu Leu Leu Gly Ser Glu Ala Asn Leu Thr Cys Thr
            275                 280                 285

Leu Thr Gly Leu Arg Asp Ala Ser Gly Val Thr Phe Thr Trp Thr Pro
            290                 295                 300

Ser Ser Gly Lys Ser Ala Val Gln Gly Pro Pro Glu Arg Asp Leu Cys
305                 310                 315                 320

Gly Cys Tyr Ser Val Ser Ser Val Leu Pro Gly Cys Ala Glu Pro Trp
                325                 330                 335

Asn His Gly Lys Thr Phe Thr Cys Thr Ala Ala Tyr Pro Glu Ser Lys
                340                 345                 350

Thr Pro Leu Thr Ala Thr Leu Ser Lys Ser Gly Asn Thr Phe Arg Pro
                355                 360                 365

Glu Val His Leu Leu Pro Pro Pro Ser Glu Glu Leu Ala Leu Asn Glu
                370                 375                 380

Leu Val Thr Leu Thr Cys Leu Ala Arg Gly Phe Ser Pro Lys Asp Val
385                 390                 395                 400

Leu Val Arg Trp Leu Gln Gly Ser Gln Glu Leu Pro Arg Glu Lys Tyr
                405                 410                 415

Leu Thr Trp Ala Ser Arg Gln Glu Pro Ser Gln Gly Thr Thr Thr Phe
                420                 425                 430

Ala Val Thr Ser Ile Leu Arg Val Ala Ala Glu Asp Trp Lys Lys Gly
                435                 440                 445

Asp Thr Phe Ser Cys Met Val Gly His Glu Ala Leu Pro Leu Ala Phe
                450                 455                 460

Thr Gln Lys Thr Ile Asp Arg Leu Ala Gly Lys Pro Thr His Val Asn
465                 470                 475                 480

Val Ser Val Val Met Ala Glu Val Asp Gly Thr Cys Tyr
                485                 490

<210> SEQ ID NO 28
<211> LENGTH: 232
<212> TYPE: PRT
<213> ORGANISM: Artificial Sequence
<220> FEATURE:
<223> OTHER INFORMATION: 28D8-1 IgA Light chain variable region full
      amino acid sequence

<400> SEQUENCE: 28

Met Gly Trp Ser Cys Ile Ile Leu Phe Leu Val Ala Thr Ala Thr Gly
1               5                   10                  15

Val His Ser Gln Ile Val Leu Thr Gln Ser Pro Ala Ile Met Ser Ala
                20                  25                  30

Ser Pro Gly Glu Ser Val Thr Ile Thr Cys Ser Ala Ser Ser Gly Val
            35                  40                  45

Thr Tyr Met His Trp Phe Gln Gln Lys Pro Gly Thr Ser Pro Lys Asn
        50                  55                  60

Trp Ile Tyr Arg Thr Ser Asn Leu Ala Ser Gly Val Pro Ala Arg Phe
65                  70                  75                  80
```

```
Ser Gly Ser Gly Ser Gly Thr Ser Tyr Ser Leu Thr Ile Ser Arg Met
                 85                  90                  95
Glu Ala Glu Asp Ala Ala Thr Tyr Tyr Cys Gln Gln Arg Ser Ser Tyr
            100                 105                 110
Pro Phe Thr Phe Gly Ser Gly Thr Lys Leu Glu Ile Lys Arg Thr Val
        115                 120                 125
Ala Ala Pro Ser Val Phe Ile Phe Pro Pro Ser Asp Glu Gln Leu Lys
    130                 135                 140
Ser Gly Thr Ala Ser Val Val Cys Leu Leu Asn Asn Phe Tyr Pro Arg
145                 150                 155                 160
Glu Ala Lys Val Gln Trp Lys Val Asp Asn Ala Leu Gln Ser Gly Asn
                165                 170                 175
Ser Gln Glu Ser Val Thr Glu Gln Asp Ser Lys Asp Ser Thr Tyr Ser
            180                 185                 190
Leu Ser Ser Thr Leu Thr Leu Ser Lys Ala Asp Tyr Glu Lys His Lys
        195                 200                 205
Val Tyr Ala Cys Glu Val Thr His Gln Gly Leu Ser Ser Pro Val Thr
    210                 215                 220
Lys Ser Phe Asn Arg Gly Glu Cys
225                 230

<210> SEQ ID NO 29
<211> LENGTH: 1433
<212> TYPE: DNA
<213> ORGANISM: Artificial Sequence
<220> FEATURE:
<223> OTHER INFORMATION: 28D8-1_mIgG2b-pcDNA3.1(+)

<400> SEQUENCE: 29
atggattggc tgtggaactt gctattcctg atggcagcag cccaaagcgc ccaaacacag      60
atccagttgg tgcagtctgg acctgagctg aagaagcctg agagacagt caagatctcc     120 tgcaaggctg ctgggtatac cttcacagac tatggaatga actgggtgaa gcaggctcca     180
ggagagggtt taaagtggat gggctggata acaccaata ctggagagcc aacatatggt     240
gatgacttca aggacggtt tgccttctct ttggaagcct ctgccagcac tgcccatttg     300
cagatcaaca acctcaaaaa tgacgacatg gcaatatatt tctgtgcaag agggaacgct     360
catcccggtg gtagtgcgtt tgtttactgg ggccaaggga ctctggtcac tgtctctgca     420
gccaaaacaa cacccccatc agtctatcca ctggcccctg ggtgtggaga taccaactggt   480 tcctctgtga ctctgggatg cctggtcaag ggctacttcc ctgagtcagt gactgtgact     540
tggaactctg gatccctgtc agcagtgtg cacaccttcc cagctctcct gcagtctgga     600
ctctacacta tgagcagctc agtgactgtc cctccagca cctggccaag tcagaccgtc     660
acctgcagcg ttgctcaccc agccagcagc accacggtgg acaaaaaact tgagcccagc     720
gggcccattt caacaatcaa ccctgtcct ccatgcaagg agtgtcacaa atgcccagct     780
cctaacctcg agggtggacc atccgtcttc atcttccctc caaatatcaa ggatgtactc     840
atgatctccc tgacacccaa ggtcacgtgt gtggtggtgg atgtgagcga ggatgaccca     900
gacgtccgga tcagctggtt tgtgaacaac gtggaagtac acacagctca gacacaaacc     960
catagagagg attacaacag tactatccgg gtggtcagtg ccctcccat ccagcaccag    1020 gactggatga gtggcaagga gttcaaatgc aaggtcaaca acaagacct cccatcaccc    1080 atcgagagaa ccatctcaaa aattaaaggg ctagtcagag ctccacaagt atacatcttg    1140
ccgccaccag cagagcagtt gtccaggaaa gatgtcagtc tcacttgcct ggtcgtgggc    1200
```

| | |
|---|---|
| ttcaaccctg gagacatcag tgtggagtgg accagcaatg gcatacaga ggagaactac | 1260 |
| aaggacaccg caccagtcct ggactctgac ggttcttact tcatatacag caagctcgat | 1320 |
| ataaaaacaa gcaagtggga gaaaacagat tccttctcat gcaacgtgag acacgagggt | 1380 |
| ctgaaaaatt actacctgaa gaagaccatc tcccggtctc cgggtaaatg agc | 1433 |

```
<210> SEQ ID NO 30
<211> LENGTH: 384
<212> TYPE: DNA
<213> ORGANISM: Artificial Sequence
<220> FEATURE:
<223> OTHER INFORMATION: 28D8-1_mKappa-pcDNA3.1(+)

<400> SEQUENCE: 30
```

| | |
|---|---|
| atgcattttc aagtgcagat tttcagcttc ctgctaatca gtgcctcagt cataatgtcc | 60 |
| agaggacaaa ttgttctcac ccagtctcca gcaatcatgt ctgcatctcc aggggagagt | 120 |
| gtcaccataa cctgcagtgc cagctcaggt gtcacttaca tgcactggtt ccagcagaag | 180 |
| ccaggcactt ctcccaaaaa ctggatttat agaacatcca atctggcttc tggagtccct | 240 |
| gctcgcttca gtggcagtgg atctgggacc tcttactctc tcacaatcag ccgaatggag | 300 |
| gctgaagatg ctgccactta ttactgccag caaaggagta gttacccatt cacattcggc | 360 |
| tcggggacaa agttggaaat aaaa | 384 |

```
<210> SEQ ID NO 31
<211> LENGTH: 426
<212> TYPE: DNA
<213> ORGANISM: Artificial Sequence
<220> FEATURE:
<223> OTHER INFORMATION: 10D2-1_mIgG1-pcDNA3.1(+)

<400> SEQUENCE: 31
```

| | |
|---|---|
| atggattggc tgtggaactt gctattcctg atggcagctg cccaaagtgc ccaaacacag | 60 |
| atccagttgg tgcagtctgg acctgagttg aggaagcctg gagagacagt caagatctcc | 120 |
| tgcaaggctt ctggatattc cttcacaaac tatggaatga actgggtgaa gcagactcca | 180 |
| ggaaaggatt taaagtggat gggctggata aacacctaca ctggagagcc aacatatgct | 240 |
| gatgacttca agggacggtt cgccttctct ctggaagcct ctgccaacac tgcctatttg | 300 |
| cagatcaacg acctcaaaaa tgaggacatg gctacatatt tctgtgcaag gggtgtggct | 360 |
| cattactccg atagtaggtt cgcctttgac tactggggcc aaggaaccac tctcacagtc | 420 |
| ccctcc | 426 |

```
<210> SEQ ID NO 32
<211> LENGTH: 384
<212> TYPE: DNA
<213> ORGANISM: Artificial Sequence
<220> FEATURE:
<223> OTHER INFORMATION: 10D2-1_mKappa-pcDNA3.1(+)

<400> SEQUENCE: 32
```

| | |
|---|---|
| atgcattttc aagtgcagat tttcagcttc ctgctaatca gtgcctcagt cataatgtcc | 60 |
| agaggacaaa ttgttctcac ccagtcacca gcaatcatgt ctgcatctcc aggggagaag | 120 |
| gtcaccataa cctgcagtgt cagctcaagt gttagttaca tgcactggtt ccagcagaag | 180 |
| ccaggcactt ctcccaaact ctggatttat tacacatcca acctggcttc tggagtccct | 240 |
| ggtcgcttca gtggcagtgg atctgggacc tcttactccc tcacaatcag ccgaatggag | 300 |

```
gctgaagatg ctgccactta ttactgccag caaaggagta gttacccatt cacgttcggc    360
tcggggacaa agttggaaat aaaa                                           384
```

```
<210> SEQ ID NO 33
<211> LENGTH: 5
<212> TYPE: PRT
<213> ORGANISM: Artificial Sequence
<220> FEATURE:
<223> OTHER INFORMATION: 10D2-1 Heavy chain variable region CDR1

<400> SEQUENCE: 33

Asn Tyr Gly Met Asn
1               5

<210> SEQ ID NO 34
<211> LENGTH: 17
<212> TYPE: PRT
<213> ORGANISM: Artificial Sequence
<220> FEATURE:
<223> OTHER INFORMATION: 10D2-1 Heavy chain variable region CDR2

<400> SEQUENCE: 34

Trp Ile Asn Thr Tyr Thr Gly Glu Pro Thr Tyr Ala Asp Asp Phe Lys
1               5                   10                  15
Gly

<210> SEQ ID NO 35
<211> LENGTH: 14
<212> TYPE: PRT
<213> ORGANISM: Artificial Sequence
<220> FEATURE:
<223> OTHER INFORMATION: 10D2-1 Heavy chain variable region CDR3

<400> SEQUENCE: 35

Gly Val Ala His Tyr Ser Asp Ser Arg Phe Ala Phe Asp Tyr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: 10D2-1 Light chain variable region CDR1

<400> SEQUENCE: 36

Ser Val Ser Ser Ser Val Ser Tyr Met His
1               5                   10

<210> SEQ ID NO 37
<211> LENGTH: 7
<212> TYPE: PRT
<213> ORGANISM: Artificial Sequence
<220> FEATURE:
<223> OTHER INFORMATION: 10D2-1 Light chain variable region CDR2

<400> SEQUENCE: 37

Tyr Thr Ser Asn Leu Ala Ser
1               5

<210> SEQ ID NO 38
<211> LENGTH: 9
<212> TYPE: PRT
<213> ORGANISM: Artificial Sequence
<220> FEATURE:
<223> OTHER INFORMATION: 10D2-1 Light chain variable region CDR3
```

```
<400> SEQUENCE: 38

Gln Gln Arg Ser Ser Tyr Pro Phe Thr
1               5

<210> SEQ ID NO 39
<211> LENGTH: 5
<212> TYPE: PRT
<213> ORGANISM: Artificial Sequence
<220> FEATURE:
<223> OTHER INFORMATION: 28D8-1 Heavy chain variable region CDR1

<400> SEQUENCE: 39

Asp Tyr Gly Met Asn
1               5

<210> SEQ ID NO 40
<211> LENGTH: 17
<212> TYPE: PRT
<213> ORGANISM: Artificial Sequence
<220> FEATURE:
<223> OTHER INFORMATION: 28D8-1 Heavy chain variable region CDR2

<400> SEQUENCE: 40

Trp Ile Asn Thr Asn Thr Gly Glu Pro Thr Tyr Gly Asp Asp Phe Lys
1               5                   10                  15

Gly

<210> SEQ ID NO 41
<211> LENGTH: 12
<212> TYPE: PRT
<213> ORGANISM: Artificial Sequence
<220> FEATURE:
<223> OTHER INFORMATION: 28D8-1 Heavy chain variable region CDR3

<400> SEQUENCE: 41

Gly Asn Ala His Pro Gly Gly Ser Ala Phe Val Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: 28D8-1 Light chain variable region CDR1

<400> SEQUENCE: 42

Ser Ala Ser Ser Gly Val Thr Tyr Met His
1               5                   10

<210> SEQ ID NO 43
<211> LENGTH: 7
<212> TYPE: PRT
<213> ORGANISM: Artificial Sequence
<220> FEATURE:
<223> OTHER INFORMATION: 28D8-1 Light chain variable region CDR2

<400> SEQUENCE: 43

Arg Thr Ser Asn Leu Ala Ser
1               5

<210> SEQ ID NO 44
<211> LENGTH: 9
<212> TYPE: PRT
<213> ORGANISM: Artificial Sequence
<220> FEATURE:
<223> OTHER INFORMATION: 28D8-1 Light chain variable region CDR3 amino
``` acid sequence

<400> SEQUENCE: 44

Gln Gln Arg Ser Ser Tyr Pro Phe Thr
1               5

<210> SEQ ID NO 45
<211> LENGTH: 12
<212> TYPE: PRT
<213> ORGANISM: Artificial Sequence
<220> FEATURE:
<223> OTHER INFORMATION: synthetic

<400> SEQUENCE: 45

Gln Gly Ala Gly Lys Asp Asn Val Asp Tyr Ser Ser
1               5                   10

<210> SEQ ID NO 46
<211> LENGTH: 9
<212> TYPE: PRT
<213> ORGANISM: Artificial Sequence
<220> FEATURE:
<223> OTHER INFORMATION: 1C4F4 HC ARB1

<400> SEQUENCE: 46

Tyr Thr Phe Thr Asn Tyr Gly Met Asn
1               5

<210> SEQ ID NO 47
<211> LENGTH: 14
<212> TYPE: PRT
<213> ORGANISM: Artificial Sequence
<220> FEATURE:
<223> OTHER INFORMATION: 1C4F4 HC ARB2

<400> SEQUENCE: 47

Trp Met Gly Trp Ile Asn Thr Tyr Thr Gly Glu Pro Thr Tyr
1               5                   10

<210> SEQ ID NO 48
<211> LENGTH: 15
<212> TYPE: PRT
<213> ORGANISM: Artificial Sequence
<220> FEATURE:
<223> OTHER INFORMATION: 1C4F4 HC ARB3

<400> SEQUENCE: 48

Arg Gly Ser Tyr Tyr Tyr Asp Ser Ser Pro Ala Trp Phe Ala Tyr
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: 1C4F4 LC ARB1

<400> SEQUENCE: 49

Ser Ser Val Ser Tyr Met His
1               5

<210> SEQ ID NO 50
<211> LENGTH: 11
<212> TYPE: PRT
<213> ORGANISM: Artificial Sequence
<220> FEATURE:
<223> OTHER INFORMATION: 1C4F4 LC  ARB2

<400> SEQUENCE: 50

Leu Trp Ile Tyr Ser Thr Ser Asn Leu Ala Ser
1               5                   10

<210> SEQ ID NO 51
<211> LENGTH: 8
<212> TYPE: PRT
<213> ORGANISM: Artificial Sequence
<220> FEATURE:
<223> OTHER INFORMATION: 1C4F4 LC  ARB3

<400> SEQUENCE: 51

Gln Gln Arg Ser Thr Tyr Pro Phe
1               5

<210> SEQ ID NO 52
<211> LENGTH: 9
<212> TYPE: PRT
<213> ORGANISM: Artificial Sequence
<220> FEATURE:
<223> OTHER INFORMATION: 6E10B5 HC ARB1

<400> SEQUENCE: 52

Tyr Thr Phe Thr Lys Tyr Gly Met Asn
1               5

<210> SEQ ID NO 53
<211> LENGTH: 14
<212> TYPE: PRT
<213> ORGANISM: Artificial Sequence
<220> FEATURE:
<223> OTHER INFORMATION: 6E10B5 HC ARB2

<400> SEQUENCE: 53

Trp Met Gly Trp Ile Asn Thr Tyr Thr Gly Glu Pro Thr Tyr
1               5                   10

<210> SEQ ID NO 54
<211> LENGTH: 13
<212> TYPE: PRT
<213> ORGANISM: Artificial Sequence
<220> FEATURE:
<223> OTHER INFORMATION: 6E10B5 HC ARB3

<400> SEQUENCE: 54

Arg Gly Val Asp Ser Ser Gly Tyr Gly Ala Phe Ala Tyr
1               5                   10

<210> SEQ ID NO 55
<211> LENGTH: 7
<212> TYPE: PRT
<213> ORGANISM: Artificial Sequence
<220> FEATURE:
<223> OTHER INFORMATION: 6E10B5 LC ARB1

<400> SEQUENCE: 55

Ser Ser Val Ser Tyr Met His
1               5

<210> SEQ ID NO 56
<211> LENGTH: 11
<212> TYPE: PRT
<213> ORGANISM: Artificial Sequence
<220> FEATURE:
<223> OTHER INFORMATION: 6E10B5 LC ARB2

```
<400> SEQUENCE: 56

Leu Trp Ile Tyr Ser Thr Ser Asn Leu Ala Ser
1               5                   10

<210> SEQ ID NO 57
<211> LENGTH: 8
<212> TYPE: PRT
<213> ORGANISM: Artificial Sequence
<220> FEATURE:
<223> OTHER INFORMATION: 6E10B5 LC ARB3

<400> SEQUENCE: 57

Gln Gln Arg Ser Phe Tyr Pro Phe
1               5

<210> SEQ ID NO 58
<211> LENGTH: 9
<212> TYPE: PRT
<213> ORGANISM: Artificial Sequence
<220> FEATURE:
<223> OTHER INFORMATION: 7D4B9 HC ARB1

<400> SEQUENCE: 58

Tyr Thr Phe Thr Asn Tyr Gly Met Asn
1               5

<210> SEQ ID NO 59
<211> LENGTH: 14
<212> TYPE: PRT
<213> ORGANISM: Artificial Sequence
<220> FEATURE:
<223> OTHER INFORMATION: 7D4B9 HC ARB2

<400> SEQUENCE: 59

Trp Met Gly Trp Ile Asn Thr Tyr Thr Gly Glu Pro Thr Tyr
1               5                   10

<210> SEQ ID NO 60
<211> LENGTH: 15
<212> TYPE: PRT
<213> ORGANISM: Artificial Sequence
<220> FEATURE:
<223> OTHER INFORMATION: 7D4B9 HC ARB3

<400> SEQUENCE: 60

Thr Arg Gly Thr Ser Thr Met Ile Ser Thr Phe Ala Phe Val Tyr
1               5                   10                  15

<210> SEQ ID NO 61
<211> LENGTH: 7
<212> TYPE: PRT
<213> ORGANISM: Artificial Sequence
<220> FEATURE:
<223> OTHER INFORMATION: 7D4B9 LC ARB1

<400> SEQUENCE: 61

Ser Ser Val Arg Tyr Met His
1               5

<210> SEQ ID NO 62
<211> LENGTH: 11
<212> TYPE: PRT
<213> ORGANISM: Artificial Sequence
<220> FEATURE:
<223> OTHER INFORMATION: 7D4B9 LC ARB2

<400> SEQUENCE: 62
```

```
Val Trp Ile Tyr Ser Thr Ser Asn Leu Ala Ser
1               5                   10

<210> SEQ ID NO 63
<211> LENGTH: 8
<212> TYPE: PRT
<213> ORGANISM: Artificial Sequence
<220> FEATURE:
<223> OTHER INFORMATION: 7D4B9 LC ARB3

<400> SEQUENCE: 63

Gln Gln Arg Thr Tyr Tyr Pro Phe
1               5
```

ADENO-ASSOCIATED VIRUS ANTIBODIES, FRAGMENTS THEREOF AND ENCODING POLYNUCLEOTIDES

CROSS-REFERENCE TO RELATED APPLICATIONS

This application is a continuation of U.S. patent application Ser. No. 17/348,356, filed Jun. 15, 2021, which claims the benefit under 35 U.S.C. § 119(e) of U.S. Provisional Application No. 63/038,957, filed Jun. 15, 2020, the contents of which are hereby incorporated by reference in their entireties.

REFERENCE TO SEQUENCE LISTING SUBMITTED ELECTRONICALLY

The content of the electronically submitted sequence listing in ASCII text file (Name: 4140_0530002_Seqlisting_ST25.txt; Size: 55,248 bytes; and Date of Creation: Sep. 13, 2021), filed with the application, is incorporated herein by reference in its entirety.

BACKGROUND

Adeno-associated viruses (AAV) are one kind of (approximately 25 nm) non-enveloped, single-stranded DNA parvoviruses. AAVs have become attractive vehicles for gene transfer because of characteristics such as their ability to transduce different types of dividing and non-dividing cells of different tissues and their ability to establish stable, long-term transgene expression. Further, AAVs do not naturally exhibit pathogenicity in humans. There are more than 100 human and nonhuman primate AAVs that have been identified, including 12 serotypes that have between 51% and 99% identity in capsid amino acid sequence.

The AAV capsid protein determines tissue tropism and thus is the primary interface between targeted tissues and AAV vectors. However, due to similarities in structure and amino acid sequences of capsid proteins from some AAV serotypes used in gene therapy, antibodies that recognize the capsid protein of one AAV serotype will cross-react with capsid proteins from other AAV serotypes. In particular, there is a need for antibodies that can differentiate or specifically identify AAVrh74 from AAVs of other serotypes, e.g., AAV8 and/or AAV9. There is also a need for a reliable method of measuring or quantifying the levels of AAVrh74-specific antibody in the serum of patients undergoing gene therapy with AAVrh74.

BRIEF SUMMARY OF THE INVENTION

The present disclosed invention relates to a murine, humanized or chimeric antibody that binds the epitope of AAV capsid protein. More specifically, the present disclosure provides an isolated anti-AAV (adeno-associated virus) antibody or an antigen-binding fragment thereof capable of specifically binding an epitope of AAV capsid protein, wherein the epitope comprises the amino acid sequence QGAGKDNVDYSS (SEQ ID NO: 45) or a portion thereof. In another aspect, the invention relates to a murine, humanized or chimeric antibody that binds the epitope of AAVrh74 capsid protein, wherein the epitope comprises the amino acid sequence QGAGKDNVDYSS (SEQ ID NO: 45) or a portion thereof. In one embodiment, the antibody is a monoclonal or polyclonal antibody. In another embodiment, the capsid protein is an AAVrh74 capsid protein. In one embodiment, the antibody is an anti-AAV antibody.

The present disclosure further provides an isolated anti-AAV antibody or antigen binding fragment thereof that specifically binds an epitope within AAVrh74 capsid protein, wherein the antibody competes for binding the epitope with a reference antibody, wherein (a) the heavy chain variable region of the reference antibody comprises an amino acid sequence selected from the group consisting of: SEQ ID NO: 1, SEQ ID NO: 5, SEQ ID NO: 13, SEQ ID NO: 9, and SEQ ID NO: 17; and (b) the light chain variable region of the reference antibody comprises an amino acid sequence selected from the group consisting of: SEQ ID NO: 2, SEQ ID NO: 6, SEQ ID NO: 14, SEQ ID NO: 10, and SEQ ID NO: 18.

The present disclosure also provides an isolated antibody or antigen-binding fragment thereof that comprises a heavy chain variable region that comprises VH CDR1, VH CDR2, and VH CDR3 domains and a light chain variable region that comprises VL CDR1, VL CDR2, and VL CDR3 domains, wherein (a) the VH CDR1 domain comprises an amino acid sequence selected from the group consisting of SEQ ID NO: 33, SEQ ID NO: 39, SEQ ID NO: 46, SEQ ID NO: 52, and SEQ ID NO: 58; (b) the VH CDR2 domain comprises an amino acid sequence selected from the group consisting of SEQ ID NO: 34, SEQ ID NO: 40, SEQ ID NO: 47, SEQ ID NO: 53, and SEQ ID NO: 59; (c) the VH CDR3 domain comprises an amino acid sequence selected from the group consisting of SEQ ID NO: 35, SEQ ID NO: 41, SEQ ID NO: 48, SEQ ID NO: 54, and SEQ ID NO: 60; (d) the VL CDR1 domain comprises an amino acid sequence selected from the group consisting of SEQ ID NO: 36, SEQ ID NO: 42, SEQ ID NO: 49, SEQ ID NO: 55, and SEQ ID NO: 61; (e) the VL CDR2 domain comprises an amino acid sequence selected from the group consisting of SEQ ID NO: 37, SEQ ID NO: 43, SEQ ID NO: 50, SEQ ID NO: 56, and SEQ ID NO: 62; or (f) the VL CDR3 domain comprises an amino acid sequence selected from the group consisting of SEQ ID NO: 38, SEQ ID NO: 44, SEQ ID NO: 51, SEQ ID NO: 57, and SEQ ID NO: 63.

The present disclosure further provides an isolated antibody or antigen-binding fragment thereof, comprising (a) a heavy chain variable region comprising an amino acid sequence selected from the group consisting of: SEQ ID NO: 1, SEQ ID NO: 5, SEQ ID NO: 13, SEQ ID NO: 9, and SEQ ID NO: 17; and (b) a light chain variable region comprising an amino acid sequence selected from the group consisting of: SEQ ID NO: 2, SEQ ID NO: 6, SEQ ID NO: 14, SEQ ID NO: 10, and SEQ ID NO: 18.

In some aspects of the disclosure, the isolated antibody or antigen-binding fragment thereof binds to the capsid protein of AAV8 and/or AAV9 with less affinity as compared to an equivalent protein or a capsid protein of AAVrh74.

In some aspects, the heavy chain variable region of the isolated antibody or antigen binding fragment thereof comprises a VH CDR3 selected from the group consisting of

```
                              (SEQ ID NO: 35)
    GVAHYSDSRFAFDY, (SEQ ID NO: 41)
    GNAHPGGSAFVY, (SEQ ID NO: 48)
    RGSYYYDSSPAWFAY,
```

-continued

RGVDSSGYGAFAY, (SEQ ID NO: 54)
and

TRGTSTMISTFAFVY. (SEQ ID NO: 60)

In some aspects, the heavy chain variable region of the isolated antibody or antigen binding fragment thereof further comprises a VH CDR1 selected from the group consisting of

NYGMN, (SEQ ID NO: 33)

DYGMN, (SEQ ID NO: 39)

YTFTNYGMN, (SEQ ID NO: 46)

YTFTKYGMN, (SEQ ID NO: 52)
and

YTFTNYGMN. (SEQ ID NO: 58)

In some aspects, the heavy chain variable region of the isolated antibody or antigen binding fragment thereof further comprises a VH CDR2 selected from the group consisting of

WINTYTGEPTYADDFKG, (SEQ ID NO: 34)

WINTNTGEPTYGDDFKG, (SEQ ID NO: 40)

WMGWINTYTGEPTY, (SEQ ID NO: 47)

WMGWINTYTGEPTY, (SEQ ID NO: 53)
and

WMGWINTYTGEPTY. (SEQ ID NO: 59)

In some aspects, the light chain variable region of the isolated antibody or antigen binding fragment thereof comprises a VL CDR1 selected from the group consisting of SVSSSVSYMH (SEQ ID NO: 36), SASSGVTYMH (SEQ ID NO: 42), SSVSYMH (SEQ ID NO: 49), SSVSYMH (SEQ ID NO: 55), and SSVRYMH (SEQ ID NO: 61).

In some aspects, the light chain variable region of the isolated antibody or antigen binding fragment thereof further comprises a VL CDR2 selected from the group consisting of

YTSNLAS, (SEQ ID NO: 37)

RTSNLAS, (SEQ ID NO: 43)

LWIYSTSNLAS, (SEQ ID NO: 50)

LWIYSTSNLAS, (SEQ ID NO: 56)
and

VWIYSTSNLAS. (SEQ ID NO: 62)

In some aspects, the light chain variable region further of the isolated antibody or antigen binding fragment thereof further comprises a VL CDR3 selected from the group consisting of QQRSSYPFT (SEQ ID NO: 38), QQRSSYPFT (SEQ ID NO: 44), QQRSTYPF (SEQ ID NO: 51), QQRSFYPF (SEQ ID NO: 57), and QQRTYYPF (SEQ ID NO: 63).

In some aspects, the isolated antibody or antigen binding fragment thereof comprises a heavy chain variable region that comprises VH CDR1, VH CDR2, and VH CDR3 domains and a light chain variable region that comprises VL CDR1, VL CDR2, and VL CDR3 domains selected from the group consisting of:

a. a VH CDR1 having the amino acid sequence set forth in SEQ ID NO: 33, a VH CDR2 having the amino acid sequence set forth in SEQ ID NO: 34, a VH CDR3 having the amino acid sequence set forth in SEQ ID NO: 35, a VL CDR1 having the amino acid sequence set forth in SEQ ID NO: 36, a VL CDR2 having the amino acid sequence set forth in SEQ ID NO: 37, and a VL CDR3 having the amino acid sequence set forth in SEQ ID NO: 38;

b. a VH CDR1 having the amino acid sequence set forth in SEQ ID NO: 39, a VH CDR2 having the amino acid sequence set forth in SEQ ID NO: 40, a VH CDR3 having the amino acid sequence set forth in SEQ ID NO: 41, a VL CDR1 having the amino acid sequence set forth in SEQ ID NO: 42, a VL CDR2 having the amino acid sequence set forth in SEQ ID NO: 43, and a VL CDR3 having the amino acid sequence set forth in SEQ ID NO: 44;

c. a VH CDR1 having the amino acid sequence set forth in SEQ ID NO: 46, a VH CDR2 having the amino acid sequence set forth in SEQ ID NO: 47, a VH CDR3 having the amino acid sequence set forth in SEQ ID NO: 48, a VL CDR1 having the amino acid sequence set forth in SEQ ID NO: 49, a VL CDR2 having the amino acid sequence set forth in SEQ ID NO: 50, and a VL CDR3 having the amino acid sequence set forth in SEQ ID NO: 51;

d. a VH CDR1 having the amino acid sequence set forth in SEQ ID NO: 52, a VH CDR2 having the amino acid sequence set forth in SEQ ID NO: 53, a VH CDR3 having the amino acid sequence set forth in SEQ ID NO: 54, a VL CDR1 having the amino acid sequence set forth in SEQ ID NO: 55 a VL CDR2 having the amino acid sequence set forth in SEQ ID NO: 56, and a VL CDR3 having the amino acid sequence set forth in SEQ ID NO: 57; and e. a VH CDR1 having the amino acid sequence set forth in SEQ ID NO: 58, a VH CDR2 having the amino acid sequence set forth in SEQ ID NO: 59, a VH CDR3 having the amino acid sequence set forth in SEQ ID NO: 60, a VL CDR1 having the amino acid sequence set forth in SEQ ID NO: 61, a VL CDR2 having the amino acid sequence set forth in SEQ ID NO: 62, and a VL CDR3 having the amino acid sequence set forth in SEQ ID NO: 63.

In some aspects, the isolated antibody or antigen binding fragment thereof comprises:

a. a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 1; and a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 2;

b. a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 5; and a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 6;

c. a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 13; and a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 14;

d. a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 9; and a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 10; or e. a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 17; and a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 18.

In some aspects of the disclosure, the heavy chain variable region of the isolated antibody or antigen binding fragment thereof is selected from the group consisting of SEQ ID NO: 1, SEQ ID NO: 5, SEQ ID NO: 13, SEQ ID NO: 9, and SEQ ID NO: 17.

In some aspects, the light chain variable region of the isolated antibody or antigen binding fragment thereof is selected from the group consisting of SEQ ID NO: 2, SEQ ID NO: 6, SEQ ID NO: 14, SEQ ID NO: 10, and SEQ ID NO: 18.

In some aspects of the disclosure, the heavy chain variable region of the isolated antibody or antigen binding fragment thereof comprises an amino acid sequence selected from the group consisting of SEQ ID NO: 1, SEQ ID NO: 5, SEQ ID NO: 13, SEQ ID NO: 9, and SEQ ID NO: 17; and the light chain variable region comprises an amino acid sequence selected from the group consisting of SEQ ID NO: 2, SEQ ID NO: 6, SEQ ID NO: 14, SEQ ID NO: 10, and SEQ ID NO: 18.

In some aspects, the isolated antibody or antigen binding fragment thereof comprises a heavy chain variable region comprising the amino acid sequence set forth in SEQ ID NO: 1 and a light chain variable region comprising the amino acid sequence set forth in SEQ ID NO: 2.

In some aspects, the isolated antibody or antigen binding fragment thereof comprises a heavy chain variable region comprising the amino acid sequence set forth in SEQ ID NO: 5 and a light chain variable region comprising the amino acid sequence set forth in SEQ ID NO: 6.

In some aspects, the isolated antibody or antigen binding fragment thereof comprises a heavy chain variable region comprising the amino acid sequence set forth in SEQ ID NO: 13 and a light chain variable region comprising the amino acid sequence set forth in SEQ ID NO: 14.

In some aspects, the isolated antibody or antigen binding fragment thereof comprises a heavy chain variable region comprising the amino acid sequence set forth in SEQ ID NO: 9 and a light chain variable region comprising the amino acid sequence set forth in SEQ ID NO: 10.

In some aspects, the isolated antibody or antigen binding fragment thereof comprises a heavy chain variable region comprising the amino acid sequence set forth in SEQ ID NO: 17 and a light chain variable region comprising the amino acid sequence set forth in SEQ ID NO: 18.

In some aspects of the disclosure, the isolated antibody or antigen binding fragment thereof is labeled with a radioactive, enzymatic, or fluorescent group.

In some aspects, the isolated antibody is a full-length antibody or an antibody fragment selected from the group consisting of Fab, Fab', Fab'-SH, Fd, Fv, dAb, F(ab')2, scFv, bispecific single chain Fv dimers, diabodies, triabodies, and sxFv genetically fused to the same or a different antibody.

In some aspects, the isolated antibody is a murine antibody, a chimeric murine/human antibody, a human antibody, an engineered antibody, or a humanized antibody.

In some aspects, the isolated antibody is a chimeric antibody comprising a heavy chain comprising the amino acid sequence set forth in SEQ ID NO: 21 and a light chain comprising the amino acid sequence set forth in SEQ ID NO: 22.

In some aspects, the isolated antibody is a chimeric antibody comprising a heavy chain comprising the amino acid sequence set forth in SEQ ID NO: 23 and a light chain comprising the amino acid sequence set forth in SEQ ID NO: 24.

In some aspects, the isolated antibody is a chimeric antibody comprising a heavy chain comprising the amino acid sequence set forth in SEQ ID NO: 25 and a light chain comprising the amino acid sequence set forth in SEQ ID NO: 26.

In some aspects, the isolated antibody is a chimeric antibody comprising a heavy chain comprising the amino acid sequence set forth in SEQ ID NO: 27 and a light chain comprising the amino acid sequence set forth in SEQ ID NO: 28.

In some aspects, the isolated antibody or antigen-binding fragment thereof is a bispecific antibody.

In some aspects, the isolated antibody or antigen-binding fragment thereof is a multispecific antibody.

The present disclosure also provides an isolated polynucleotide comprising a nucleic acid sequence encoding the antibody or antigen binding fragment thereof as described herein.

In some aspects, the polynucleotide of the disclosure comprises a nucleic acid sequence encoding (a) a VH CDR1 domain comprising an amino acid sequence selected from the group consisting of SEQ ID NO: 33, SEQ ID NO: 39, SEQ ID NO: 46, SEQ ID NO: 52, and SEQ ID NO: 58; (b) a VH CDR2 domain comprises an amino acid sequence selected from the group consisting of SEQ ID NO: 34, SEQ ID NO: 40, SEQ ID NO: 47, SEQ ID NO: 53, and SEQ ID NO: 59; (c) a VH CDR3 domain comprises an amino acid sequence selected from the group consisting of SEQ ID NO: 35, SEQ ID NO: 41, SEQ ID NO: 48, SEQ ID NO: 54, and SEQ ID NO: 60; (d) a VL CDR1 domain comprises an amino acid sequence selected from the group consisting of SEQ ID NO: 36, SEQ ID NO: 42, SEQ ID NO: 49, SEQ ID NO: 55, and SEQ ID NO: 61; (e) a VL CDR2 domain comprises an amino acid sequence selected from the group consisting of SEQ ID NO: 37, SEQ ID NO: 43, SEQ ID NO: 50, SEQ ID NO: 56, and SEQ ID NO: 62; and (f) a VL CDR3 domain comprises an amino acid sequence selected from the group consisting of SEQ ID NO: 38, SEQ ID NO: 44, SEQ ID NO: 51, SEQ ID NO: 57, and SEQ ID NO: 63.

In some aspects of the disclosure, the nucleic acid sequence encoding the heavy chain variable region of the antibody or antigen binding fragment thereof comprises a nucleotide sequence selected from the group consisting of SEQ ID NO: 3; SEQ ID NO: 7; SEQ ID NO: 15; SEQ ID NO: 11; and SEQ ID NO: 19; and the nucleic acid sequence encoding the light chain variable region of the antibody or antigen binding fragment thereof comprises a nucleotide sequence selected from the group consisting of SEQ ID NO: 4; SEQ ID NO: 8; SEQ ID NO: 16; SEQ ID NO: 12; and SEQ ID NO: 20.

The present disclosure also provides a vector comprising the polynucleotide as described herein.

The present disclosure also provides a host cell comprising the vector as described herein.

The present disclosure also provides an in vitro detection kit comprising the isolated antibody or antigen binding fragment thereof as described herein.

In some aspects, the kit further comprises a second antibody or antigen binding fragment thereof labeled with a radioactive, enzymatic and/or fluorescent group.

The present disclosure further provides a method for detecting the presence of AAVrh74 capsid protein in a sample, comprising contacting the sample with a composition comprising the antibody or antigen binding fragment thereof as described herein.

In some aspects, the presence of AAVrh74 capsid protein in the sample is indicated by detecting the presence of the antibody or antigen binding fragment thereof.

In some aspects, the presence of the antibody or antigen binding fragment thereof is detected by an immunoassay.

In some aspects, the immunoassay comprises one or more of an immunofluorescence assay, an immunohistochemical assay, a Western blot, a direct enzyme-linked immunosorbent assay (ELISA), an indirect ELISA, a sandwich ELISA, a competitive ELISA, a chemiluminescence assay, a radioimmunoassay, and an immunoprecipitation assay.

In some aspects, the method is less sensitive to detect AAV8 capsid protein and/or AAV9 capsid protein in the sample as compared to AAVrh74 capsid protein. In some aspects, the isolated antibody or antigen-binding fragment thereof specifically binds AAVrh74 capsid protein but does not bind AAV8 capsid protein and/or AAV9 capsid protein in the sample The present disclosure also provides a method of making an anti-AAV antibody or antigen binding fragment thereof, comprising (a) administering to a non-human vertebrate animal an immunogenic amount of a polypeptide comprising the amino acid sequence QGAGKDNVDYSS (SEQ ID NO: 45); (b) recovering spleen cells from the animal; (c) fusing the recovered spleen cells with myeloma cells to generate hybridomas; (d) screening the hybridomas for hybridomas that produce an antibody that specifically binds AAV capsid protein; and (e) recovering the antibody. In another embodiment, the capsid protein is an AAVrh74 capsid protein. In one embodiment, the antibody is an anti-AAV antibody.

In some aspects, the non-human vertebrate animal is a transgenic animal, and wherein the transgenic animal expresses human immunoglobulin genes.

In some aspects, the method further comprises administering to the non-human vertebrate animal one or more immune adjuvants.

In some aspects, the non-human vertebrate animal is selected from a mouse, rat, hamster, guinea pig, rabbit, chicken, non-human primate, pig, goat, cow, and horse.

In some aspects, the antibody or antigen binding fragment thereof specifically binds AAVrh74 capsid protein with more affinity as compared to other serotype o AAV capsids, e.g., AAV8 capsid protein and/or AAV9 capsid protein.

The present disclosure also provides a method of making an anti-AAV antibody or antigen binding fragment thereof, comprising (a) immobilizing on a solid support an antigen comprising the amino acid sequence QGAGKDNVDYSS (SEQ ID NO: 45); (b) applying a phage display antibody library to the immobilized antigen; (c) screening the library for phage that bind the antigen; and (d) recovering antigen-binding phage. In another embodiment, the capsid protein is an AAVrh74 capsid protein. In one embodiment, the antibody is an anti-AAV antibody.

In some aspects, the solid support is selected from the group consisting of a microtiter plate well, polyvinylidene fluoride (PVDF) membrane, column matrix, immunotube, and magnetic bead.

In some aspects, the phage display antibody library is derived from a non-human vertebrate animal previously immunized with a composition comprising an immunogenic amount of a polypeptide comprising the amino acid sequence QGAGKDNVDYSS (SEQ ID NO: 45).

In some aspects, the non-human vertebrate animal is selected from a mouse, rat, hamster, guinea pig, rabbit, chicken, non-human primate, pig, goat, cow, and horse.

In some aspects, the antibody or antigen binding fragment thereof specifically binds AAVrh74 capsid protein but does not bind AAV8 capsid protein and/or AAV9 capsid protein.

The present disclosure also provides an in silico method of making an anti-AAVrh74 antibody or antigen binding fragment thereof, comprising (a) designing CDRs in silico that specifically bind to an epitope on AAV capsid protein; (b) grafting the CDRs onto single-chain variable fragments (scFvs); (c) screening the scFvs for binding to a target polypeptide using antibody phage display; and (d) selecting scFvs that bind to the target polypeptide, wherein the epitope on AAV capsid protein and the target polypeptide each comprises the amino acid sequence QGAGKDNVDYSS (SEQ ID NO: 45). In another embodiment, the capsid protein is an AAVrh74 capsid protein. In one embodiment, the antibody is an anti-AAV antibody.

In some aspects, the antibody or antigen binding fragment thereof specifically binds AAVrh74 capsid protein with more affinity as compared to AAV8 capsid protein and/or AAV9 capsid protein.

BRIEF DESCRIPTION OF THE DRAWINGS/FIGURES

Figure 3A:
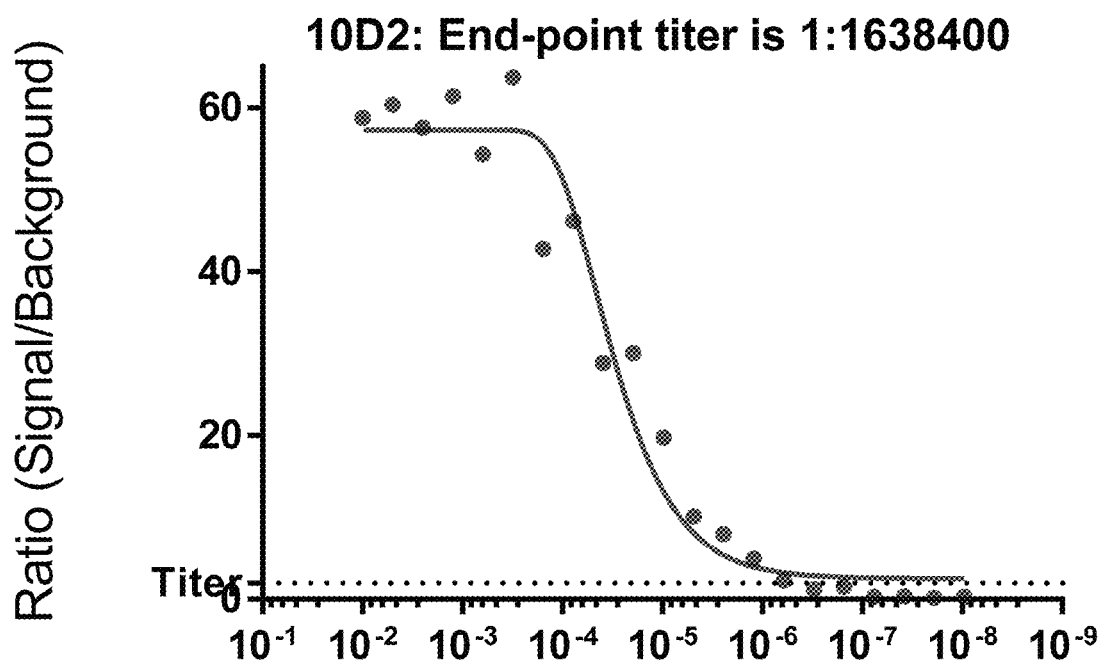
Figure 3B:
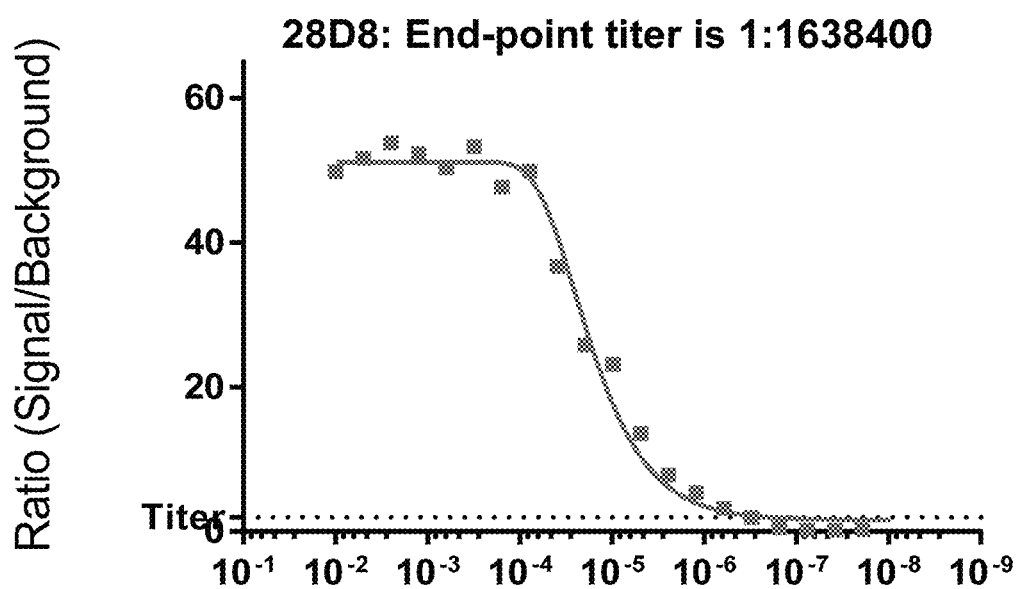
Figure 3C:
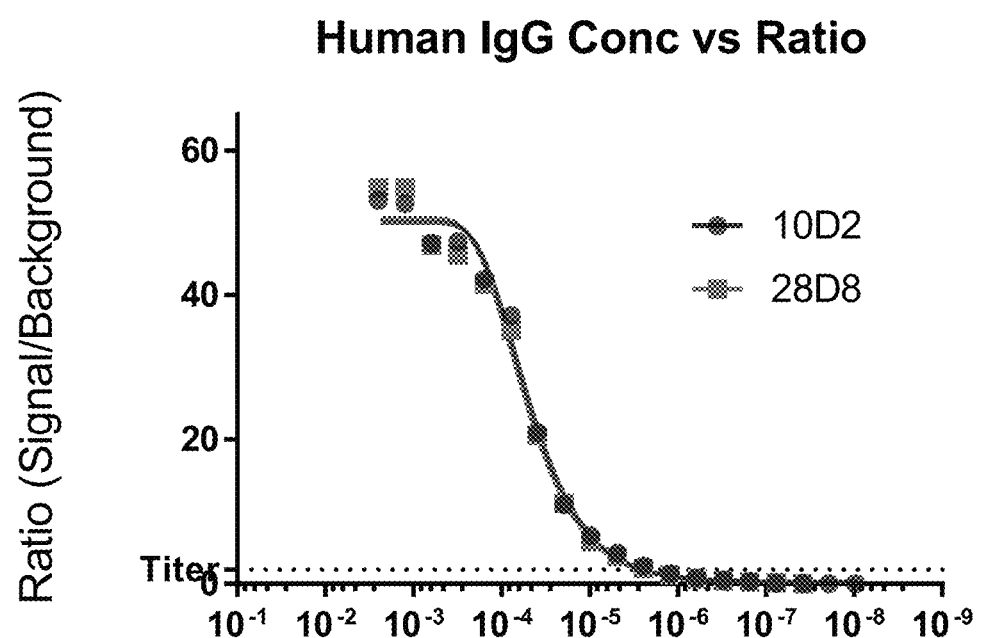

FIGS. 3A-3C show ELISA data for a titration curve of chimeric IgG1 10D2 AAVrh74 antibody and chimeric IgG 28D8 AAVrh74 antibody binding to AAVrh74. FIG. 3A shows ELISA data for a titration curve of chimeric IgG1 10D2. FIG. 3B shows ELISA data for a titration curve of chimeric IgG1 28D8. FIG. 3C shows a graph of an overlay of the titration curves for chimeric IgG 10D2 and chimeric IgG1 28D8.

Figure 4A:
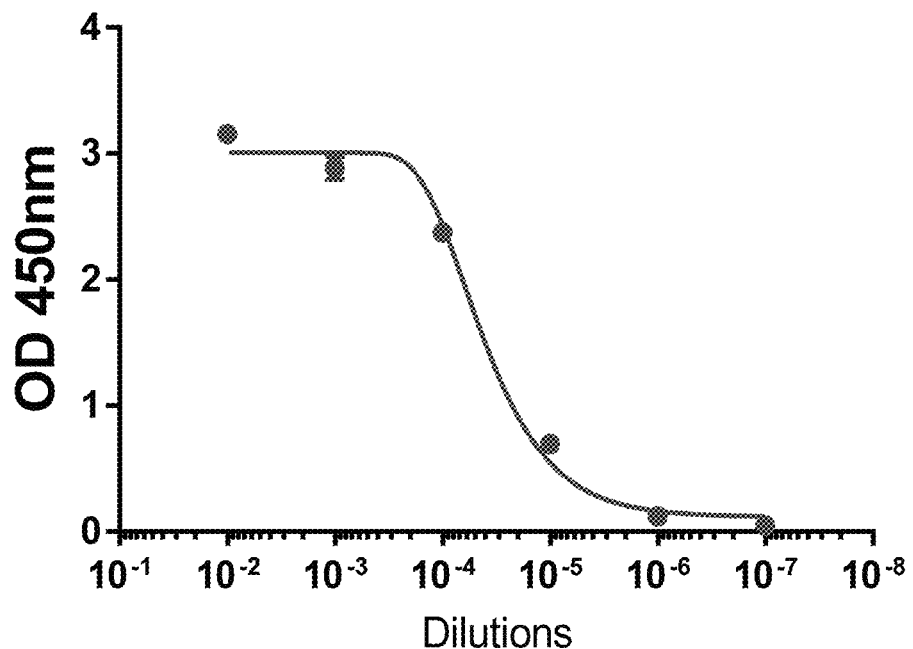
Figure 4B:
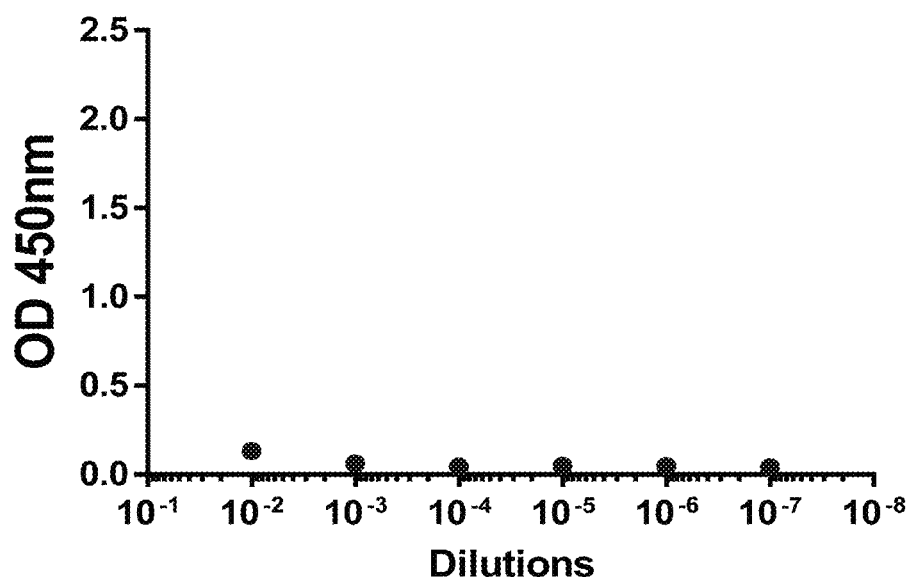
Figure 4C:
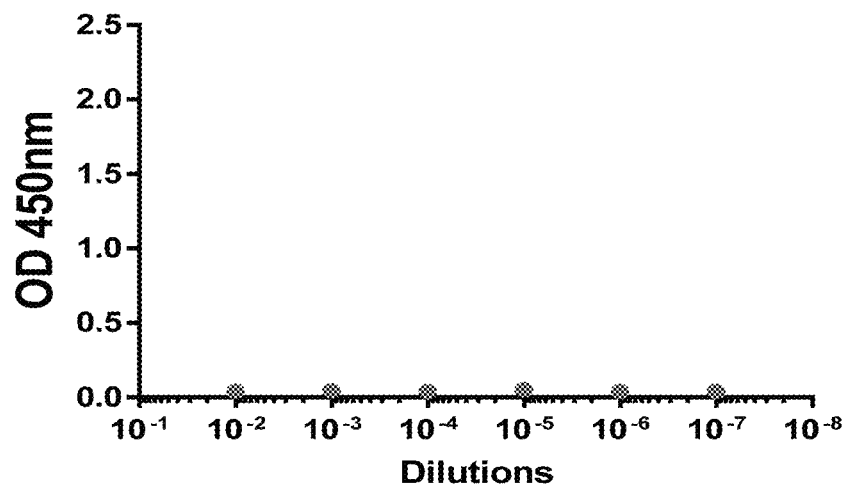
Figure 4D:
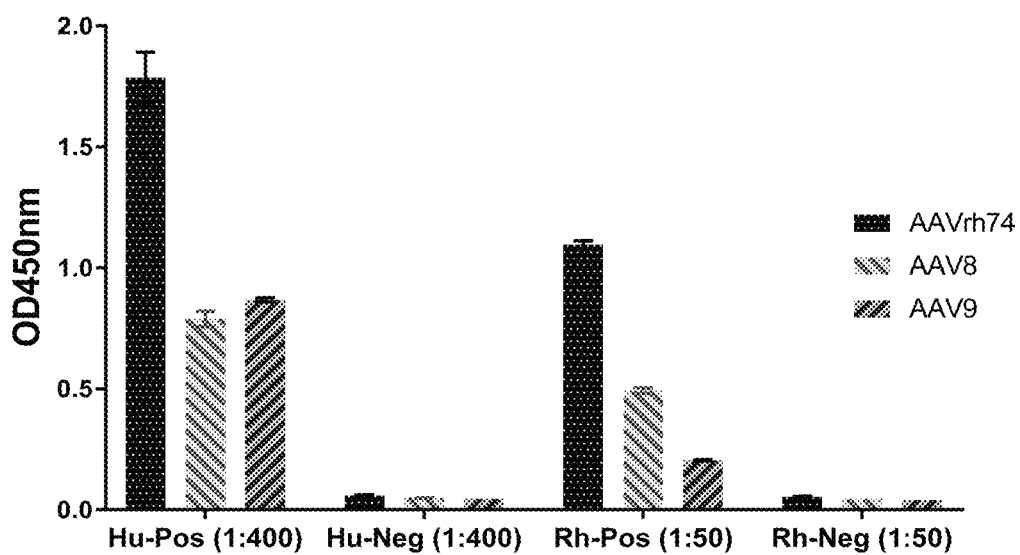

FIGS. 4A-4D show ELISA data for titration curves of chimeric IgG1 10D2 AAVrh74 antibody binding to AAVrh74 but with little or no binding to AAV8 and/or AAV9. FIG. 4A shows ELISA data for a titration curve of chimeric IgG1 10D2 binding to AAVrh74. FIG. 4B shows ELISA data for a titration curve of chimeric IgG1 10D2 binding to AAV8. FIG. 4C shows ELISA data for a titration curve of chimeric IgG1 10D2 binding to AAV9. FIG. 4D shows ELISA data of positive and negative controls.

Figure 5A:
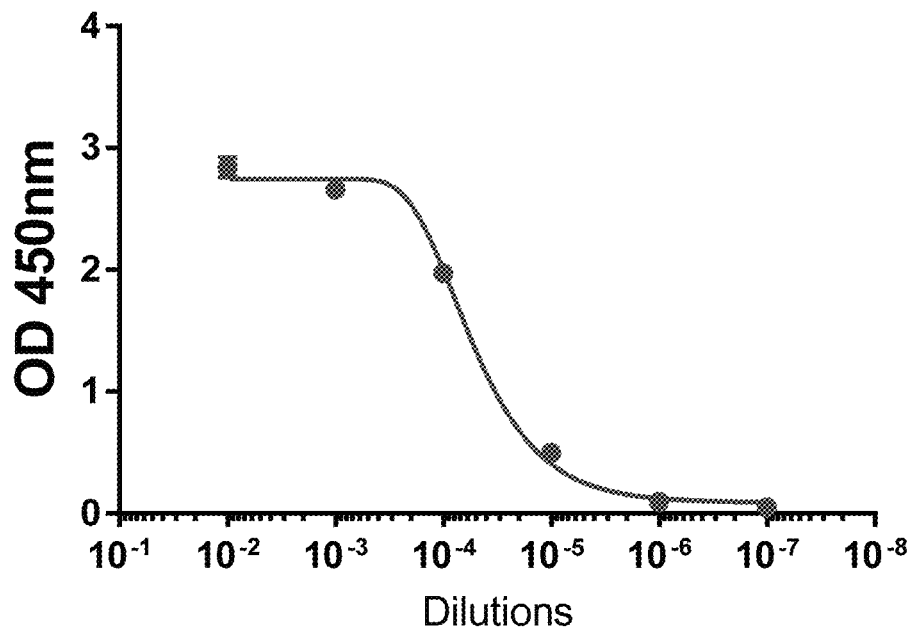
Figure 5B:
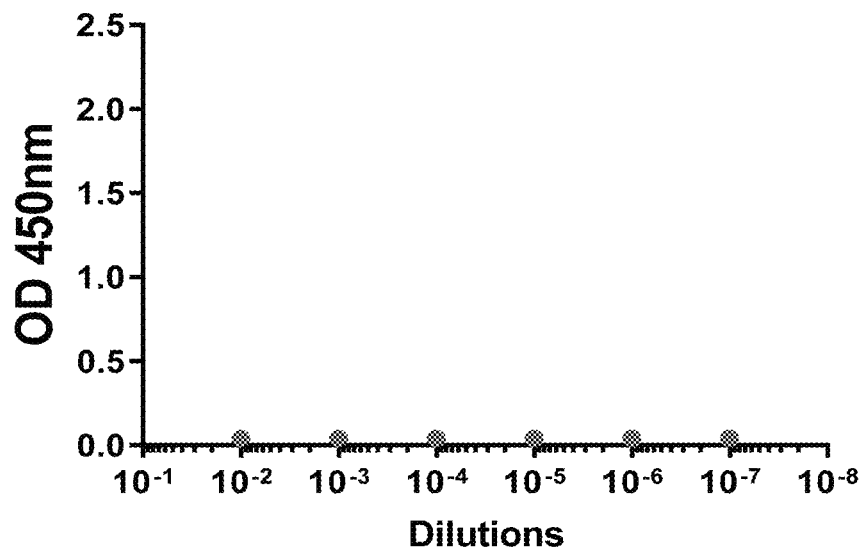
Figure 5C:
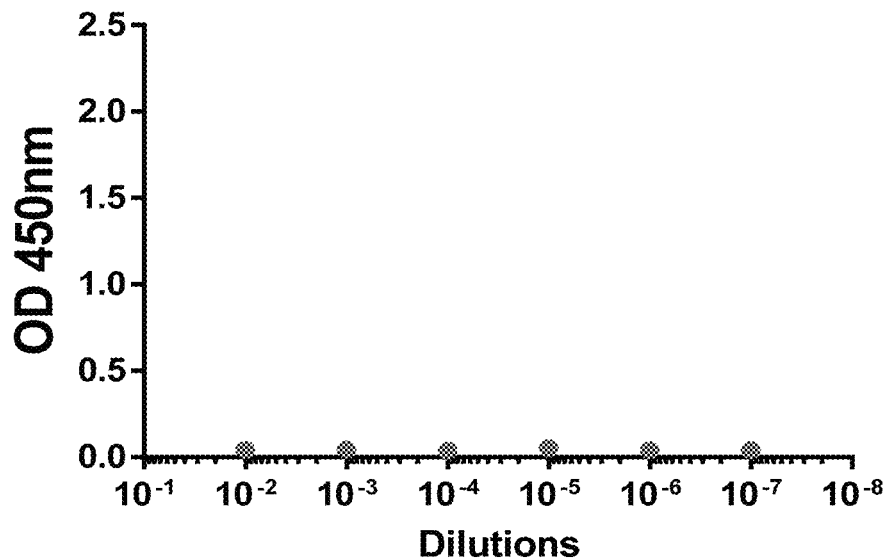
Figure 5D:
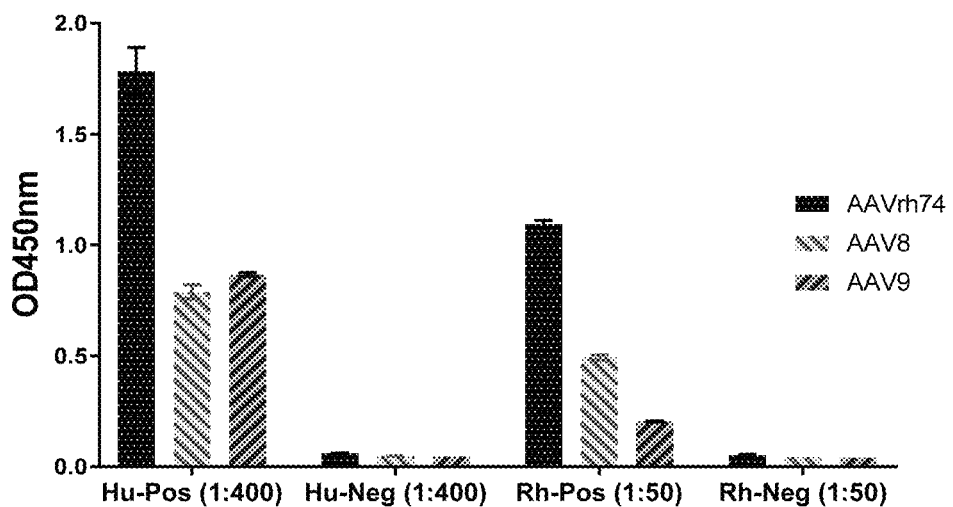

FIGS. 5A-5D show ELISA data for titration curves of chimeric IgG1 28D8 AAVrh74 antibody binding to AAVrh74 but with little or no binding to AAV8 or AAV9. FIG. 5A shows ELISA data for a titration curve of chimeric IgG1 28D8 binding to AAVrh74. FIG. 5B shows ELISA data for a titration curve of chimeric IgG1 28D8 binding to AAV8. FIG. 5C shows ELISA data for a titration curve of chimeric IgG1 28D8 binding to AAV9. FIG. 5D shows ELISA data of positive and negative controls.

Figure 6A:
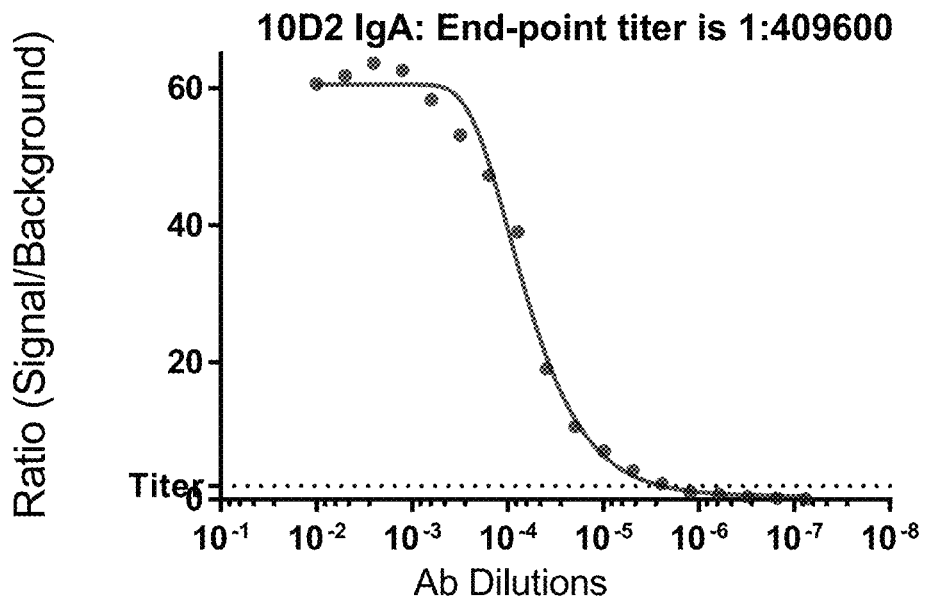
Figure 6B:
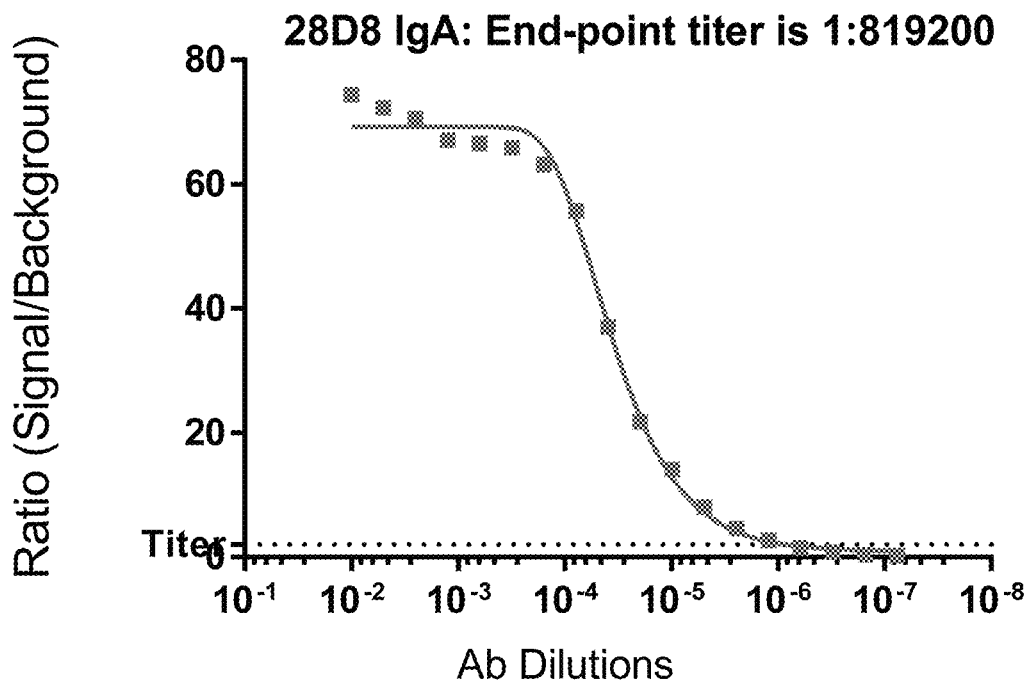
Figure 6C:
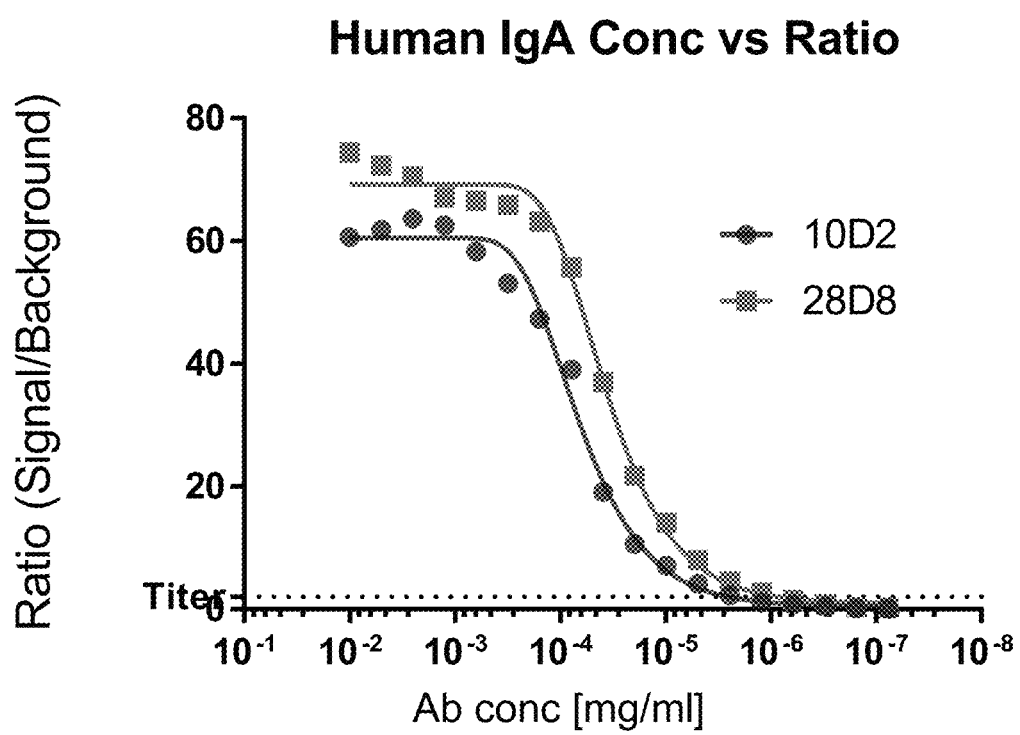

FIGS. 6A-6C show ELISA data for a titration curve of chimeric IgA 10D2 AAVrh74 antibody and chimeric IgA 28D8 AAVrh74 antibody binding to AAVrh74. FIG. 6A shows ELISA data for a titration curve of chimeric IgA 10D2. FIG. 6B shows ELISA data for a titration curve of chimeric IgA 28D8. FIG. 6C shows a graph of an overlay of the titration curves for chimeric IgA 10D2 and chimeric IgA 28D8.

Figure 7A:
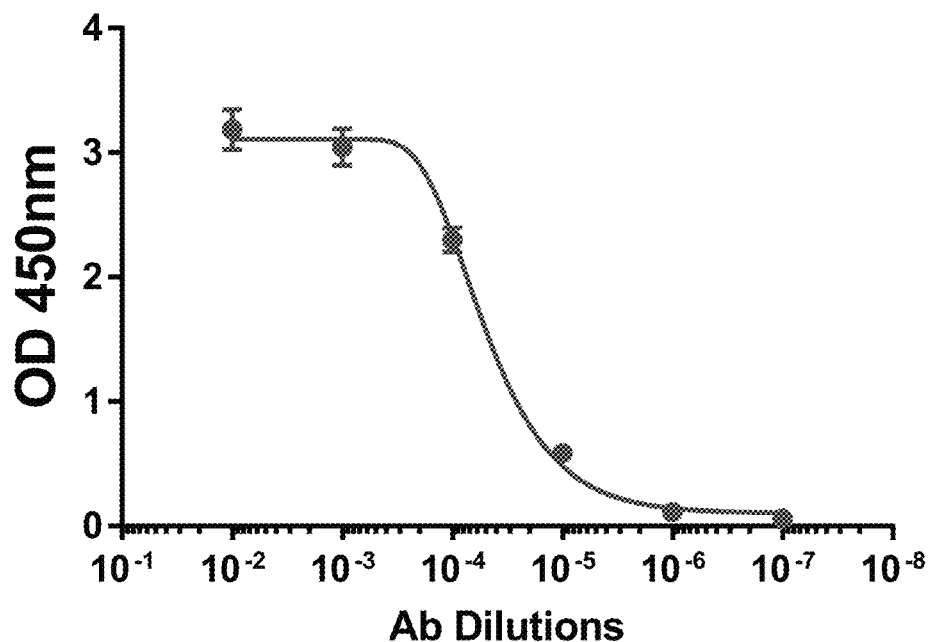
Figure 7B:
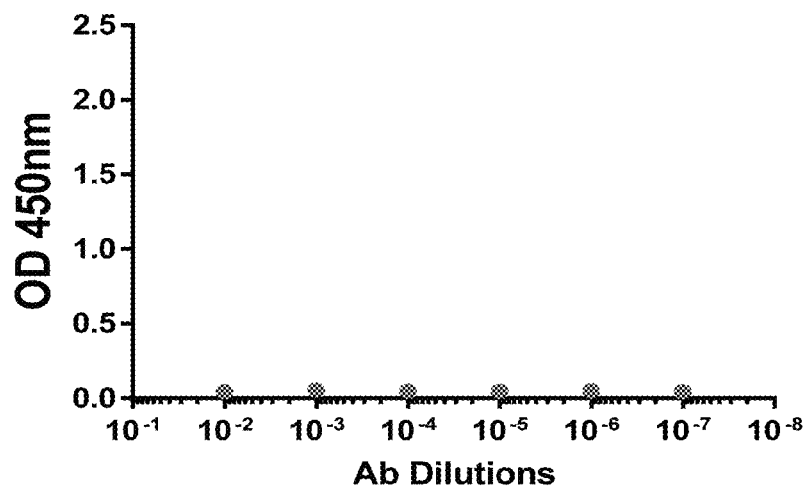
Figure 7C:
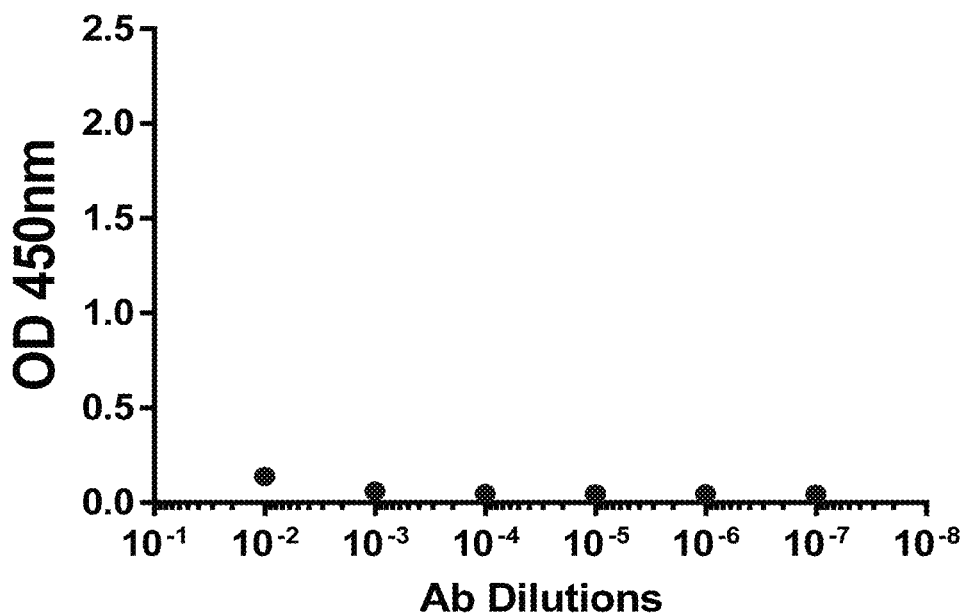
Figure 7D:
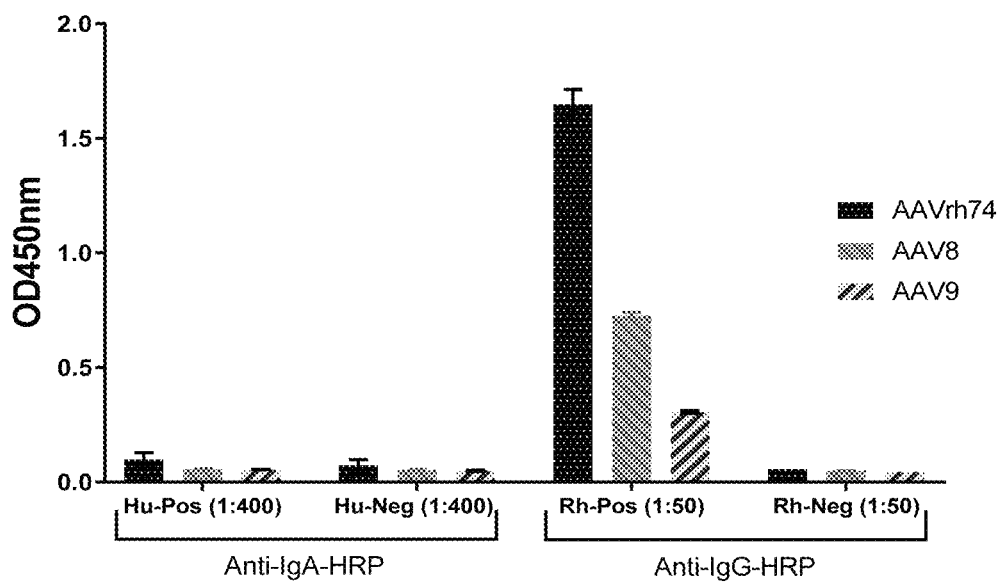

FIGS. 7A-7D show ELISA data for titration curves of chimeric IgA 10D2 AAVrh74 antibody binding to AAVrh74 but with little or no binding to AAV8 or AAV9. FIG. 7A shows ELISA data for a titration curve of chimeric IgA 10D2 binding to AAVrh74. FIG. 7B shows ELISA data for a titration curve of chimeric IgA 10D2 binding to AAV8. FIG. 7C shows ELISA data for a titration curve of chimeric IgA 10D2 binding to AAV9. FIG. 7D shows ELISA data for positive and negative controls.

Figure 8A:
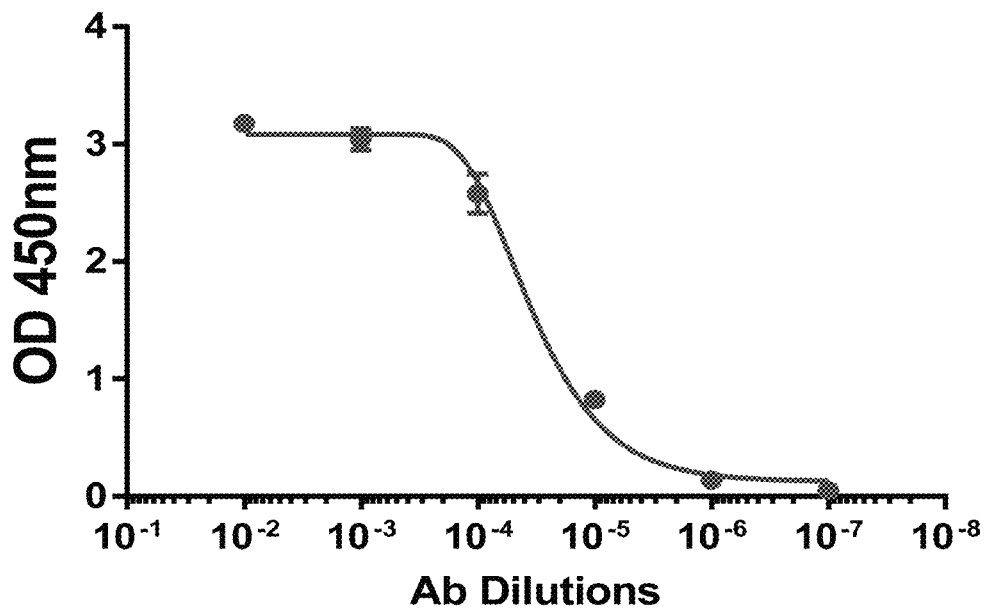
Figure 8B:
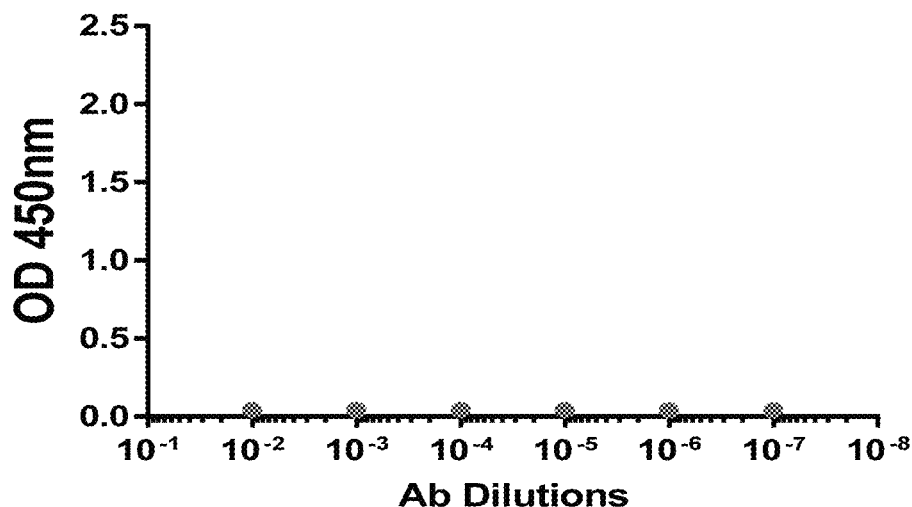
Figure 8C:
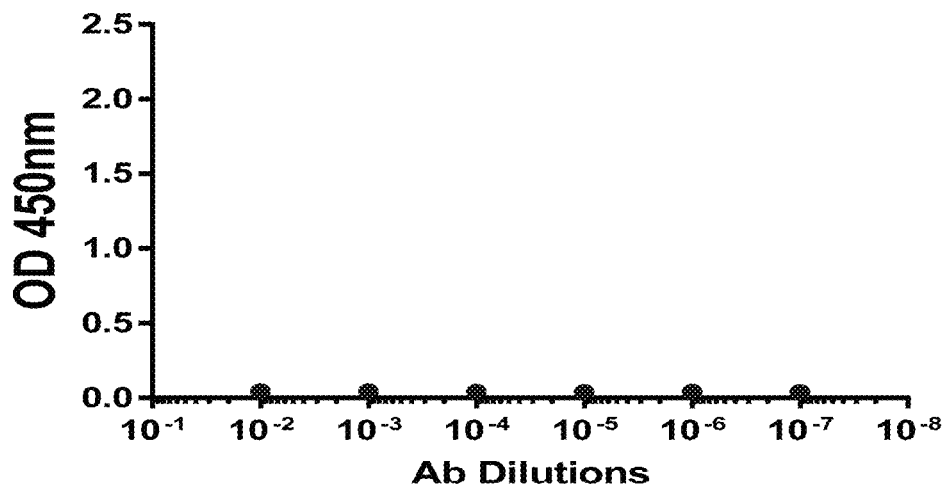
Figure 8D:
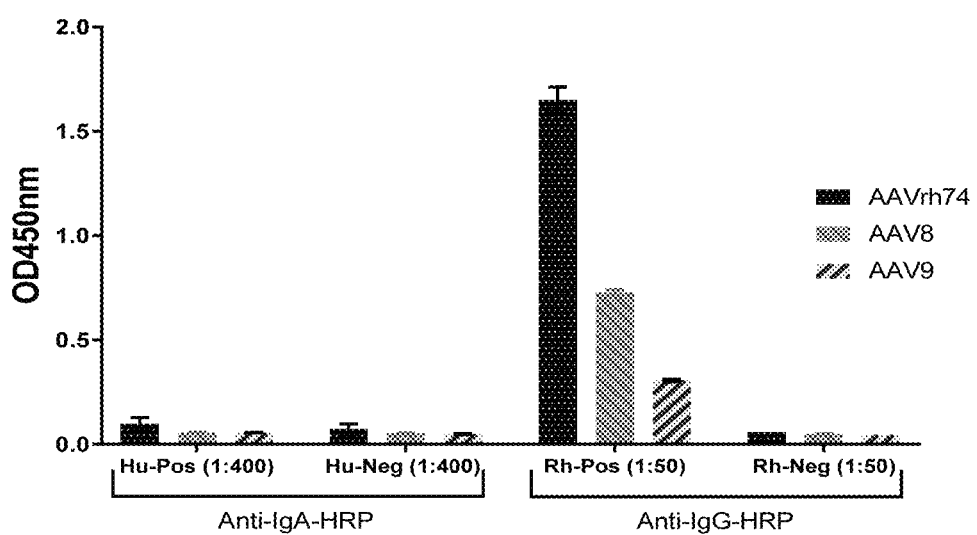

FIGS. 8A-8D show ELISA data for titration curves of chimeric IgA 28D8 AAVrh74 antibody binding to AAVrh74 but with little or no binding to AAV8 or AAV9. FIG. 8A shows ELISA data for a titration curve of chimeric IgA 28D8 binding to AAVrh74. FIG. 8B shows ELISA data for a titration curve of chimeric IgA 28D8 binding to AAV8. FIG. 8C shows ELISA data for a titration curve of chimeric IgA 28D8 binding to AAV9. FIG. 8D shows ELISA data for positive and negative controls.

Figure 9A:
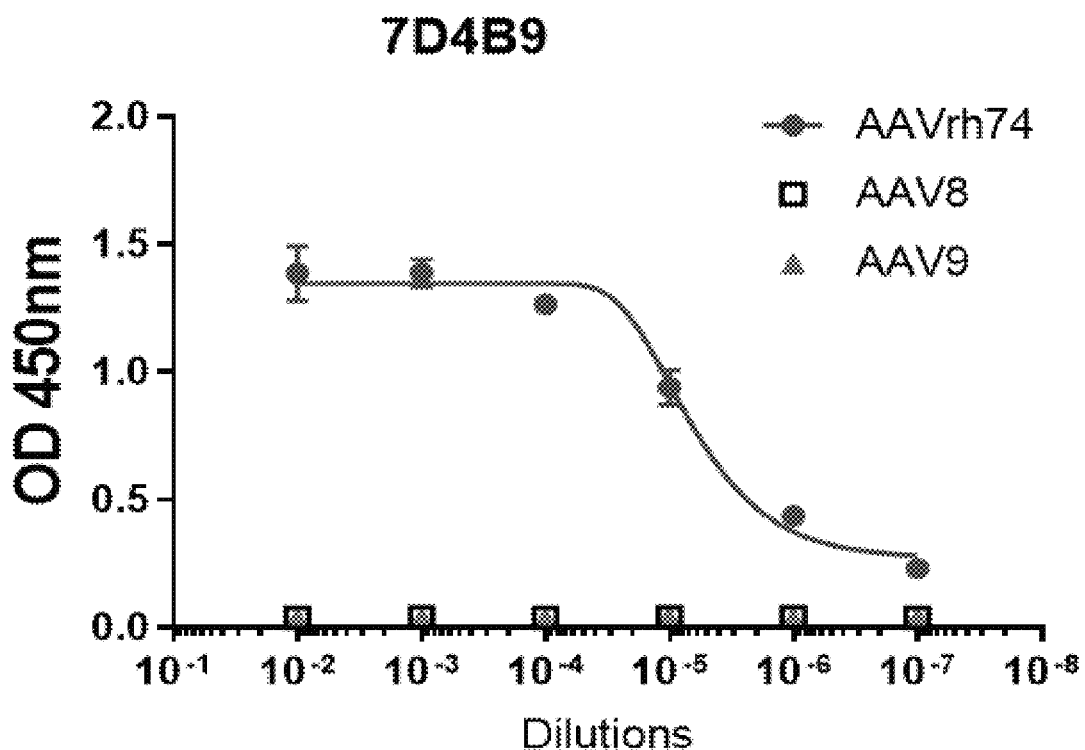
Figure 9B:
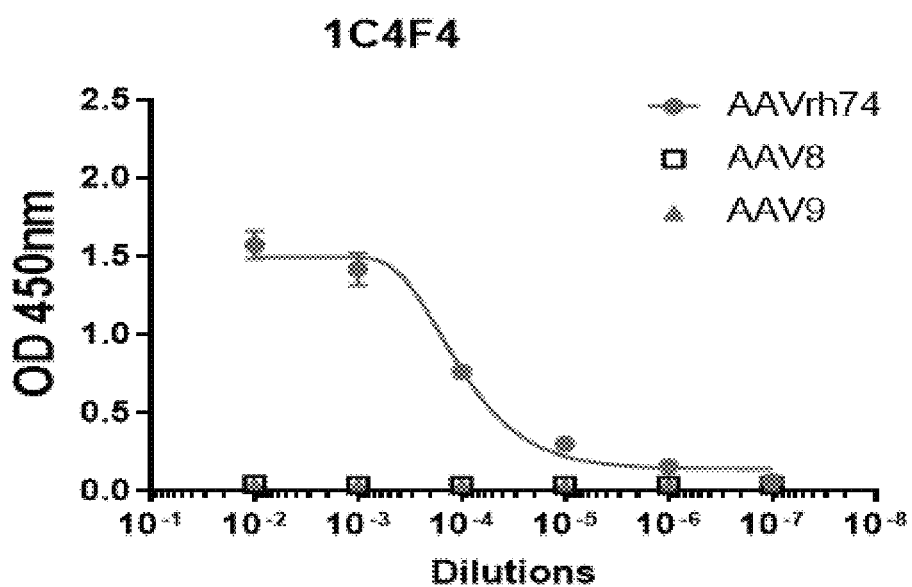
Figure 9C:
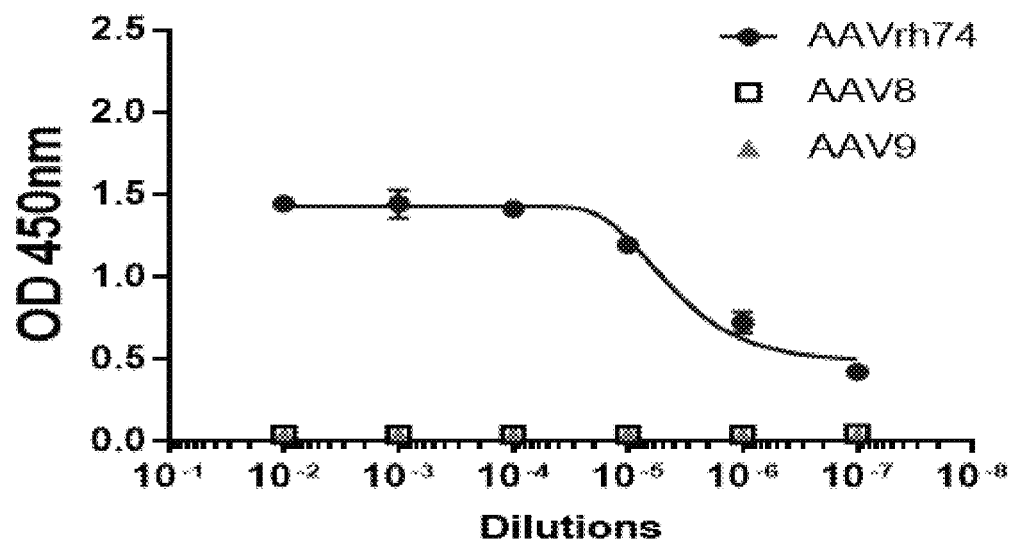
Figure 9D:
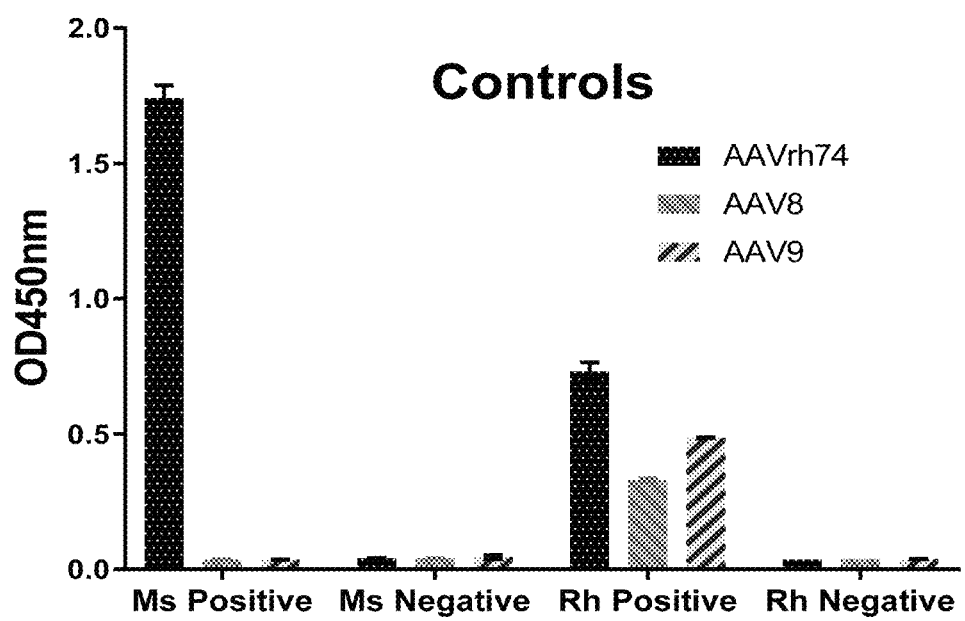
Figure 9E:
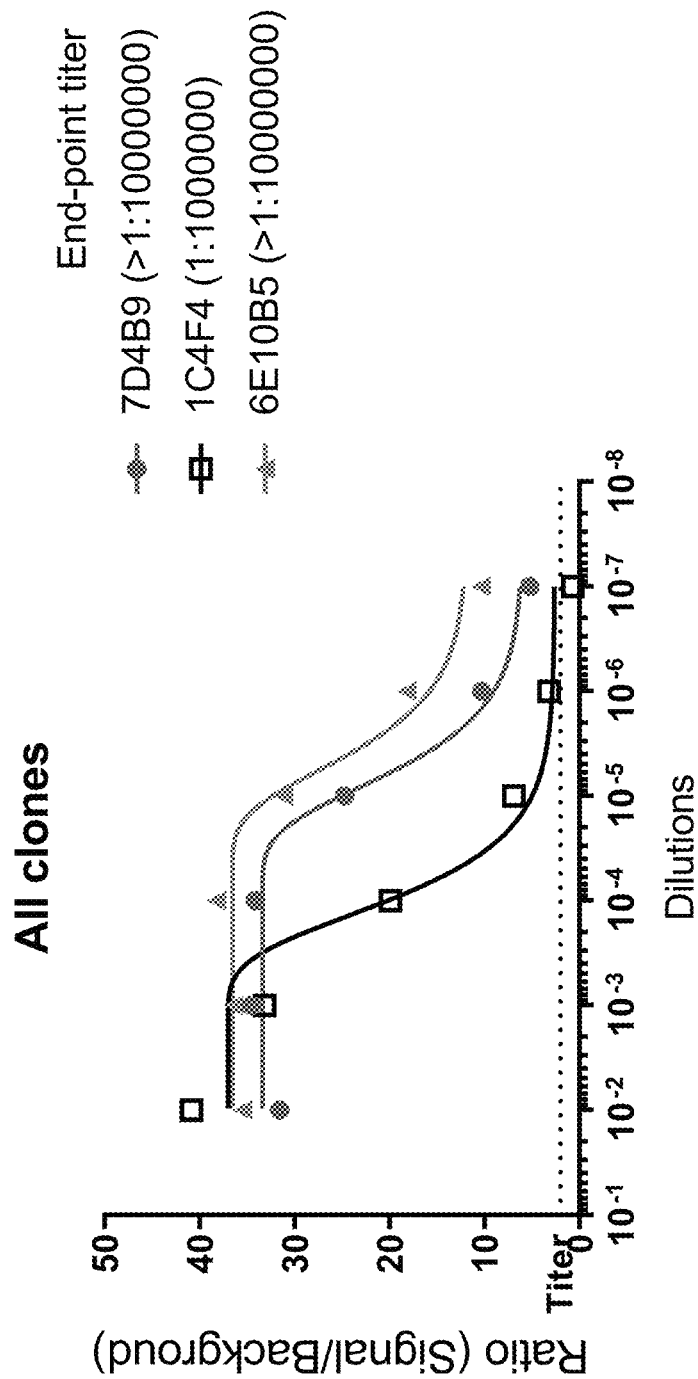

FIGS. 9A-9E show ELISA data for titration curves of monoclonal antibodies 7D4B9, 1C4F4, and 6E10B5 binding to AAVrh74 with a much higher affinity compared to AAV8 or AAV9. FIG. 9A shows titration curve and cross-reactivity for 7D4B9. FIG. 9B shows titration curve and cross-reactivity for 1C4F4. FIG. 9C shows titration curve and cross-reactivity for 6E10B5. FIG. 9D shows the data for the positive and negative controls used in the assay. FIG. 9E shows an overlay of the titration curves for 7D4B9, 1C4F4, and 6E10B5. All three antibodies show serotype specific binding to AAVrh74 with comparably less cross-reactivities with AAV8 and/or AAV9.

DETAILED DESCRIPTION

Unless defined otherwise, all technical and scientific terms used herein have the same meaning as commonly understood by one of ordinary skill in the art to which this disclosure belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Throughout this disclosure, the term "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

As used herein, "antibody" means an intact immunoglobulin, an antigen-binding fragment thereof, or an antigen-binding molecule. Antibodies of this disclosure can be of any isotype or class (e.g., IgM, IgD, IgG, IgE and IgA) or any subclass (e.g., IgG1-4, IgA1-2) or any type of subclass (e.g., IgG2a, IgG2b) and can have either a kappa (κ) or lambda (λ) light chain. An antigen-binding fragment of an antibody includes, e.g., Fab, Fv, scFv, and Fd fragments, chimeric antibodies, humanized antibodies, single-chain antibodies (scAb), single domain antibodies (dAb), single domain heavy chain antibodies, a single domain light chain antibodies, bi-specific antibodies, multi-specific antibodies, and fusion proteins comprising an antigen-binding portion of an antibody and a non-antibody protein. The antibodies of the disclosure can be labelled with, e.g., a radioactive, enzymatic, or fluorescent group. The antibodies of the disclosure can also be conjugated to other moieties, such as members of specific binding pairs, e.g., biotin (member of biotin-avidin specific binding pair). The antibodies of the disclosure can also be bound to a solid support, such as, e.g., polystyrene plates or beads, and the like.

As used herein, a "monoclonal antibody" is an antibody produced by a group of identical cells, all of which were produced from a single cell by repetitive cellular replication. That is, the clone of cells only produces a single antibody species. A monoclonal antibody can be produced using hybridoma production technology or using other production methods known to those skilled in the art, including e.g., antibody phage display libraries.

As used herein, the term "heavy chain" refers to an antibody heavy chain, consisting of a variable region and a constant region. As used herein, the term "light chain" refers to an antibody light chain, consisting of a variable region and a constant region.

The term "full-length antibody" denotes an antibody including two full-length antibody heavy chains and two full-length antibody light chains. For example, a full-length IgG antibody heavy chain is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH—CH—HR—CH2-CH3. A full-length antibody light chain is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ, (lambda). The two full-length antibody domains are linked together via inter-polypeptide disulphide bonds between the CL domain and the CH1 domain and between the hinge regions of the full-length antibody heavy chains. Full-length antibodies can be any isotype or class (e.g., IgM, IgD, IgG, IgE and IgA) or any subclass (e.g., IgG1-4, IgA1-2) or any type of subclass (e.g., IgG2a, IgG2b).

As used herein and mentioned above, the term "capsid" or "capsid protein" refers to the proteinaceous shell or coat of a viral particle. Capsids function to encapsidate, protect, transport, and release into host cell a viral genome. Capsids are generally comprised of oligomeric structural subunits of protein ("capsid proteins"), e.g., VP1, VP2, and VP3. As used herein, the term "encapsidated" means enclosed within a viral capsid. For example, AAVrh74 capsid sequence is disclosed in U.S. Pat. No. 9,434,928, the content of which is incorporated by reference in its entirety.

As used herein and mentioned above, "complementarity determining region(s)" ("CDR") describe the non-contiguous antigen combining sites (also known as antigen binding regions) found within the variable region of both heavy and light chain polypeptides. This particular region has been described by Kabat et al., J. Biol. Chem. 252:6609-6616 (1977); Kabat et al., U.S. Dept. of Health and Human Services, "Sequences of proteins of immunological interest" (1991) (also referred to herein as Kabat 1991); by Chothia et al., J. Mol. Biol. 196:901-917 (1987) (also referred to herein as Chothia 1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody. As used herein the term the terms "CDRL1", "CDRL2", and "CDRL3" refer to the first, second, and third CDRs in a light chain variable region, respectively. As used herein, the terms "CDRH1", "CDRH2", and "CDRH3" refer to the first, second, and third CDRs in a heavy chain variable region, respectively.

An "isolated" antibody is one that has been identified and separated and/or recovered from a component of its natural environment. In some aspects, the term "isolated" is used interchangeably with the term "recombinant." As used herein, the terms "isolated" and "recombinant" refer to polypeptides or nucleotides formed by laboratory methods, such as molecular cloning. In some aspects, the antibody will be purified (a) to greater than 90%, greater than 95%, or greater than 98%, by weight of antibody as determined by the Lowry method, for example, more than 99% by weight, (b) to a degree sufficient to obtain at least 15 residues of N-terminal or internal amino acid sequence by use of a spinning cup sequenator, or (c) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some aspects, isolated antibody will be prepared by at least one purification step.

The term "percent (%) identity" as used herein is defined as the percentage of nucleotide or amino acid residues in a sequence that are identical with the nucleotide or amino acid residues of the reference sequence after aligning the sequences and introducing gaps, if necessary, to achieve the maximum percent sequence identity. For example, the percent (%) amino acid sequence identity of an antibody refers to an antibody sequence that are identical with the amino acid residues in the reference antibody sequence, after aligning the sequences and introducing gaps, if necessary, to achieve the maximum percent sequence identity, and not considering any conservative substitutions as part of the sequence identity. Alignment for purposes of determining percent identity can be achieved in various ways that are within the skill in the art, for instance, using publicly available computer software such as BLAST, BLAST-2, Clustal W, Megalign (DNASTAR) software or the FASTA program package. In one embodiment, a sequence comparison is performed using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at ebi.ac.uk/Tools/psa. Those skilled in the art can determine appropriate parameters for aligning sequences, including any algorithms needed to achieve maximal alignment over the full length of the sequences being compared.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from clustal.org. Another suitable program is MUSCLE, available from drive5.com/muscle/. ClustalW2 and MUSCLE are alternatively available, e.g., from the EBI.

As used herein, the term "80%, 81%, 82%, 83%, 84%, 85%, 86%, 87%, 88%, 89%, 90%, 91%, 92%, 93%, 94%, 95%, 96%, 97%, 98%, 99%, or 100% identity" as used in the disclosure means that all such sequences are either of at least about 80% identity, at least about 81% identify, at least about 82% identity, at least about 83% identity, at least about 84% identity, at least about 85% identity, at least about 86% identity, at least about 87% identity, at least about 88% identity, at least about 89% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, or 100% identity (fully identical).

The term "epitope" refers to a region of an antigen that is bound by an antibody. An epitope may be defined as structural or functional. Functional epitopes are generally a subset of structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "binding" refers to a direct association between two molecules, due to, for example, covalent, electrostatic, hydrophobic, and ionic and/or hydrogen-bond interactions, including interactions such as salt bridges and water bridges. A subject anti-AAV antibody binds specifically to an epitope within AAVrh74 capsid protein.

The term "murine antibody" as used herein includes antibodies in which the variable region sequences and the constant region sequences are derived from a mouse.

The term "chimeric antibody" as used herein includes antibodies in which the variable region sequences are derived from one species and the constant region sequences are derived from another species, such as an antibody in which the variable region sequences are derived from a mouse antibody and the constant region sequences are derived from a human antibody.

The term "humanized antibody" as used herein includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The term "human antibody" as used herein means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc. Preferably the subject is human.

Anti-AAVrh74 Antibodies

The present disclosure provides an isolated anti-AAV (adeno-associated virus) antibody or an antigen-binding fragment thereof capable of specifically binding an epitope of AAVrh74 capsid protein or a recombinant AAV vector with an AAVrh74 capsid protein. In particular aspects, the epitope within AAVrh74 capsid protein comprises an amino acid sequence having at least about 90%, about 91%, about 92%, about 93%, about 94%, about 95%, about 96%, about 97%, about 98%, about 99%, or 100% identity to the amino acid sequence QGAGKDNVDYSS (SEQ ID NO: 45) or a portion thereof. In some aspects, the amino acid sequence of the epitope within AAVrh74 capsid protein is QGAGKDNVDYSS (SEQ ID NO: 45).

In some aspects, the present disclosure provides an isolated anti-AAV antibody or antigen binding fragment thereof that specifically binds an epitope within AAVrh74 capsid protein, wherein the antibody competes for binding the epitope with a reference antibody. Competing antibodies or antigen-binding fragments thereof can be identified, for example, by using an antibody competition assay. Details of procedures for carrying out such competition assays are well known in the art and can be found, for example, in Harlow and Lane (1988) Antibodies, A Laboratory Manual, Cold Spring Harbor Laboratory Press, Cold Spring Harbor, N.Y., pages 567-569. For purposes of the present disclosure, anti-AAVrh74 antibodies or fragments thereof that compete with a reference antibody are those that decrease the binding of the reference antibody to the target polypeptide by at least about 50%, about 60%, about 70%, about 75%, about 80%, about 85%, about 90%, about 95%, or about 99%.

In some aspects, the heavy chain variable region of the reference antibody comprises an amino acid sequence selected from the group consisting of: SEQ ID NO: 1, SEQ ID NO: 5, SEQ ID NO: 13, SEQ ID NO: 9, and SEQ ID NO: 17. In some aspects, the light chain variable region of the reference antibody comprises an amino acid sequence selected from the group consisting of: SEQ ID NO: 2, SEQ ID NO: 6, SEQ ID NO: 14, SEQ ID NO: 10, and SEQ ID NO: 18. In some aspects, the heavy chain variable region of the reference antibody comprises an amino acid sequence selected from the group consisting of: SEQ ID NO: 1, SEQ ID NO: 5, SEQ ID NO: 13, SEQ ID NO: 9, and SEQ ID NO: 17; and the light chain variable region of the reference antibody comprises an amino acid sequence selected from the group consisting of: SEQ ID NO: 2, SEQ ID NO: 6, SEQ ID NO: 14, SEQ ID NO: 10, and SEQ ID NO: 18.

In a particular aspect, the heavy chain variable region of the reference antibody comprises the amino acid sequence set forth in SEQ ID NO: 1 and the light chain variable region of the reference antibody comprises the amino acid sequence set forth in SEQ ID NO: 2. In another aspect, the heavy chain variable region of the reference antibody comprises the amino acid sequence set forth in SEQ ID NO: 5 and the light chain variable region of the reference antibody comprises the amino acid sequence set forth in SEQ ID NO: 6. In another aspect, the heavy chain variable region of the reference antibody comprises the amino acid sequence set forth in SEQ ID NO: 13 and the light chain variable region of the reference antibody comprises the amino acid sequence set forth in SEQ ID NO: 14. In another aspect, the heavy chain variable region of the reference antibody comprises the amino acid sequence set forth in SEQ ID NO: 9 and the light chain variable region of the reference antibody comprises the amino acid sequence set forth in SEQ ID NO: 10. In another aspect, the heavy chain variable region of the reference antibody comprises the amino acid sequence set forth in SEQ ID NO: 17 and the light chain variable region of the reference antibody comprises the amino acid sequence set forth in SEQ ID NO: 18.

The present disclosure further provides an isolated anti-AAV antibody or antigen-binding fragment thereof that binds the same epitope within AAVrh74 capsid protein as a reference antibody. Assays for identifying antibodies that bind the same epitope within a particular protein are known to those of skill in the art. For example, such assays are detailed in Harlow and Lane (1988) Antibodies, A Laboratory Manual, Cold Spring Harbor Laboratory Press, Cold Spring Harbor, N.Y., Chapter 14.

In some aspects, the heavy chain variable region of the reference antibody comprises an amino acid sequence selected from the group consisting of: SEQ ID NO: 1, SEQ ID NO: 5, SEQ ID NO: 13, SEQ ID NO: 9, and SEQ ID NO: 17. In some aspects, the light chain variable region of the reference antibody comprises an amino acid sequence selected from the group consisting of: SEQ ID NO: 2, SEQ ID NO: 6, SEQ ID NO: 14, SEQ ID NO: 10, and SEQ ID NO: 18. In some aspects, the heavy chain variable region of the reference antibody comprises an amino acid sequence selected from the group consisting of: SEQ ID NO: 1, SEQ ID NO: 5, SEQ ID NO: 13, SEQ ID NO: 9, and SEQ ID NO: 17; and the light chain variable region of the reference antibody comprises an amino acid sequence selected from the group consisting of: SEQ ID NO: 2, SEQ ID NO: 6, SEQ ID NO: 14, SEQ ID NO: 10, and SEQ ID NO: 18.

In a particular aspect, the heavy chain variable region of the reference antibody comprises the amino acid sequence set forth in SEQ ID NO: 1 and the light chain variable region of the reference antibody comprises the amino acid sequence set forth in SEQ ID NO: 2. In another aspect, the heavy chain variable region of the reference antibody comprises the amino acid sequence set forth in SEQ ID NO: 5 and the light chain variable region of the reference antibody comprises the amino acid sequence set forth in SEQ ID NO: 6. In another aspect, the heavy chain variable region of the reference antibody comprises the amino acid sequence set forth in SEQ ID NO: 13 and the light chain variable region of the reference antibody comprises the amino acid sequence set forth in SEQ ID NO: 14. In another aspect, the heavy chain variable region of the reference antibody comprises the amino acid sequence set forth in SEQ ID NO: 9 and the light chain variable region of the reference antibody comprises the amino acid sequence set forth in SEQ ID NO: 10. In another aspect, the heavy chain variable region of the reference antibody comprises the amino acid sequence set forth in SEQ ID NO: 17 and the light chain variable region of the reference antibody comprises the amino acid sequence set forth in SEQ ID NO: 18.

The isolated anti-AAVrh74 antibodies or antigen binding fragment thereof of the present disclosure specifically bind an epitope within AAVrh74 capsid protein. In one embodiment, the antibodies or antigen binding fragment thereof binds to VP1, VP2, and/or VP3 of the AAVrh74 capsid protein. In some embodiments, the isolated antibody or antigen binding fragment thereof has a higher affinity in binding AAVrh74 capsid as compared to AAV8 or AAV9 capsid. In some embodiments, the isolated antibody or antigen binding fragment thereof does not bind the capsid protein of AAV8. In some embodiments, the isolated antibody or antigen binding fragment thereof does not bind the capsid protein of AAV9. In some aspects, the isolated antibody or antigen binding fragment thereof does not bind AAV 8 and/or AAV9.

In some aspects of the disclosure, the heavy chain variable region of the isolated antibody or antigen binding fragment thereof comprises a VH CDR3 selected from the group consisting of GVAHYSDSRFAFDY (SEQ ID NO: 35), GNAHPGGSAFVY (SEQ ID NO: 41), RGSYYYDSSPAWFAY (SEQ ID NO: 48), RGVDSSGYGAFAY (SEQ ID NO: 54), and TRGTSTMISTFAFVY (SEQ ID NO: 60).

In some aspects, the heavy chain variable region of the isolated antibody or antigen binding fragment thereof comprises a VH CDR1 selected from the group consisting of NYGMN (SEQ ID NO: 33), DYGMN (SEQ ID NO: 39), YTFTNYGMN (SEQ ID NO: 46), YTFTKYGMN (SEQ ID NO: 52), and YTFTNYGMN (SEQ ID NO: 58).

In some aspects, the heavy chain variable region of the isolated antibody or antigen binding fragment thereof comprises a VH CDR2 selected from the group consisting of

```
                                    (SEQ ID NO: 34)
            WINTYTGEPTYADDFKG, (SEQ ID NO: 40)
            WINTNTGEPTYGDDFKG, (SEQ ID NO: 47)
            WMGWINTYTGEPTY, (SEQ ID NO: 53)
            WMGWINTYTGEPTY,
            and (SEQ ID NO: 59)
            WMGWINTYTGEPTY.
```

In some aspects, the a heavy chain variable region of the isolated antibody or antigen binding fragment thereof comprises a VH CDR3 having the amino acid sequence GVAHYSDSRFAFDY (SEQ ID NO: 35), a VH CDR1 having the amino acid sequence NYGMN (SEQ ID NO: 33), and a VH CDR2 having the amino acid sequence WINTYTGEPTYADDFKG (SEQ ID NO: 34).

In some aspects, the heavy chain variable region of the isolated antibody or antigen binding fragment thereof comprises a VH CDR3 having the amino acid sequence GNAHPGGSAFVY (SEQ ID NO: 41), a VH CDR1 having the amino acid sequence DYGMN (SEQ ID NO: 39), and a VH CDR 2 having the amino acid sequence WINTNTGEPTYGDDFKG (SEQ ID NO: 40).

In some aspects, the heavy chain variable region of the isolated antibody or antigen binding fragment thereof comprises a VH CDR3 having the amino acid sequence RGSYYYDSSPAWFAY (SEQ ID NO: 48), a VH CDR1 having the amino acid sequence YTFTNYGMN (SEQ ID NO: 46), and a VH CDR 2 having the amino acid sequence WMGWINTYTGEPT_(SEQ ID NO: 47).

In some aspects, the heavy chain variable region of the isolated antibody or antigen binding fragment thereof comprises a VH CDR3 having the amino acid sequence RGVDSSGYGAFAY (SEQ ID NO: 54), a VH CDR1 having the amino acid sequence YTFTKYGMN (SEQ ID NO: 52), and a VH CDR 2 having the amino acid sequence WMGWINTYTGEPTY (SEQ ID NO: 53).

In some aspects, the heavy chain variable region of the isolated antibody or antigen binding fragment thereof comprises a VH CDR3 having the amino acid sequence TRGTSTMISTFAFVY (SEQ ID NO: 60), a VH CDR1 having the amino acid sequence YTFTNYGMN (SEQ ID NO: 58), and a VH CDR 2 having the amino acid sequence WMGWINTYTGEPTY (SEQ ID NO: 59).

In some aspects of the disclosure, the light chain variable region of the isolated antibody or antigen binding fragment thereof comprises a VL CDR1 selected from the group consisting of SVSSSVSYMH (SEQ ID NO: 36), SASSGVTYMH (SEQ ID NO: 42), SSVSYMH (SEQ ID NO: 49), SSVSYMH (SEQ ID NO: 55), and SSVRYMH (SEQ ID NO: 61).

In some aspects, the light chain variable region of the isolated antibody or antigen binding fragment thereof comprises a VL CDR2 selected from the group consisting of YTSNLAS (SEQ ID NO: 37), RTSNLAS (SEQ ID NO: 43), LWIYSTSNLAS (SEQ ID NO: 50), LWIYSTSNLAS (SEQ ID NO: 56), and VWIYSTSNLAS (SEQ ID NO: 62).

In some aspects, the light chain variable region of the isolated antibody or antigen binding fragment thereof comprises a VL CDR3 selected from the group consisting of QQRSSYPFT (SEQ ID NO: 38), QQRSSYPFT (SEQ ID NO: 44), QQRSTYPF (SEQ ID NO: 51), QQRSFYPF (SEQ ID NO: 57), and QQRTYYPF (SEQ ID NO: 63).

In some aspects, the light chain variable region of the isolated antibody or antigen binding fragment thereof comprises a VL CDR1 having the amino acid sequence SVSSSVSYMH (SEQ ID NO: 36), a VL CDR2 having the amino acid sequence YTSNLAS (SEQ ID NO: 37), and a VL CDR3 having the amino acid sequence QQRSSYPFT (SEQ ID NO: 38).

In some aspects, the light chain variable region of the isolated antibody or antigen binding fragment thereof comprises a VL CDR1 having the amino acid sequence SASSGVTYMH (SEQ ID NO: 42), a VL CDR2 having the amino acid sequence RTSNLAS (SEQ ID NO: 43), and a VL CDR3 having the amino acid sequence QQRSSYPFT (SEQ ID NO: 44).

In some aspects, the light chain variable region of the isolated antibody or antigen binding fragment thereof comprises a VL CDR1 having the amino acid sequence SSVSYMH (SEQ ID NO: 49), a VL CDR2 having the amino acid sequence LWIYSTSNLAS (SEQ ID NO: 50), and a VL CDR3 having the amino acid sequence QQRSTYPF (SEQ ID NO: 51).

In some aspects, the light chain variable region of the isolated antibody or antigen binding fragment thereof comprises a VL CDR1 having the amino acid sequence SSVSYMH (SEQ ID NO: 55), a VL CDR2 having the amino acid sequence LWIYSTSNLAS (SEQ ID NO: 56), and a VL CDR3 having the amino acid sequence QQRSFYPF (SEQ ID NO: 57).

In some aspects, the light chain variable region of the isolated antibody or antigen binding fragment thereof comprises a VL CDR1 having the amino acid sequence SSVRYMH (SEQ ID NO: 61), a VL CDR2 having the amino acid sequence VWIYSTSNLAS (SEQ ID NO: 62), and a VL CDR3 having the amino acid sequence QQRTYYPF (SEQ ID NO: 63).

In some aspects of the disclosure the isolated antibody or antigen binding fragment thereof comprises a heavy chain variable region that comprises VH CDR1, VH CDR2, and VH CDR3 domains and a light chain variable region that comprises VL CDR1, VL CDR2, and VL CDR3 domains selected from the group consisting of:

a. a VH CDR1 having the amino acid sequence set forth in SEQ ID NO: 33, a VH CDR2 having the amino acid sequence set forth in SEQ ID NO: 34, a VH CDR3 having the amino acid sequence set forth in SEQ ID NO: 35, a VL CDR1 having the amino acid sequence set forth in SEQ ID NO: 36, a VL CDR2 having the amino acid sequence set forth in SEQ ID NO: 37, and a VL CDR3 having the amino acid sequence set forth in SEQ ID NO: 38;

b. a VH CDR1 having the amino acid sequence set forth in SEQ ID NO: 39, a VH CDR2 having the amino acid sequence set forth in SEQ ID NO: 40, a VH CDR3 having the amino acid sequence set forth in SEQ ID NO: 41, a VL CDR1 having the amino acid sequence set forth in SEQ ID NO: 42, a VL CDR2 having the amino acid sequence set forth in SEQ ID NO: 43, and a VL CDR3 having the amino acid sequence set forth in SEQ ID NO: 44;

c. a VH CDR1 having the amino acid sequence set forth in SEQ ID NO: 46, a VH CDR2 having the amino acid sequence set forth in SEQ ID NO: 47, a VH CDR3 having the amino acid sequence set forth in SEQ ID NO: 48, a VL CDR1 having the amino acid sequence set forth in SEQ ID NO: 49, a VL CDR2 having the amino acid sequence set forth in SEQ ID NO: 50, and a VL CDR3 having the amino acid sequence set forth in SEQ ID NO: 51;

d. a VH CDR1 having the amino acid sequence set forth in SEQ ID NO: 52, a VH CDR2 having the amino acid sequence set forth in SEQ ID NO: 53, a VH CDR3 having the amino acid sequence set forth in SEQ ID NO: 54, a VL CDR1 having the amino acid sequence set forth in SEQ ID NO: 55 a VL CDR2 having the amino acid sequence set forth in SEQ ID NO: 56, and a VL CDR3 having the amino acid sequence set forth in SEQ ID NO: 57; and e. a VH CDR1 having the amino acid sequence set forth in SEQ ID NO: 58, a VH CDR2 having the amino acid sequence set forth in SEQ ID NO: 59, a VH CDR3 having the amino acid sequence set forth in SEQ ID NO: 60, a VL CDR1 having the amino acid sequence set forth in SEQ ID NO: 61, a VL CDR2 having the amino acid sequence set forth in SEQ ID NO: 62, and a VL CDR3 having the amino acid sequence set forth in SEQ ID NO: 63.

In some aspects, the isolated antibody or antigen binding fragment thereof comprises:

a. a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 1; and a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 2;

b. a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 5; and a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 6;

c. a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 13; and a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 14;

d. a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 9; and a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 10; or e. a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 17; and a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence set forth in SEQ ID NO: 18.

In some aspects of the disclosure, the heavy chain variable region of the isolated antibody or antigen binding fragment thereof has an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence selected from the group consisting of SEQ ID NO: 1, SEQ ID NO: 5, SEQ ID NO: 13, SEQ ID NO: 9, and SEQ ID NO: 17; and further comprises a VH CDR1, VH CDR2, and VH CDR3 from an amino acid sequence selected from the group consisting of SEQ ID NO: 1, SEQ ID NO: 5, SEQ ID NO: 13, SEQ ID NO: 9, and SEQ ID NO: 17.

In some aspects of the disclosure, the heavy chain variable region of the isolated antibody or antigen binding fragment thereof is selected from the group consisting of SEQ ID NO: 1, SEQ ID NO: 5, SEQ ID NO: 13, SEQ ID NO: 9, and SEQ ID NO: 17.

In some aspects of the disclosure, the light chain variable region of the isolated antibody or antigen binding fragment thereof has an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to an amino acid sequence selected from the group consisting of SEQ ID NO: 2, SEQ ID NO: 6, SEQ ID NO: 14, SEQ ID NO: 10, and SEQ ID NO: 18; and further comprises a VL CDR1, VL CDR2, and/or VL CDR3 from an amino acid sequence selected from the group consisting of SEQ ID NO: 2, SEQ ID NO: 6, SEQ ID NO: 14, SEQ ID NO: 10, and SEQ ID NO: 18.

In some aspects, the light chain variable region of the isolated antibody or antigen binding fragment thereof is selected from the group consisting of SEQ ID NO: 2, SEQ ID NO: 6, SEQ ID NO: 14, SEQ ID NO: 10, and SEQ ID NO: 18.

In some aspects, the heavy chain variable region of the isolated antibody or antigen binding fragment thereof comprises an amino acid sequence selected from the group consisting of SEQ ID NO: 1, SEQ ID NO: 5, SEQ ID NO: 13, SEQ ID NO: 9, and SEQ ID NO: 17; and the light chain variable region comprises an amino acid sequence selected from the group consisting of SEQ ID NO: 2, SEQ ID NO: 6, SEQ ID NO: 14, SEQ ID NO: 10, and SEQ ID NO: 18.

In some aspects, the isolated antibody or antigen binding fragment thereof comprises a heavy chain variable region comprising the amino acid sequence set forth in SEQ ID NO: 1 and a light chain variable region comprising the amino acid sequence set forth in SEQ ID NO: 2.

In some aspects, the isolated antibody or antigen binding fragment thereof comprises a heavy chain variable region comprising the amino acid sequence set forth in SEQ ID NO: 5 and a light chain variable region comprising the amino acid sequence set forth in SEQ ID NO: 6.

In some aspects, the isolated antibody or antigen binding fragment thereof comprises a heavy chain variable region comprising the amino acid sequence set forth in SEQ ID NO: 13 and a light chain variable region comprising the amino acid sequence set forth in SEQ ID NO: 14.

In some aspects, the isolated antibody or antigen binding fragment thereof comprises a heavy chain variable region comprising the amino acid sequence set forth in SEQ ID NO: 9 and a light chain variable region comprising the amino acid sequence set forth in SEQ ID NO: 10.

In some aspects, the isolated antibody or antigen binding fragment thereof comprises a heavy chain variable region comprising the amino acid sequence set forth in SEQ ID NO: 17 and a light chain variable region comprising the amino acid sequence set forth in SEQ ID NO: 18.

In some aspects, the isolated antibody of the present disclosure is an antibody presented below in Table 1.

TABLE 1

Antibody amino acid sequences

| Antibody | Sequence |
|---|---|
| 10D2-1 | VH:<br>MDWLWNLLFLMAAAQSAQTQIQLVQSGPELRKPGETVKIS<br>CKASGYSFTNYGMNWVKQTPGKDLKWMGWINTYTGEPTYA<br>DDFKGRFAFSLEASANTAYLQINDLKNEDMATYFCARGVA<br>HYSDSRFAFDYWGQGTTLTVPS<br>(SEQ ID NO: 1)<br>VL:<br>MHFQVQIFSFLLISASVIMSRGQIVLTQSPAIMSASPGEK<br>VTITCSVSSSVSYMHWFQQKPGTSPKLWIYYTSNLASGVP<br>GRFSGSGSGTSYSLTISRMEAEDAATYYCQQRSSYPFTFG<br>SGTKLEIK<br>(SEQ ID NO: 2) |

TABLE 1-continued

Antibody amino acid sequences

| Antibody | Sequence |
|---|---|
| 28D8-1 | VH:<br>MDWLWNLLFLMAAAQSAQTQIQLVQSGPELKKPGETVKIS<br>CKAAGYTFTDYGMNWVKQAPGEGLKWMGWINTNTGEPTYG<br>DDFKGRFAFSLEASASTAHLQINNLKNDDMAIYFCARGNA<br>HPGGSAFVYWGQGTLVTVSA<br>(SEQ ID NO: 5)<br>VL:<br>MHFQVQIFSFLLISASVIMSRGQIVLTQSPAIMSASPGES<br>VTITCSASSGVTYMHWFQQKPGTSPKNWIYRTSNLASGVP<br>ARFSGSGSGTSYSLTISRMEAEDAATYYCQQRSSYPFTFG<br>SGTKLEIK<br>(SEQ ID NO: 6) |
| 1C4F4 | VH:<br>QVKLEESGPELKKPGETVKISCKASGYTFTNYGMNWVKQ<br>APGKGLKWMGWINTYTGEPTYADDFKGRFAFSLETSARK<br>VYLQINNLKNEDMATYFCARGSYYYDSSPAWFAYWGQGT<br>LVTVSA<br>(SEQ ID NO: 13)<br>VL:<br>QIVLTQSPAIMSASPGEKVTITCSASSSVSYMHWFQQKP<br>GTSPKLWIYSTSNLASGVPARFSGSGSGTSYSLTISRME<br>AEDAATYYCQQRSTYPFTFGSGTKLEIKR<br>(SEQ ID NO: 14) |
| 6E10B5 | VH:<br>QVKLQESGPELKKPGETVKISCKASGYTFTKYGMNWVKQ<br>APGEGLKWMGWINTYTGEPTYADDFKGRFAFSLKTSAST<br>AYLQINNLKNEGTTTYFCARGVDSSGYGAFAYWGQGTLV<br>TVSA<br>(SEQ ID NO: 9)<br>VL:<br>QIVLTQSPAIMSASPGEKVTITCSASSSVSYMHWFQQKP<br>GTSPKLWIYSTSNLASGVPARFSGSGSGTSYSLTISRME<br>AEDAATYYCQQRSFYPFTFGSGTKLEIKR<br>(SEQ ID NO: 10) |
| 7D4B9 | VH:<br>EVQLQESGSDLKKPGETVKISCKASGYTFTNYGMNWVKQ<br>APGKGLKWMGWINTYTGEPTYADDFKGRFAFSLETSAST<br>AFLQINNLKYEDTGTYFCTRGTSTMISTFAFVYWGQGTL<br>VTVSA<br>(SEQ ID NO: 17)<br>VL:<br>QIVLTQSPAIMSASPGEKVTITCSASSSVRYMHWFQQKP<br>GTSPKVWIYSTSNLASGVPARFSGSGSGTSYSLTISRME<br>AEDAATYYCQQRTYYPFTFGSGTKLEIKR<br>(SEQ ID NO: 18) |

In some aspects, the isolated antibody or antigen-binding fragment thereof comprises a heavy chain variable region that comprises VH CDR1, VH CDR2, and VH CDR3 domains and a light chain variable region that comprises VL CDR1, VL CDR2, and VL CDR3 domains selected from the sequences presented in Table 2.

TABLE 2

CDR amino acid sequences

| CDR | Sequence | SEQ ID NO. |
|---|---|---|
| 10D2-1 VH CDR1 | NYGMN | 33 |
| 10D2-1 VH CDR2 | WINTYTGEPTYADDFKG | 34 |
| 10D2-1 VH CDR3 | GVAHYSDSRFAFDY | 35 |
| 10D2-1 VL CDR1 | SVSSSVSYMH | 36 |
| 10D2-1 VL CDR2 | YTSNLAS | 37 |
| 10D2-1 VL CDR3 | QQRSSYPFT | 38 |
| 28D8-1 VH CDR1 | DYGMN | 39 |
| 28D8-1 VH CDR2 | WINTNTGEPTYGDDFKG | 40 |
| 28D8-1 VH CDR3 | GNAHPGGSAFVY | 41 |
| 28D8-1 VL CDR1 | SASSGVTYMH | 42 |
| 28D8-1 VL CDR2 | RTSNLAS | 43 |
| 28D8-1 VL CDR3 | QQRSSYPFT | 44 |
| 1C4F4 VH CDR1 | YTFTNYGMN | 46 |
| 1C4F4 VH CDR2 | WMGWINTYTGEPTY | 47 |
| 1C4F4 VH CDR3 | RGSYYYDSSPAWFAY | 48 |
| 1C4F4 VL CDR1 | SSVSYMH | 49 |
| 1C4F4 VL CDR2 | LWIYSTSNLAS | 50 |
| 1C4F4 VL CDR3 | QQRSTYPF | 51 |
| 6E10B5 VH CDR1 | YTFTKYGMN | 52 |
| 6E10B5 VH CDR2 | WMGWINTYTGEPTY | 53 |
| 6E10B5 VH CDR3 | RGVDSSGYGAFAY | 54 |
| 6E10B5 VL CDR1 | SSVSYMH | 55 |
| 6E10B5 VL CDR2 | LWIYSTSNLAS | 56 |
| 6E10B5 VL CDR3 | QQRSFYPF | 57 |
| 7D4B9 VH CDR1 | YTFTNYGMN | 58 |
| 7D4B9 VH CDR2 | WMGWINTYTGEPTY | 59 |
| 7D4B9 VH CDR3 | TRGTSTMISTFAFVY | 60 |
| 7D4B9 VL CDR1 | SSVRYMH | 61 |
| 7D4B9 VL CDR2 | VWIYSTSNLAS | 62 |
| 7D4B9 VL CDR3 | QQRTYYPF | 63 |

Standard assays to evaluate the binding ability of the antibodies toward AAVrh74 or AAVrh74 antibody are known in the art, including for example, ELISAs, BIAcore®, Western blots, RIAs, and flow cytometry analysis. The binding kinetics (e.g., binding affinity like KD) of the antibodies also can be assessed by standard assays known in the art, such as by Scatchard or BIAcore® system analysis. The relative binding affinity $K_i$ can be assessed by standard competition assays known in the art.

In some aspects, the isolated antibody or antigen-binding fragment thereof is labeled with a radioactive, enzymatic, or fluorescent group. Examples of groups for purposes of labeling antibodies include various enzymes, binding pairs, fluorescent materials, luminescent materials, bioluminescent materials, and radioactive materials. Examples of suitable enzymes include but are not limited to horseradish peroxidase, alkaline phosphatase, β-galactosidase, or acetylcholinesterase; examples of suitable binding pairs include but are not limited to streptavidin/biotin and avidin/biotin; examples of suitable fluorescent groups include but are not limited to umbelliferone, fluorescein, fluorescein isothiocyanate, rhodamine, dichlorotriazinylamine fluorescein, dansylchloride or phycoerythrin; an example of a luminescent material includes but is not limited to luminol; examples of bioluminescent materials include but are not limited to luciferase, luciferin, and aequorin; and examples of suitable radioactive material include $^{125}$I, $^{131}$I, $^{35}$S, or $^{3}$H.

In some embodiments, the isolated antibody is a full-length antibody or an antibody fragment selected from the group consisting of Fab, Fab', Fab'-SH, Fd, Fv, dAb, F(ab')2, scFv, bispecific single chain Fv dimers, diabodies, triabodies, and sxFv genetically fused to the same or a different antibody.

In some embodiments, the isolated antibody is a murine antibody, a chimeric antibody, a human antibody, an engineered antibody, or a humanized antibody. In some aspects, the chimeric antibody is a chimeric murine/human antibody.

In some aspects, the isolated antibody is a chimeric antibody comprising a heavy chain comprising the amino acid sequence set forth in SEQ ID NO: 21. In some aspects, the isolated antibody is a chimeric antibody comprising a light chain comprising the amino acid sequence set forth in SEQ ID NO: 22. In some aspects, the isolated antibody is a chimeric antibody comprising a heavy chain comprising the amino acid sequence set forth in SEQ ID NO: 21 and a light chain comprising the amino acid sequence set forth in SEQ ID NO: 22.

In some aspects, the isolated antibody is a chimeric antibody comprising a heavy chain comprising the amino acid sequence set forth in SEQ ID NO: 23. In some aspects, the isolated antibody is a chimeric antibody comprising a light chain comprising the amino acid sequence set forth in SEQ ID NO: 24. In some aspects, the isolated antibody is a chimeric antibody comprising a heavy chain comprising the amino acid sequence set forth in SEQ ID NO: 23 and a light chain comprising the amino acid sequence set forth in SEQ ID NO: 24.

In other aspects, the isolated antibody is a chimeric antibody comprising a heavy chain comprising the amino acid sequence set forth in SEQ ID NO: 25. In some aspects, the isolated antibody is a chimeric antibody comprising a light chain comprising the amino acid sequence set forth in SEQ ID NO: 26. In some aspects, the isolated antibody is a chimeric antibody comprising a heavy chain comprising the amino acid sequence set forth in SEQ ID NO: 25 and a light chain comprising the amino acid sequence set forth in SEQ ID NO: 26.

In other aspects, the isolated antibody is a chimeric antibody comprising a heavy chain comprising the amino acid sequence set forth in SEQ ID NO: 27. In some aspects, the isolated antibody is a chimeric antibody comprising a light chain comprising the amino acid sequence set forth in SEQ ID NO: 28. In some aspects, the isolated antibody is a chimeric antibody comprising a heavy chain comprising the amino acid sequence set forth in SEQ ID NO: 27 and a light chain comprising the amino acid sequence set forth in SEQ ID NO: 28.

In some aspects, the isolated antibody is a chimeric antibody presented in Table 3:

TABLE 3

Chimeric antibody sequences

| Antibody | Chimera | Amino Acid Sequence |
|---|---|---|
| 10D2-1 | Mouse/Human IgG1 | Heavy chain:<br>MGWSCIILFLVATATGVHSQIQLVQSGPELRKPGETVKISC<br>KASGYSFTNYGMNWVKQTPGKDLKWMGWINTYTGEPTYADD<br>FKGRFAFSLEASANTAYLQINDLKNEDMATYFCARGVAHYS<br>DSRFAFDYWGQGTTLTVPSASTKGPSVFPLAPSSKSTSGGT<br>AALGCLVKDYFPEPVTVSWNSGALTSGVHTFPAVLQSSGLY<br>SLSSVVTVPSSSLGTQTYICNVNHKPSNTKVDKKVEPKSCD<br>KTHTCPPCPAPELLGGPSVFLFPPKPKDTLMISRTPEVTCV<br>VVDVSHEDPEVKFNWYVDGVEVHNAKTKPREEQYNSTYRVV<br>SVLTVLHQDWLNGKEYKCKVSNKALPAPIEKTISKAKGQPR<br>EPQVYTLPPSRDELTKNQVSLTCLVKGFYPSDIAVEWESNG<br>QPENNYKTTPPVLDSDGSFFLYSKLTVDKSRWQQGNVFSCS<br>VMHEALHNHYTQKSLSLSPGK<br>(SEQ ID NO: 21)<br>Light chain:<br>MGWSCIILFLVATATGVHSQIVLTQSPAIMSASPGEKVTIT<br>CSVSSSVSYMHWFQQKPGTSPKLWIYYTSNLASGVPGRFSG<br>SGSGTSYSLTISRMEAEDAATYYCQQRSSYPFTFGSGTKLE<br>IKRTVAAPSVFIFPPSDEQLKSGTASVVCLLNNFYPREAKV<br>QWKVDNALQSGNSQESVTEQDSKDSTYSLSSTLTLSKADYE<br>KHKVYACEVTHQGLSSPVTKSFNRGEC<br>(SEQ ID NO: 22) |
| 10D2-1 | Mouse/Human IgA | Heavy chain:<br>MGWSCIILFLVATATGVHSQIQLVQSGPELRKPGETVKISC<br>KASGYSFTNYGMNWVKQTPGKDLKWMGWINTYTGEPTYADD<br>FKGRFAFSLEASANTAYLQINDLKNEDMATYFCARGVAHYS<br>DSRFAFDYWGQGTTLTVPSASPTSPKVFPLSLCSTQPDGNV<br>VIACLVQGFFPQEPLSVTWSESGQGVTARNFPPSQDASGDL<br>YTTSSQLTLPATQCLAGKSVTCHVKHYTNPSQDVTVPCPVP<br>STPPTPSPSTPPTPSPSCCHPRLSLHRPALEDLLLGSEANL<br>TCTLTGLRDASGVTFTWTPSSGKSAVQGPPERDLCGCYSVS<br>SVLPGCAEPWNHGKTFTCTAAYPESKTPLTATLSKSGNTFR<br>PEVHLLPPPSEELALNELVTLTCLARGFSPKDVLVRWLQGS<br>QELPREKYLTWASRQEPSQGTTTFAVTSILRVAAEDWKKGD<br>TFSCMVGHEALPLAFTQKTIDRLAGKPTHVNVSVVMAEVDG<br>TCY<br>(SEQ ID NO: 23) |

TABLE 3-continued

Chimeric antibody sequences

| Antibody | Chimera | Amino Acid Sequence |
|---|---|---|
| | | Light chain:<br>MGWSCIILFLVATATGVHSQIVLTQSPAIMSASPGEKVTIT<br>CSVSSSVSYMHWFQQKPGTSPKLWIYYTSNLASGVPGRFSG<br>SGSGTSYSLTISRMEAEDAATYYCQQRSSYPFTFGSGTKLE<br>IKRTVAAPSVFIFPPSDEQLKSGTASVVCLLNNFYPREAKV<br>QWKVDNALQSGNSQESVTEQDSKDSTYSLSSTLTLSKADYE<br>KHKVYACEVTHQGLSSPVTKSFNRGEC<br>(SEQ ID NO: 24) |
| 28D8-1 | Mouse/Human IgG1 | Heavy chain:<br>MGWSCIILFLVATATGVHSQIQLVQSGPELKKPGETVKISC<br>KAAGYTFTDYGMNWVKQAPGEGLKWMGWINTNTGEPTYGDD<br>FKGRFAFSLEASASTAHLQINNLKNDDMAIYFCARGNAHPG<br>GSAFVYWGQGTLVTVSAASTKGPSVFPLAPSSKSTSGGTAA<br>LGCLVKDYFPEPVTVSWNSGALTSGVHTFPAVLQSSGLYSL<br>SSVVTVPSSSLGTQTYICNVNHKPSNTKVDKKVEPKSCDKT<br>HTCPPCPAPELLGGPSVFLFPPKPKDTLMISRTPEVTCVVV<br>DVSHEDPEVKFNWYVDGVEVHNAKTKPREEQYNSTYRVVSV<br>LTVLHQDWLNGKEYKCKVSNKALPAPIEKTISKAKGQPREP<br>QVYTLPPSRDELTKNQVSLTCLVKGFYPSDIAVEWESNGQP<br>ENNYKTTPPVLDSDGSFFLYSKLTVDKSRWQQGNVFSCSVM<br>HEALHNHYTQKSLSLSPGK<br>(SEQ ID NO: 25)<br>Light chain:<br>MGWSCIILFLVATATGVHSQIVLTQSPAIMSASPGESVTIT<br>CSASSGVTYMHWFQQKPGTSPKNWIYRTSNLASGVPARFSG<br>SGSGTSYSLTISRMEAEDAATYYCQQRSSYPFTFGSGTKLE<br>IKRTVAAPSVFIFPPSDEQLKSGTASVVCLLNNFYPREAKV<br>QWKVDNALQSGNSQESVTEQDSKDSTYSLSSTLTLSKADYE<br>KHKVYACEVTHQGLSSPVTKSFNRGEC<br>(SEQ ID NO: 26) |
| 28D8-1 | Mouse/Human IgA | Heavy chain:<br>MGWSCIILFLVATATGVHSQIQLVQSGPELKKPGETVKISC<br>KAAGYTFTDYGMNWVKQAPGEGLKWMGWINTNTGEPTYGDD<br>FKGRFAFSLEASASTAHLQINNLKNDDMAIYFCARGNAHPG<br>GSAFVYWGQGTLVTVSAASPTSPKVFPLSLCSTQPDGNVVI<br>ACLVQGFFPQEPLSVTWSESGQGVTARNFPPSQDASGDLYT<br>TSSQLTLPATQCLAGKSVTCHVKHYTNPSQDVTVPCPVPST<br>PPTPSPSTPPTPSPSCCHPRLSLHRPALEDLLLGSEANLTC<br>TLTGLRDASGVTFTWTPSSGKSAVQGPPERDLCGCYSVSSV<br>LPGCAEPWNHGKTFTCTAAYPESKTPLTATLSKSGNTFRPE<br>VHLLPPPSEELALNELVTLTCLARGFSPKDVLVRWLQGSQE<br>LPREKYLTWASRQEPSQGTTTFAVTSILRVAAEDWKKGDTF<br>SCMVGHEALPLAFTQKTIDRLAGKPTHVNVSVVMAEVDGTC<br>Y<br>(SEQ ID NO: 27)<br>Light chain:<br>MGWSCIILFLVATATGVHSQIVLTQSPAIMSASPGESVTIT<br>CSASSGVTYMHWFQQKPGTSPKNWIYRTSNLASGVPARFSG<br>SGSGTSYSLTISRMEAEDAATYYCQQRSSYPFTFGSGTKLE<br>IKRTVAAPSVFIFPPSDEQLKSGTASVVCLLNNFYPREAKV<br>QWKVDNALQSGNSQESVTEQDSKDSTYSLSSTLTLSKADYE<br>KHKVYACEVTHQGLSSPVTKSFNRGEC<br>(SEQ ID NO: 28) |

In some embodiments, the isolated antibody or antigen binding fragment thereof is a bispecific antibody. In some embodiments, the isolated antibody or antigen binding fragment thereof is a multispecific antibody.

Nucleic Acids, Vectors and Host Cells

The present disclosure also provides isolated polynucleotides that comprise nucleic acids encoding the antibodies and fragments thereof that bind to AAVrh74, vectors, and host cells comprising the polynucleotides or the vector. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art, see e.g., F. Ausubel, et al., ed. (1987) Current Protocols in Molecular Biology, Greene Publishing and Wiley Interscience, New York. A nucleic acid of the invention can be, for example, DNA or RNA and may or may not contain intron sequences. In a preferred embodiment, the nucleic acid is a cDNA molecule.

Nucleic acids of the invention can be obtained using standard molecular biology techniques e.g. cDNAs encoding the light and/or heavy chains of the antibody or encoding VH and/or VL segments can be obtained by standard PCR amplification or cDNA cloning techniques. For antibodies obtained from an immunoglobulin gene library (e.g., using phage display techniques), one or more nucleic acids encoding the antibody can be recovered from the library. The methods of introducing exogenous nucleic acid into host cells are well known in the art, and will vary with the host cell used. Techniques include but are not limited to dextran-mediated transfection, calcium phosphate precipitation, calcium chloride treatment, polyethylenimine mediated transfection, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In some aspects, the polynucleotide of the disclosure comprises a nucleic acid sequence that encodes a VH CDR1 domain comprising an amino acid sequence selected from the group consisting of SEQ ID NO: 33, SEQ ID NO: 39, SEQ ID NO: 46, SEQ ID NO: 52, and SEQ ID NO: 58.

In some aspects, the polynucleotide of the disclosure comprises a nucleic acid sequence that encodes a VH CDR2 domain comprises an amino acid sequence selected from the group consisting of SEQ ID NO: 34, SEQ ID NO: 40, SEQ ID NO: 47, SEQ ID NO: 53, and SEQ ID NO: 59.

In some aspects, the polynucleotide of the disclosure comprises a nucleic acid sequence that encodes a VH CDR3 domain comprises an amino acid sequence selected from the group consisting of SEQ ID NO: 35, SEQ ID NO: 41, SEQ ID NO: 48, SEQ ID NO: 54, and SEQ ID NO: 60.

In some aspects, the polynucleotide of the disclosure comprises a nucleic acid sequence that encodes a VL CDR1 domain comprises an amino acid sequence selected from the group consisting of SEQ ID NO: 36, SEQ ID NO: 42, SEQ ID NO: 49, SEQ ID NO: 55, and SEQ ID NO: 61.

In some aspects, the polynucleotide of the disclosure comprises a nucleic acid sequence that encodes a VL CDR2 domain comprises an amino acid sequence selected from the group consisting of SEQ ID NO: 37, SEQ ID NO: 43, SEQ ID NO: 50, SEQ ID NO: 56, and SEQ ID NO: 62.

In some aspects, the polynucleotide of the disclosure comprises a nucleic acid sequence that encodes a VL CDR3 domain comprises an amino acid sequence selected from the group consisting of SEQ ID NO: 38, SEQ ID NO: 44, SEQ ID NO: 51, SEQ ID NO: 57, and SEQ ID NO: 63.

In some aspects, the polynucleotide of the disclosure comprises a nucleic acid sequence that encodes (a) a VH CDR1 domain comprising an amino acid sequence selected from the group consisting of SEQ ID NO: 33, SEQ ID NO: 39, SEQ ID NO: 46, SEQ ID NO: 52, and SEQ ID NO: 58; (b) a VH CDR2 domain comprises an amino acid sequence selected from the group consisting of SEQ ID NO: 34, SEQ ID NO: 40, SEQ ID NO: 47, SEQ ID NO: 53, and SEQ ID NO: 59; (c) a VH CDR3 domain comprises an amino acid sequence selected from the group consisting of SEQ ID NO: 35, SEQ ID NO: 41, SEQ ID NO: 48, SEQ ID NO: 54, and SEQ ID NO: 60; (d) a VL CDR1 domain comprises an amino acid sequence selected from the group consisting of SEQ ID NO: 36, SEQ ID NO: 42, SEQ ID NO: 49, SEQ ID NO: 55, and SEQ ID NO: 61; (e) a VL CDR2 domain comprises an amino acid sequence selected from the group consisting of SEQ ID NO: 37, SEQ ID NO: 43, SEQ ID NO: 50, SEQ ID NO: 56, and SEQ ID NO: 62; and (f) a VL CDR3 domain comprises an amino acid sequence selected from the group consisting of SEQ ID NO: 38, SEQ ID NO: 44, SEQ ID NO: 51, SEQ ID NO: 57, and SEQ ID NO: 63

In some aspects of the disclosure, the nucleic acid encoding the heavy chain variable region of the antibody of fragment thereof comprises a nucleotide sequence selected from the group consisting of SEQ ID NO: 3; SEQ ID NO: 7; SEQ ID NO: 15; SEQ ID NO: 11; and SEQ ID NO: 19.

In some aspects of the disclosure, the nucleic acid encoding the light chain variable region comprises a nucleotide sequence selected from the group consisting of SEQ ID NO: 4; SEQ ID NO: 8; SEQ ID NO: 16; SEQ ID NO: 12; and SEQ ID NO: 20.

In some aspects of the disclosure, the nucleic acid encoding the heavy chain variable region of the antibody of fragment thereof comprises a nucleotide sequence selected from the group consisting of SEQ ID NO: 3; SEQ ID NO: 7; SEQ ID NO: 15; SEQ ID NO: 11; and SEQ ID NO: 19; and the nucleic acid encoding the light chain variable region comprises a nucleotide sequence selected from the group consisting of SEQ ID NO: 4; SEQ ID NO: 8; SEQ ID NO: 16; SEQ ID NO: 12; and SEQ ID NO: 20.

In some aspects, the nucleic acid encoding the heavy chain variable region of the antibody of fragment thereof comprises the nucleotide sequence of SEQ ID NO: 3 and the nucleic acid encoding the light chain variable region comprises the nucleotide sequence of SEQ ID NO: 4.

In some aspects, the nucleic acid encoding the heavy chain variable region of the antibody of fragment thereof comprises the nucleotide sequence of SEQ ID NO: 7 and the nucleic acid encoding the light chain variable region comprises the nucleotide sequence of SEQ ID NO: 8.

In some aspects, the nucleic acid encoding the heavy chain variable region of the antibody of fragment thereof comprises the nucleotide sequence of SEQ ID NO: 11 and the nucleic acid encoding the light chain variable region comprises the nucleotide sequence of SEQ ID NO: 12.

In some aspects, the nucleic acid encoding the heavy chain variable region of the antibody of fragment thereof comprises the nucleotide sequence of SEQ ID NO: 15 and the nucleic acid encoding the light chain variable region comprises the nucleotide sequence of SEQ ID NO: 16.

In some aspects, the nucleic acid encoding the heavy chain variable region of the antibody of fragment thereof comprises the nucleotide sequence of SEQ ID NO: 19 and the nucleic acid encoding the light chain variable region comprises the nucleotide sequence of SEQ ID NO: 20.

In some aspects, the nucleic acid of the disclosure is a sequence set forth in Table 4:

TABLE 4

| Antibody nucleotide sequences | |
|---|---|
| Antibody | Nucleotide Sequence |
| 10D2-1 | VH:<br>ATGGATTGGCTGTGGAACTTGCTATTCCTGATGGCAGCTGCCCAAAGTGCCC<br>AAACACAGATCCAGTTGGTGCAGTCTGGACCTGAGTTGAGGAAGCCTGGAGA<br>GACAGTCAAGATCTCCTGCAAGGCTTCTGGATATTCCTTCACAAACTATGGA<br>ATGAACTGGGTGAAGCAGACTCCAGGAAAGGATTTAAAGTGGATGGGCTGGA |

TABLE 4-continued

Antibody nucleotide sequences

| Antibody | Nucleotide Sequence |
|---|---|
| | TAAACACCTACACTGGAGAGCCAACATATGCTGATGACTTCAAGGGACGGTT<br>CGCCTTCTCTCTGGAAGCCTCTGCCAACACTGCCTATTTGCAGATCAACGAC<br>CTCAAAAATGAGGACATGGCTACATATTTCTGTGCAAGGGGTGTGGCTCATT<br>ACTCCGATAGTAGGTTCGCCTTTGACTACTGGGGCCAAGGAACCACTCTCAC<br>AGTCCCCTCC<br>(SEQ ID NO: 3)<br>VL:<br>ATGCATTTTCAAGTGCAGATTTTCAGCTTCCTGCTAATCAGTGCCTCAGTCA<br>TAATGTCCAGAGGACAAATTGTTCTCACCCAGTCACCAGCAATCATGTCTGC<br>ATCTCCAGGGGAGAAGGTCACCATAACCTGCAGTGTCAGCTCAAGTGTTAGT<br>TACATGCACTGGTTCCAGCAGAAGCCAGGCACTTCTCCCAAACTCTGGATTT<br>ATTACACATCCAACCTGGCTTCTGGAGTCCCTGGTCGCTTCAGTGGCAGTGG<br>ATCTGGGACCTCTTACTCCCTCACAATCAGCCGAATGGAGGCTGAAGATGCT<br>GCCACTTATTACTGCCAGCAAAGGAGTAGTTACCCATTCACGTTCGGCTCGG<br>GGACAAAGTTGGAAATAAAA<br>(SEQ ID NO: 4) |
| 28D8-1 | VH:<br>ATGGATTGGCTGTGGAACTTGCTATTCCTGATGGCAGCAGCCCAAAGCGCCC<br>AAACACAGATCCAGTTGGTGCAGTCTGGACCTGAGCTGAAGAAGCCTGGAGA<br>GACAGTCAAGATCTCCTGCAAGGCTGCTGGGTATACCTTCACAGACTATGGA<br>ATGAACTGGGTGAAGCAGGCTCCAGGAGAGGGTTTAAAGTGGATGGGCTGGA<br>TAAACACCAATACTGGAGAGCCAACATATGGTGATGACTTCAAGGGACGGTT<br>TGCCTTCTCTTTGGAAGCCTCTGCCAGCACTGCCCATTTGCAGATCAACAAC<br>CTCAAAAATGACGCATGGCAATATATTTCTGTGCAAGAGGGAACGCTCATC<br>CCGGTGGTAGTGCGTTTGTTTACTGGGGCCAAGGGACTCTGGTCACTGTCTC<br>TGCA<br>(SEQ ID NO: 7)<br>VL:<br>ATGCATTTTCAAGTGCAGATTTTCAGCTTCCTGCTAATCAGTGCCTCAGTCA<br>TAATGTCCAGAGGACAAATTGTTCTCACCCAGTCTCCAGCAATCATGTCTGC<br>ATCTCCAGGGGAGAGTGTCACCATAACCTGCAGTGCCAGCTCAGGTGTCACT<br>TACATGCACTGGTTCCAGCAGAAGCCAGGCACTTCTCCCAAAAACTGGATTT<br>ATAGAACATCCAATCTGGCTTCTGGAGTCCCTGCTCGCTTCAGTGGCAGTGG<br>ATCTGGGACCTCTTACTCTCTCACAATCAGCCGAATGGAGGCTGAAGATGCT<br>GCCACTTATTACTGCCAGCAAAGGAGTAGTTACCCATTCACATTCGGCTCGG<br>GGACAAAGTTGGAAATAAAA<br>(SEQ ID NO: 8) |
| 1C4F4 | VH:<br>CAGGTGAAGCTGGAGGAGTCTGGACCTGAGCTGAAGAAGCCTGGAGAGACAG<br>TCAAGATCTCCTGCAAGGCTTCTGGGTATACCTTCACAAACTATGGAATGAA<br>CTGGGTGAAGCAGGCTCCAGGAAAGGGTTTAAAGTGGATGGGCTGGATAAAC<br>ACCTACACTGGAGAGCCAACATATGCTGATGACTTCAAGGGACGGTTTGCCT<br>TCTCTTTGGAAACCTCTGCCAGGAAAGTCTATTTGCAGATCAACAACCTCAA<br>AAATGAGGACATGGCTACATATTTCTGTGCAAGGGGTTCTTATTACTACGAC<br>AGTAGCCCTGCCTGGTTTGCTTACTGGGGCCAAGGGACTCTGGTCACTGTCT<br>CTGCA<br>(SEQ ID NO: 15)<br>VL:<br>CAAATTGTTCTCACCCAGTCTCCAGCAATCATGTCTGCATCTCCAGGGGAGA<br>AGGTCACCATAACCTGCAGTGCCAGTTCAAGTGTAAGTTACATGCACTGGTT<br>CCAGCAGAAGCCAGGCACTTCTCCCAAACTCTGGATTTATAGCACATCCAAC<br>CTGGCTTCTGGAGTCCCTGCTCGCTTCAGTGGCAGTGGATCTGGGACCTCTT<br>ACTCTCTCACAATCAGCCGAATGGAGGCTGAGGATGCTGCCACTTATTACTG<br>CCAGCAAAGGAGTACTTACCCATTCACGTTCGGCTCGGGGACAAAGTTGGAA<br>ATAAAACGG<br>(SEQ ID NO: 16) |
| 6E10B5 | VH:<br>CAAGTTAAGCTGCAGGAGTCTGGACCTGAGCTGAAGAAGCCTGGAGAGACAG<br>TCAAGATCTCCTGCAAGGCTTCTGGGTATACCTTCACAAAGTATGGAATGAA<br>CTGGGTGAAGCAGGCTCCAGGAGAGGGTTTAAAGTGGATGGGCTGGATAAAC<br>ACCTACACTGGAGAGCCAACATATGCTGATGACTTCAAGGGACGGTTTGCCT<br>TCTCTTTGAAAACCTCTGCCAGTACTGCCTATTTGCAGATCAACAACCTCAA<br>AAATGAGGGCACGACTACATATTTCTGTGCAAGAGGGGTAGACAGCTCGGGC<br>TACGGCGCCTTTGCTTACTGGGGCCAAGGGACTCTGGTCACTGTCTCTGCA<br>(SEQ ID NO: 11)<br>VL:<br>AAGTGTAAGTTACATGCACTGGTTCCAGCAGAAGCCAGGCACTTCTCCCAAA<br>CTCTGGATTTATAGCACATCCAACCTGGCTTCTGGAGTCCCTGCTCGCTTCA<br>GTGGCAGTGGATCTGGGACCTCTTACTCTCTCACAATCAGCCGAATGGAGGC<br>TGAAGATGCAGCCACTTATTACTGCCAGCAAAGGAGTTTTTACCCATTCACG<br>TTCGGCTCGGGGACAAAGTTGGAAATAAAACGG<br>(SEQ ID NO: 12) |

TABLE 4-continued

Antibody nucleotide sequences

| Antibody | Nucleotide Sequence |
|---|---|
| 7D4B9 | VH:<br>GAAGTTCAGCTGCAGGAGTCTGGATCTGACCTGAAGAAGCCTGGAGAGACAG<br>TCAAGATCTCCTGCAAGGCTTCTGGGTATACCTTCACAAACTATGGAATGAA<br>CTGGGTGAAGCAGGCTCCAGGAAAGGGTTTAAAGTGGATGGGCTGGATAAAC<br>ACCTACACTGGAGAGCCAACATATGCTGATGACTTCAAGGGACGGTTTGCCT<br>TCTCTTTGGAAACCTCTGCCAGCACTGCCTTTTTGCAAATCAACAACCTCAA<br>ATATGAGGACACGGGTACATATTTCTGTACAAGAGGGACTTCTACTATGATT<br>TCGACGTTCGCGTTTGTTTACTGGGGCCAAGGGACTCTGGTCACCGTCTCTG<br>CG<br>(SEQ ID NO: 19)<br>VL:<br>CAAATTGTTCTCACCCAGTCTCCAGCAATCATGTCTGCATCTCCAGGGGAGA<br>AGGTCACCATAACCTGCAGTGCCAGCTCAAGTGTACGTTACATGCACTGGTT<br>CCAGCAGAAGCCAGGCACTTCTCCCAAAGTCTGGATTTATAGCACATCCAAC<br>CTGGCTTCTGGAGTCCCTGCTCGCTTCAGTGGCAGTGGATCTGGGACCTCTT<br>ACTCTCTCACAATCAGCCGAATGGAGGCTGAAGATGCTGCCACTTATTACTG<br>CCAGCAAAGGACTTATTACCCATTCACGTTCGGCTCGGGGACAAAGTTGGAA<br>ATAAAACGG<br>(SEQ ID NO: 20) |

Once DNA fragments encoding VH and/or VL segments are obtained, these DNA fragments can be further manipulated by standard recombinant DNA techniques, for example to convert a heavy chain variable region DNA sequence into a heavy chain full-length variable and constant region sequences, or to sequences encoding fragments corresponding to the fragments described herein such as Fab or scFv. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame. The isolated DNA encoding the VH region can be converted to a full-length heavy chain gene by operatively linking the VH-encoding DNA to another DNA molecule encoding heavy chain constant regions (CH1, CH2, CH3). The sequences of human heavy chain constant region genes are known in the art (see e.g., Kabat E A et al., supra) and DNA fragments encompassing these regions can be obtained by standard PCR amplification. The heavy chain constant region can be an IgG1 (IGHG1), IgG2 (IGHG2), IgG3 (IGHG3), IgG4 (IGHG4), IgA1 (IGHA1), IgA2 (IGHA2), IgM (IGHM), IgD (IGHD), or IgE (IGHE) constant region.

For a nucleic acid encoding a Fab fragment heavy chain, the VH-encoding DNA can be operatively linked to another DNA molecule encoding only the heavy chain CH1 constant region. The isolated DNA encoding the VL region can be converted to a full-length light chain (as well as a Fab light chain) by operatively linking the VL-encoding DNA to another DNA molecule encoding the light chain constant region, CL. The sequences of human light chain constant region genes are known in the art (see e.g., Kabat E A et al., supra.) and DNA fragments encompassing these regions can be obtained by standard PCR amplification. In some embodiments, the light chain constant region can be a kappa or lambda constant region, preferably a kappa constant region.

For a nucleic acid encoding a scFv, the VH- and VL-encoding DNA fragments are operatively linked to another fragment encoding a flexible linker, e.g., encoding an amino acid linker sequence, such that the VH and VL sequences can be expressed as a contiguous single-chain protein, with the VL and VH regions joined by the flexible linker (see e.g., Bird R E et al., (1988) Science, 242: 423-426; Huston J S et al., (1988) Proc. Natl. Acad. Sci. USA, 85: 5879-83; McCafferty J et al., (1990) Nature, 348: 552-554). Various techniques have been developed for the production of antibody fragments of antibodies. Traditionally, these fragments were derived via proteolytic digestion of intact antibodies (see, e.g., Morimoto K et al., (1992) J. Biochem. & Biophysical Methods, 24: 107-117 and Brennan M et al., (1985) Science, 229: 81-3). However, these fragments can now be produced directly by recombinant host cells. For example, the antibody fragments can be isolated from antibody phage libraries. Alternatively, Fab'-SH fragments can be directly recovered from E. coli and chemically coupled to form F(ab')2 fragments (Carter P et al., (1992) Bio/Technology, 10: 163-167). According to another approach, F(ab')2 fragments can be isolated directly from recombinant host cell culture. Other techniques for the production of antibody fragments will be apparent to the skilled practitioner. In some embodiments, the antibody of choice is a single-chain Fv fragment (scFv).

The nucleic acids that encode the antibodies of the present disclosure may be incorporated into a vector, preferably an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus vectors, preferably expression vectors, which find use in the present invention include but are not limited to those which enable protein expression in mammalian cells, bacteria, insect cells, yeast, and in in vitro systems. As is known in the art, a variety of expression vectors are available, commercially or otherwise, that may find use in the present disclosure for expressing antibodies. An example of a suitable expression vector is a pcDNA3.1 expression vector (Thermo Fisher Scientific).

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology, Methods in Enzymology 185, Academic Press, San Diego, Calif. (1990)). Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used. For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

In some aspects, the vector of the present disclosure comprises the nucleic acid sequence set forth in SEQ ID NO: 29. In some aspects, the vector comprises the nucleic acid sequence set forth in SEQ ID NO: 30. In some aspects, the vector comprises the nucleic acid sequence set forth in SEQ ID NO: 31. In some aspects, the vector comprises the nucleic acid sequence set forth in SEQ ID NO: 32.

Suitable host cells for cloning or expressing the DNA in the vectors herein are prokaryote, yeast, or higher eukaryote cells. Suitable prokaryotes for this purpose include eubacteria, including gram-negative or gram-positive organisms, for example, Enterobacteriaceae such as *Escherichia*, e.g., *E. coli, Enterobacter, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. Suitable *E. coli* cloning hosts include *E. coli* 294 (ATCC 31,446), *E. coli* B, *E. coli* X1776 (ATCC 31,537), and *E. coli* W3110 (ATCC 27,325).

In addition to prokaryotes, eukaryotic microbes such as filamentous fungi or yeast are suitable cloning or expression hosts. *Saccharomyces cerevisiae*, or common baker's yeast, is the most commonly used among lower eukaryotic host microorganisms. However, a number of other genera, species, and strains are commonly available and useful, such as *Schizosaccharoriyces pombe; Kluyveromyces* hosts including *K. lactis, K fragilis* (ATCC 12,424), K *bulgaricus* (ATCC 16,045), *K. wickeramii* (ATCC 24,178), K WaltH (AJCC 56,500), *K. drosopmarum* (ATCC 36,906), *K. thermotolerans*, or *K. marxianusyarrowia* (EP402226); *Pichia pastoris* (EP183070); *Candida; Trichoderma reesia* (EP244234); *Neurospora crassa; Schwanniomyces* such as *Schwanniomyces occidentalis*; and filamentous fungi including *Neurospora, Penicillium, Tolypocladium*, or *Aspergillus* hosts such as *A. nidulans* or *A. niger*.

Suitable host cells for the expression of the antibodies of the invention are derived from multicellular organisms. Examples of invertebrate cells include plaril and insect cells. Numerous baculoviral strains and variants and corresponding permissive insect host cells from hosts such as *Spodoptera frugiperda* (caterpillar), *Aedes augypti* (mosquito), *Aedes albopictus* (mosquito), *Drosophila melanogaster* (fruitfly) and *Bombyx mori* have been identified. A variety of viral strains for transfection are publicly available, for example, the L-1 variant of *Autographa californica* NPV and the Bm-5 strain of *Bombyx mori* NPV, and such viruses may be used, particularly for transfection of *Spodoptera frugiperda* cells. Plant cell cultures of cotton, corn, potato, soybean, *petunia*, tomato, and tobacco can also be utilized as hosts.

Host cells for expressing the recombinant antibodies of the invention also include mammalian host cells which include but are not limited to Chinese Hamster Ovary (CHO cells), NSO myeloma cells, COS cells and SP2 cells. When recombinant antibody genes are introduced into mammalian host cells, the antibodies are produced by culturing the host cells for a period of time sufficient to allow for expression of the antibody in the host cells or, more preferably, for secretion of the antibody into the culture medium in which the host cells are grown. Host cells useful for producing antibodies that bind AAVrh74 capsid protein may be cultured in a variety of media. Commercially available media such as Ham's F10 (Sigma-Aldrich Chemie GmbH, Buchs, Switzerland), Minimal Essential Medium (MEM; Sigma-Aldrich Chemie GmbH), RPMI-1640 (Sigma-Aldrich Chemie GmbH, Basel, Switzerland), and Dulbecco's Modified Eagle's Medium ((DMEM; Sigma-Aldrich Chemie GmbH) are suitable for culturing the host cells. Antibodies can be recovered from the culture medium using standard protein purification methods.

Antibodies may be operably linked to a fusion partner to enable targeting of the expressed protein, purification, screening, display, and the like. Fusion partners may be linked to the antibody sequence via a linker sequence. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence $G_4S$. A fusion partner may be a targeting or signal sequence that directs antibody and any associated fusion partners to a desired cellular location or to the extracellular media. As is known in the art, certain signalling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example H6 and H10 or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both.

Construction and Production of Antibodies

The present disclosure further provides a method of making an anti-AAV antibody or antigen binding fragment thereof. In some aspects, the methods of the present disclosure comprise using hybridoma technology to make the antibodies. Techniques for making hybridoma cells are well known to those of skill in the art. In some aspects, the disclosure provides a method of making the antibody comprising (a) administering to a non-human vertebrate animal an immunogenic amount of a polypeptide comprising the amino acid sequence QGAGKDNVDYSS (SEQ ID NO:

45); (b) recovering spleen cells from the animal; (c) fusing the recovered spleen cells with myeloma cells to generate hybridomas; (d) screening the hybridomas for hybridomas that produce an antibody that specifically binds AAVrh74 capsid protein; and (e) recovering the antibody. Administering polypeptides to an animal can be done using well-known and routine protocols, see for example Handbook of Experimental Immunology (Weir D M (ed.), Vol 4, Blackwell Scientific Publishers, Oxford, England, 1986).

In some embodiments, the non-human vertebrate animal is a transgenic animal, and wherein the transgenic animal expresses human immunoglobulin genes. In such aspects, the transgenic animal produces human antibodies directed to AAVrh74.

In some embodiments, the methods of the disclosure further comprise administering to the non-human vertebrate animal one or more immune adjuvants.

In some embodiments, the non-human vertebrate animal is selected from a mouse, rat, hamster, guinea pig, rabbit, chicken, non-human primate, pig, goat, cow, and horse. In a particular aspect, the non-human vertebrate animal is a mouse. In another particular aspect, the non-human vertebrate animal is a rat.

In some embodiments, the antibody or antigen binding fragment thereof specifically binds AAVrh74 capsid protein but does not bind AAV8 capsid protein and/or AAV9 capsid protein.

In some aspects, the hybridoma that expresses the antibody of the disclosure is a mouse hybridoma. In some aspects, the hybridoma is a hybridoma selected from the group consisting of 10D2-1, 28D8-1, 1C4F4, 6E10B5, and 7D4B9.

The present disclosure further provides a method of making an anti-AAV antibody or antigen binding fragment thereof using a phage display antibody library. Techniques for making antibodies using a phage display antibody library are well known to those of skill in the art. In some aspects of the disclosure, the methods comprise (a) immobilizing on a solid support an antigen comprising the amino acid sequence QGAGKDNVDYSS (SEQ ID NO: 45); (b) applying a phage display antibody library to the immobilized antigen; (c) screening the library for phage that bind the antigen; and (d) recovering antigen-binding phage.

Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some aspects, a suitable solid support is generally insoluble in an aqueous solution. In some embodiments, the solid support is selected from the group consisting of a microtiter plate well, polyvinylidene fluoride (PVDF) membrane, column matrix, immunotube, and magnetic bead.

In some embodiments, the phage display antibody library is derived from a non-human vertebrate animal previously immunized with a composition comprising an immunogen. In some aspects, the immunogen comprises an immunogenic amount of a polypeptide comprising the amino acid sequence QGAGKDNVDYSS (SEQ ID NO: 45).

In some embodiments, the non-human vertebrate animal is selected from a mouse, rat, hamster, guinea pig, rabbit, chicken, non-human primate, pig, goat, cow, and horse.

In some embodiments, the antibody or antigen binding fragment thereof specifically binds AAVrh74 capsid protein but does not bind AAV8 capsid protein and/or AAV9 capsid protein.

The present disclosure further provides an in silico method of making an anti-AAV antibody or antigen binding fragment thereof. In silico techniques for designing antibodies are known to those of skill in the art. In some aspects, the method comprises (a) designing CDRs in silico that specifically bind to an epitope on AAVrh74 capsid protein; (b) grafting the CDRs onto single-chain variable fragments (scFvs); (c) screening the scFvs for binding to a target polypeptide using antibody phage display; and (d) selecting scFvs that bind to the target polypeptide, wherein the epitope on AAVrh74 capsid protein and the target polypeptide each comprises the amino acid sequence QGAGKDNVDYSS (SEQ ID NO: 45).

In some embodiments, the antibody or antigen binding fragment thereof specifically binds AAVrh74 capsid protein but does not bind AAV8 capsid protein and/or AAV9 capsid protein.

Humanized antibodies of the present disclosure may be constructed by transferring one or more CDRs or portions thereof from VH and/or VL regions from a non-human animal (e.g., mouse) to one or more framework regions from human VH and/or VL regions. Optionally, human framework residues thus present in the VH and/or VL regions may be replaced by corresponding non-human (e.g., mouse) residues when needed or desired for decreasing immunogenicity of the antibody and/or maintaining binding affinity. Optionally, non-human amino acid residues present in the CDRs may be replaced with human residues. Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693, 762 and 6,180,370 to Queen et al).

The present invention provides a method of producing an antibody or fragment thereof that binds to AAVrh74 comprising culturing a host cell comprising an isolated nucleic acid encoding the antibody or fragment thereof that binds to AAVrh74 or a vector comprising an isolated nucleic acid encoding the antibody or fragment thereof that binds to AAVrh74 so that the nucleic acid is expressed and the antibody produced. Preferably the antibody is isolated. For host cells, nucleic acids and vectors, the ones described above can be used. Expression of the nucleic acids can be obtained by, e.g. a combination of recombinant DNA techniques and gene transfection methods as is well known in the art (e.g., Morrison S (1985) Science 229: 1202) and as further outlined above. For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into vectors such as expression vectors. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH1 segment(s) within the vector and the VK segment is operatively linked to the CK segment within the vector.

Purification of Anti-AAVrh74 Antibodies

Screening for antibodies can be performed using antibody binding assays known to those of skill in the art. Detailed methods for performing antibody screening assays are found in, e.g., Harlow and Lane (1988) Antibodies, A Laboratory Manual, Cold Spring Harbor Laboratory Press, Cold Spring Harbor, N.Y. Such assays can be used to measure antibody binding to AAVrh74 capsid protein. An example of a binding assay is an enzyme-linked immunosorbent assay (ELISA). In some aspects, the ELISA comprises a fusion protein of AAVrh74 capsid protein and human Fc, which is immobilized on a solid support, and employing a conjugated secondary antibody to detect anti-AAVrh74 antibody bound to the fusion protein. The antibodies of the present invention may be used as a positive control for the measurement of anti-AAVrh74 antibody in a sample (e.g., blood). In one embodiment, the ELISA is a direct ELISA, an indirect ELISA, a sandwich ELISA, a reverse ELISA, or a competitive ELISA. In one embodiment, the AAVrh74 antibody of this disclosure can be used in assays to detect pre-existing antibodies against AAVrh74, in serum or plasma from a subject; including mice, non-human primates, and a human. In one aspect, for any embodiment directed to detection of pre-existing antibodies, the pre-existing antibodies are contained in sera or plasma of such subject, that has been treated with an AAV-based gene therapy. In one embodiment, the gene therapy is an AAvrh74-based gene therapy. In another aspect of any embodiment directed to detection of pre-existing antibodies, the subject has not been treated with such gene therapy. The assays can be ELISA or Electro-ChemiLuminiescence Immunoassay (ECLIA). In such assays, AAVrh74 antibody serves as a positive control or a capture. The ELISA approach optionally utilizes either serum or plasma known to have antibodies against AAVrh74 as an optional positive control. The assays comprise binding the antibody found in test serum or plasma to the antigen (AAVrh74 capsid), followed by the detection of the antibodies using a substrate to quantify the antibody through an absorbance reading. The average optical density (OD) of wells receiving antigen is calculated against the OD of non-coated wells to determine the antibody endpoint titer. The ECLIA assay follows the same concept as the indirect ELISA and can identify samples with or without anti-rh74 antibodies, determine specificity of positive samples through competitive binding, and determine levels of antibody through titration methods.

Additionally, the anti-AAVrh74 antibody can be used to quantify capsid in gene therapy products through a sandwich ELISA where the AAVrh74 antibody is bound to the capture antibody, followed by the addition of a detector antibody, enzyme and substrate and quantified through an absorbance reading.

In one aspect, the disclosure provides a method of detecting a pre-existing antibody against AAV capsid in a sample from a subject, comprises subjecting the sample to an assay, wherein the antibody or antigen binding fragment thereof of any one of claims 1 to 30 is used as a positive control capture. In one embodiment, the assay is an immunoassay. In another embodiment, the assay is an immunofluorescence assay, an immunohistochemical assay, a Western blot, a direct enzyme-linked immunosorbent assay (ELISA), an indirect ELISA, a sandwich ELISA, a competitive ELISA, a reverse ELISA, a chemiluminescence assay, a radioimmunoassay, or an immunoprecipitation assay. In another embodiment, the assay is an ElectroChemiLuminiescence Immunoassay (ECLIA). In another embodiment, the method further comprises quantifying the pre-existing antibody through an absorbance reading.

Antibodies of the present invention may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. To purify AAVrh74 antibodies, selected host cells can be grown in e.g. spinner-flasks for monoclonal antibody purification. Supernatants can be filtered and concentrated before affinity chromatography with protein A-sepharose (Pharmacia, Piscataway, N.J.). Eluted antibodies can be checked by gel electrophoresis and high performance liquid chromatography to ensure purity. A preferred antibody of the present invention is thus an isolated and/or purified antibody that binds to AAVrh74 capsid protein.

Immunological Assays

The present disclosure also provides methods for detecting the presence of AAVrh74 capsid protein in a sample, comprising contacting the sample with a composition comprising the antibody or antigen binding fragment thereof as described herein. In some aspects, the sample is an environmental sample. In some aspects, the sample is a biological sample, including but not limited to, blood, e.g., whole blood, urine, saliva, plasma, lung washings, or lymph. In some embodiments, the presence of AAVrh74 capsid protein in the sample is indicated by detecting the presence of the antibody or antigen binding fragment thereof.

In some aspects of the disclosure, the presence of the antibody or antigen binding fragment thereof is detected by immunoassay. Suitable immunoassays for detecting the presence of the antibody or antigen binding fragment are known to those of skill in the art. Examples of suitable immunoassays include, but are not limited to, an immunofluorescence assay, an immunohistochemical assay, a Western blot, a direct enzyme-linked immunosorbent assay (ELISA), an indirect ELISA, a sandwich ELISA, a competitive ELISA, a chemiluminescence assay, a radioimmunoassay, and an immunoprecipitation assay. Methods for performing exemplary suitable immunoassays of the present disclosure are found in, e.g., Harlow and Lane (1988) Antibodies, A Laboratory Manual, Cold Spring Harbor Laboratory Press, Cold Spring Harbor, N.Y.

An immunofluorescence assay detects the expression and/or cellular location of a protein of interest. In a direct immunofluorescence assay, a primary detection antibody is coupled with a fluorophore. Labeled antibody bound to the protein of interest is then detected using fluorescent microscopy. In an indirect immunofluorescence assay, a secondary antibody is coupled to a fluorophore and specifically binds the primary antibody. The secondary antibody is then detected using fluorescent microscopy.

In some aspects, the anti-AAVrh74 antibodies disclosed herein comprise the primary antibody in an immunofluorescence assay to detect the presence of AAVrh74 capsid protein in a sample.

An immunohistochemical (IHC) assay detects the expression and/or cellular location of a protein of interest. In a direct immunohistochemical assay, a primary detection antibody coupled with an enzyme binds to the protein of interest. Detection is accomplished by assessing the presence of the conjugated enzyme via incubation with a substrate to produce a measurable product, such as color. In an indirect IHC assay, a secondary antibody is coupled to an enzyme and specifically binds the primary antibody. Detection of the secondary antibody is accomplished by assessing the presence of the conjugated enzyme via incubation with a substrate to produce a measurable product, such as color.

In some aspects, the anti-AAVrh74 antibodies disclosed herein comprise the primary antibody in an immunohistochemical assay to detect the presence of AAVrh74 capsid protein in a sample.

A Western blot is used to detect a specific protein or proteins in a sample. In a Western blot, a protein sample is treated with a detergent to unfold the proteins. The linear proteins are separated by size via gel electrophoresis (e.g., polyacrylamide gel electrophoresis, or PAGE) and then transferred to a blotting membrane (e.g., polyvinylidene difluoride—PVDF). The membrane is then incubated with a primary antibody that binds to the protein of interest. The primary antibody is then bound by a labeled secondary antibody. The labeled secondary antibody is linked to a reporter enzyme. Detection is accomplished by assessing the presence of the conjugated enzyme on the secondary antibody via incubation with a substrate to produce a measurable product, such as color or light.

In some aspects, the anti-AAVrh74 antibodies disclosed herein comprise the primary antibody of a Western blot to detect the presence of AAVrh74 capsid protein in a sample.

The pre-existing neutralizing antibody titers to AAV capsids and/or AAV serotypes and their cross-reactivity, or those induced by administration, have emerged as a concern and challenge for clinical applications of gene therapy and genetic vaccine mediated by AAV vectors. The pre-existing NAbs recognizing viral capsids could inhibit AAV entry and transgene delivery to the host cells, thereby preventing long-term therapy in humans. Determining the presence and cross-reactivity of neutralizing antibodies in a subject is critical for clinical applications of AAV vectors.

Therefore, in another aspect, the disclosure relates to a method of detecting the presence of an AAV antibody in a sample, comprising detecting the AAV antibody by an immunoassay, wherein the immunoassay uses a composition comprising the isolated antibody or antigen binding fragment thereof in this disclosure. In one embodiment, the AAV antibody is an AAVrh74 antibody. In one embodiment, the sample is a biological sample from a subject. In one embodiment, the sample is blood, serum, plasma, a body fluid, urine, or a tissue from a subject. In one embodiment, the subject is a mammal carrying a genetic disorder. In one embodiment, the mammal is human, pig, horse, cow, sheep, goat, monkey, rat, mouse, cat, or dog. In another embodiment, the subject is a patient. In another embodiment, the patient suffers from a heart disease, muscular dystrophy, an autoimmune disease, a metabolic disorder, diabetes, an ocular disease, and/or a renal disease. In another embodiment, the patient suffers from Duchenne muscular dystrophy (DMD) or Limb-girdle muscular dystrophy (LGMD). LGMDs refers to a group of LGMD forms classified by their associated genetic defects. Non-limiting examples of LGMDs include LGMD1A LGMD1B LGMD1C LGMD1D, LGMD1E, LGMD1F, LGMD1G, LGMD2A LGMD2B, LGMD2C, LGMD2D, LGMD2E, LGMD2F, LGMD2H, LGMD2I, LGMD2J, LGMD2K, and LGMD2L.

In another embodiment, the immunoassay comprises one or more of enzyme immunoassay (EIA), radioimmunoassay (MA), neutralization assay, fluoroimmunoassay (FIA) which uses fluorescent materials, chemiluminescent immunoassay (CLIA) which uses chemiluminescent materials and counting immunoassay (CIA) which employs particle-counting techniques, other modified assays such as western blot, immunohistochemistry (IHC) and agglutination. One of the most common enzyme immunoassays is enzyme-linked immunosorbent assay (ELISA). In one embodiment, the immunoassay comprises one or more of an immunofluorescence assay, an immunohistochemical assay, a Western blot, a direct enzyme-linked immunosorbent assay (ELISA), an indirect ELISA, a sandwich ELISA, a competitive ELISA, a reverse ELISA, an ECLIA, a chemiluminescence assay, a radioimmunoassay, or an immunoprecipitation assay.

The term "neutralization assay" and "serum virus neutralization assay" refers to a serological test to detect the presence of systemic antibodies that may prevent infectivity of a virus. Such assays may also qualitatively or quantitatively discern the binding capacity (e.g., magnitude) or efficiency of the antibodies to neutralize a target. The term "patient" includes human and other mammalian subjects that receive either prophylactic or therapeutic treatment. A neutralization assay is a specific immunoassay adapted for quantifying the titer of neutralizing antibody of a virus. In general, a test sample. e.g., serum sample and a solution of antibody, is diluted and mixed with a viral suspension. The mixture is added to a confluent monolayer of host cells after being incubated to allow the neutralizing antibody to react with the virus. The virus infectivity to the host cells is quantitated. The most common assay is called plaque reduction neutralization test (PRNT). In this assay, the concentration of plaque forming units is estimated by the number of plaques (regions of infected cells) formed in the culture after a period of incubation (typically a few days). Depending on the virus, the plaque forming units are measured by microscopic observation, fluorescent antibodies or specific dyes that react with infected cells. The concentration of serum to reduce the number of plaques by 50% compared to the serum free virus gives the measure of how much antibody is present or how effective it is. Virus neutralization assays are also widely used for detecting and measuring neutralizing antibodies to AAVs. Several assays have been proposed in the art to detect neutralizing antibodies to different AAV serotypes. Some of these methods detect total binding antibodies to AAV capsids and others detect antibodies that neutralize transduction of AAV vectors in vitro or in vivo. Early methods to evaluate total antibody responses to AAV vector included ELISA and Western blot (Blacklow et al., J Natl Cancer Inst, 1968, 40(2):319; Mayor et al., Am J Obstet Gynecol, 1976, 126(1):100; and Parks et al., Infect Immun, 1970; 2(6):716). ELISAs can detect the total amount of antibody in sera that bind to an AAV serotype, including non-neutralizing antibodies and neutralizing antibodies (Chirmule et al., Gene Ther., 1999, 6: 1574-1583); Erles et al., J Med. Virol., 1999, 59: 406-411; and Boutin et al., Hum. Gene Ther., 2010, 21: 704-712). Though ELISA-based assays are easy to set up and give a relatively sensitive measurement of total antibodies binding to AAV, the results do not necessarily reflect their neutralizing activity.

In another embodiment, the AAVrh74 antibody is a neutralizing antibody. In another aspect of any embodiment directed to detection of pre-existing antibodies, the subject has not been treated with such gene therapy. The assays can be ELISA or ElectroChemiLuminiescence Immunoassay (ECLIA). In such assays, AAVrh74 antibody serves as a positive control or a capture. The ELISA approach optionally utilizes either serum or plasma known to have antibodies against AAVrh74 as an optional positive control. The assays comprise binding the antibody found in test serum or plasma to the antigen (AAVrh74 capsid), followed by the detection of the antibodies using a substrate to quantify the antibody through an absorbance reading. The average optical density (OD) of wells receiving antigen is calculated against the OD of non-coated wells to determine the antibody endpoint titer. The ECLIA assay follows the same concept as the indirect ELISA and can identify samples with or without anti-rh74 antibodies, determine specificity of positive samples through competitive binding, and determine levels of antibody through titration methods.

ELISA is an assay designed for detecting and quantifying substances such as peptides, proteins, and antibodies. In an ELISA, an antigen is immobilized on a solid surface and then complexed with an antibody that is linked to an enzyme. Detection is accomplished by assessing the presence of the conjugated enzyme via incubation with a substrate to produce a measurable product, such as color. The detection enzyme can be linked directly to the primary antibody (direct ELISA) or introduced through a secondary antibody that recognizes the primary antibody (indirect ELISA).

In some aspects, the anti-AAV antibodies disclosed herein comprise the primary antibody in a direct or indirect ELISA to detect the presence of AAV capsid protein in a sample. In one embodiment, the anti-AAV antibody is an anti-AAVrh74 antibody. The AAV capsid protein is an AAVrh74 capsid protein.

A sandwich ELISA is an ELISA in which a capture antibody is first immobilized on a solid support, followed by addition of the protein of interest and the secondary antibody. In a sandwich ELISA, the protein of interest is bound between the capture antibody, which is immobilized on the solid surface, and the detection antibody, which binds the protein of interest.

In some aspects, the anti-AAVrh74 antibodies disclosed herein comprise the capture antibody or the detection antibody in a sandwich ELISA to detect the presence of AAVrh74 capsid protein in a sample.

A competitive ELISA, also known as an inhibition ELISA or a competitive immunoassay, measures the concentration of an antigen by detection of signal interference. The sample antigen competes with a reference antigen for binding to a specific amount of labeled antibody. The reference antigen is pre-coated on a multi-well plate. The sample is pre-incubated with labeled antibody and added to the wells. Depending on the amount of antigen in the sample, more or less free antibodies will be available to bind the reference antigen. Therefore, the more antigen there is in a sample, the less references antigen will be detected and the weaker the signal.

In some aspects, the anti-AAVrh74 antibodies disclosed herein comprise the labeled antibody in a competitive ELISA to detect the presence of AAVrh74 capsid protein in a sample.

A chemiluminescence assay utilizes a luminescent chemical as a substrate instead of a chromogen. Common enzymes which are conjugated to detection antibodies include, but are not limited to, horseradish peroxidase (HRP) and alkaline phosphatase (AP). Luminol is a common chemiluminescent substrate used for detection of HRP.

In some aspects, the anti-AAVrh74 antibodies as disclosed herein are conjugated to an enzyme that catalyzes a chemiluminescent reaction to detect the presence of AAVrh74 capsid protein in a sample.

In a radioimmunoassay, a known quantity of an antigen is radiolabeled and mixed with a known amount of antibody for that antigen. A sample containing an unknown amount of unlabeled antigen is then added. The unlabeled and radiolabeled antigen compete for antibody binding sites. As the concentration of unlabeled antigen increases, more of the radiolabeled antigen is displaced and the ration of antibody-bound radiolabeled antigen to free radiolabeled antigen is reduced. The bound radiolabeled antigens are then separated and the radioactivity of the free (unbound) radiolabeled antigen remaining in the supernatant is measured using a gamma counter.

In some aspects, the anti-AAVrh74 antibodies disclosed herein are used in a radioimmunoassay to detect the presence of AAVrh74 capsid protein in a sample.

An immunoprecipitation assay uses an antibody specific for a protein of interest to isolate that protein form a solution containing many different proteins, such as crude lysate of plant or animal cells or tissue, or bodily fluids. In a direct immunoprecipitation assay, antibodies specific for a protein of interest are immobilized on a solid phase substrate, such as superparamagnetic microbeads or microscopic agarose beads. The beads with bound antibody are then added to the solution and the protein of interest binds the antibody and is captured by the beads. The protein of interest is then eluted from the beads.

In an indirect immunoprecipitation assay, antibodies specific for a protein of interest are added directly to the solution. The antibodies have not yet been attached to a solid-phase support. Beads coated in protein A/G are then added to the mixture and the antibodies, which are now bound to the protein of interest, bind to the beads. The protein of interest is then eluted from the beads.

In some aspects, the anti-AAVrh74 antibodies as disclosed herein can be used to isolate AAVrh74 from a sample.

The immunoassays and methods described above are intended to be exemplary and non-limiting.

The methods of the present disclosure specifically detect the presence of AAVrh74 capsid protein in a sample. In some aspects of the disclosure, the method does not detect AAV8 capsid protein. In some aspects, the method does not detect AAV9 capsid protein. In some aspects, the method does not detect AAV8 and/or AAV9 capsid protein in the sample.

Kits

An embodiment of the present disclosure is directed to an in vitro detection kit comprising the antibody or antigen binding fragment thereof as described herein as an active agent and instructions for use. Kits of the present disclosure may include, but are not limited to, kits for use in an immunofluorescence assay, an immunohistochemical assay, a Western blot, a direct enzyme-linked immunosorbent assay (ELISA), an indirect ELISA, a sandwich ELISA, a reverse ELISA, a competitive ELISA, a chemiluminescence assay, a radioimmunoassay, and an immunoprecipitation assay. In some aspects, the kit can further contain a second antibody or antigen binding fragment thereof labeled with a radioactive, enzymatic or fluorescent group. In some aspects, the kit contains additional reagents, such as buffers, enzymes, and/or substrates, as well as a user manual for the kit.

In one embodiment, the disclosure provides a method for detecting the presence of an AAV antibody in a sample, comprising detecting the AAV antibody by an immunoassay, wherein the immunoassay uses a composition comprising the isolated antibody or antigen binding fragment thereof of the disclosure. In another embodiment, the immunoassay comprises enzyme immunoassay (EIA), radioimmunoassay (MA), fluoroimmunoassay (FIA), chemiluminescent immunoassay (CLIA) and counting immunoassay (CIA), neutralization assay, or immunohistochemistry (IHC). In another embodiment, the immunoassay comprises one or more of an immunofluorescence assay, an immunohistochemical assay, a Western blot, a direct enzyme-linked immunosorbent assay (ELISA), an indirect ELISA, a sandwich ELISA, a competitive ELISA, a reverse ELISA, an ECLIA, a chemiluminescence assay, a radioimmunoassay, or an immunoprecipitation assay. In another embodiment, the immunoassay is a neutralization assay. In another embodiment, the AAV antibody is an AAVrh74 antibody. In another embodiment, the AAV antibody is a neutralizing antibody. In another embodiment, the sample is a biological sample from a subject. In one embodiment, the subject is a mammal carrying a genetic disorder. In one embodiment, the mammal is human, pig, horse, cow, sheep, goat, monkey, rat, mouse, cat, or dog. In one embodiment, the subject is a human patient. In one embodiment, the patient suffers from a heart disease, muscular dystrophy, an autoimmune disease, a metabolic disorder, diabetes, an ocular disease, and/or a renal disease. In one embodiment, the patient suffers from Duchenne muscular dystrophy (DMD) or Limb-girdle muscular dystrophy (LGMD). In one embodiment, the composition comprising the isolated antibody or antigen binding fragment thereof of the disclosure serves as a positive control or a capture.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

Binding of Anti-AAVrh74 Antibodies to AAVrh74 Capsid Protein

Antibodies made according to the methods of the present disclosure were tested for their specific binding to AAVrh74.

An enzyme-linked immunosorbent assay was performed to measure the binding of antibody to AAVrh.74 capsid. Briefly, Immulon-4 HBX 96-well plates were coated with 100 µl of $2\times10^{10}$ vg/ml AAVrh.74, AAV8, and AAV9 viral stock in carbonate buffer (pH 9.4) per well. Plates were sealed and stored overnight at 4° C. Plates were blocked with 100 µl per well of a 5% nonfat dry milk and 1% normal goat serum in PBS for 1 hour at 37° C. The antibody stocks or samples were serially diluted (2-fold) in the blocking solution and 100 µl added in duplicate to both wells coated with AAV particles in carbonate buffer and wells coated with carbonate buffer alone. Non-Human Primate serum at 1:50 dilution was used the positive control for AAV8 and AAV9 while mouse anti-AAVrh74 serum was used positive control for mouse primary antibody. Plates were incubated at RT for 1 hour before and post incubation, wells were washed five times with 200 µl of PBS-T (0.05% Tween). Blocking solution was used again to dilute the secondary antibody, goat anti-mouse IgG-HRP at a 1:20,000 dilution. Wells received 100 µl of the secondary antibody and were incubated at RT for 30 minutes before being washed five times and blotted dry. Tetramethybenzidine substrate (100 µl/well) was added and incubated at RT for 2-3 minutes in the dark, before the addition of 100 µl of 1 N $H_2SO_4$ to stop the reaction. The absorbance at 450 nm was measured using the ELISA plate reader. The absorbance data for anti-AAVrh74 antibodies is shown in FIG. 1. and FIG. 2.

Figure 1:
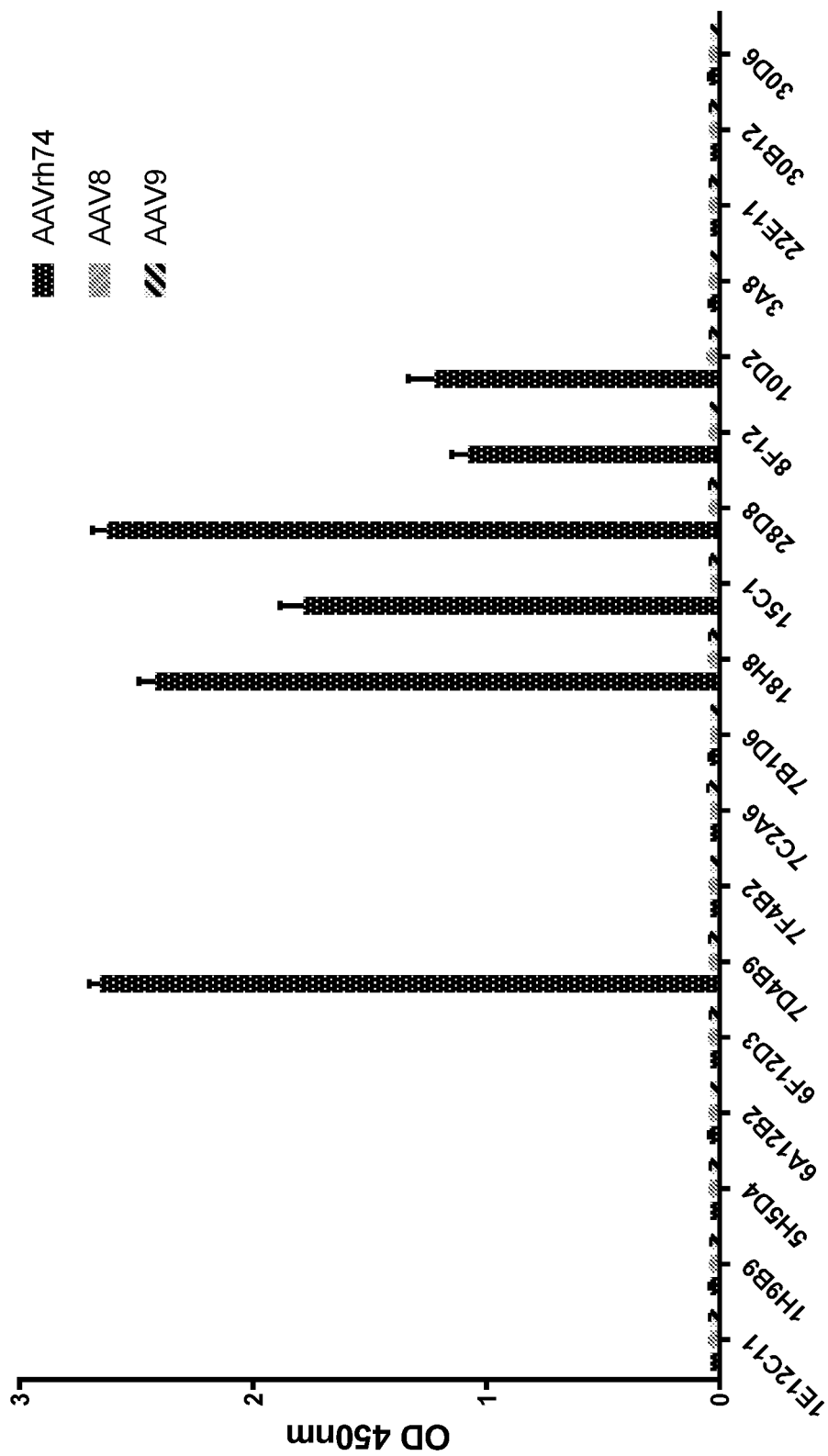
FIG. 1 shows ELISA data for screening antibodies that bind AAVrh74.
Figure 2:
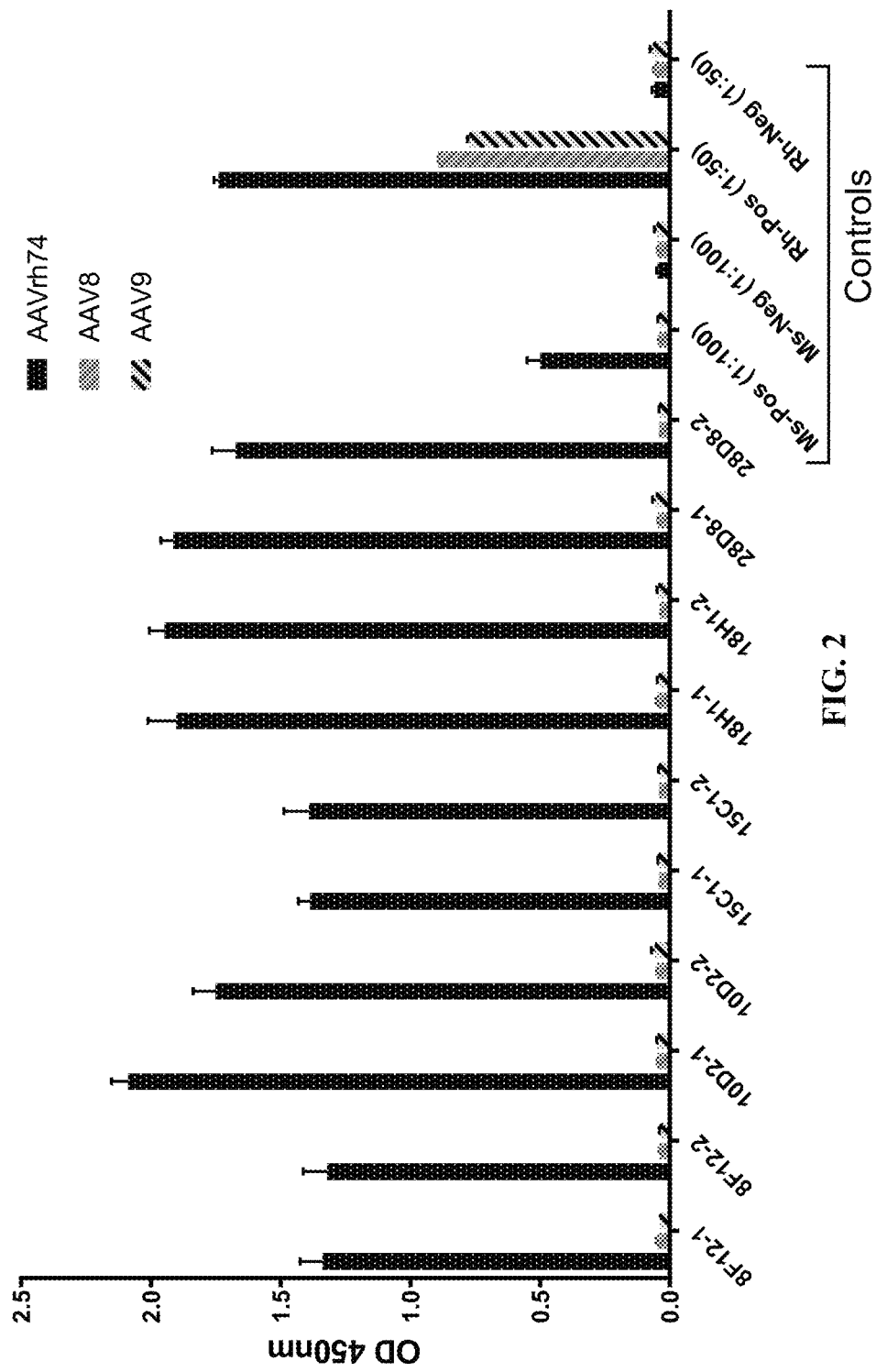
FIG. 2 shows ELISA data for screening antibodies that bind AAVrh74 but with less, limited or no binding to AAV8 and/or AAV9.

FIG. 1 shows the screening of antibodies for binding to AAVrh74. FIG. 2 shows testing antibodies for those that specifically bind to AAVrh74 with a much higher affinity as compared to either AAV8 or AAV9. The results show serotype specific binding to AAVrh74 with little or no cross-reactivity with AAV8 and/or AAV9.

Example 2

Binding of Chimeric Anti-AAVrh74 Antibodies to AAVrh74 Capsid Protein

An enzyme-linked immunosorbent assay was performed as above to measure the binding of chimeric antibodies to AAVrh74 capsid at different antibody concentrations.

FIGS. 3A-3C show the titration curves of the chimeric IgG1 10D2 and chimeric IgG1 28D8. Binding of the chimeric antibodies to AAVrh74 was compared to background signal at various antibody concentrations. FIG. 3A shows the titration curve for the chimeric IgG1 10D2 antibody, with an endpoint titer of 1:1638400. FIG. 3B shows the titration curve of chimeric IgG1 28D8 antibody, with an endpoint titer of 1:638400. FIG. 3C shows an overlay of the curves for chimeric IgG1 10D2 and chimeric IgG1 28D8.

The cross-reactivities for chimeric IgG1 10D2 (FIGS. 4A-4D) and chimeric IgG1 28D8 (FIGS. 5A-5D) were tested at different antibody concentrations. FIGS. 4A-4C show that chimeric IgG1 10D2 specifically binds to AAVrh74 (FIG. 4A) with a much higher affinity as compared to either AAV8 (FIG. 4B) or AAV9 (FIG. 4C). Positive and negative controls are shown in FIG. 4D. The results show serotype specific binding to AAVrh74 with little or no cross-reactivity with AAV8 and/or AAV9. FIGS. 5A-5D show that chimeric IgG1 28D8 specifically binds to AAVrh74 (FIG. 5A) with a much higher affinity as compared to either AAV8 (FIG. 5B) or AAV9 (FIG. 5C). Positive and negative controls are shown in FIG. 5D. The results show serotype specific binding to AAVrh74 with little or no cross-reactivity with AAV8 and/or AAV9.

FIGS. 6A-6C shows the titration curves of the chimeric IgA 10D2 and chimeric IgA 28D8. Binding of the chimeric antibodies to AAVrh74 was compared to background signal at various antibody concentrations. FIG. 6A shows the titration curve for chimeric IgA 10D2, with an end-point titer of 1:409600. FIG. 6B shows the titration curve for chimeric IgA 28D8, with an end-point-titer of 1:819200. FIG. 6C shows an overlay of the titration curves for chimeric IgA 10D2 and chimeric IgA 28D8.

The cross-reactivities for chimeric IgA 10D2 (FIGS. 7A-7D) and chimeric IgA 28D8 (FIGS. 8A-8D) were tested at different antibody concentrations. FIGS. 7A-7C show that chimeric IgA 10D2 specifically binds to AAVrh74 (FIG. 7A) with a much higher affinity as compared to either AAV8 (FIG. 7B) or AAV9 (FIG. 7C). Positive and negative controls are shown in FIG. 7D. The results show serotype specific binding to AAVrh74 with little or no cross-reactivity with AAV8 and/or AAV9. FIGS. 8A-8C show that chimeric IgA 28D8 specifically binds to AAVrh74 (FIG. 8A) with a much higher affinity as compared to either AAV8 (FIG. 8B) or AAV9 (FIG. 8C). Positive and negative controls are shown in FIG. 8D. The results show serotype specific binding to AAVrh74 with little or no cross-reactivity with AAV8 and/or AAV9.

The cross-reactivities for monoclonal antibodies 7D4B9 (FIG. 9A), 1C4F4 (FIG. 9B), and 6E10B5 (FIG. 9C) were tested at different antibody concentrations. An enzyme-linked immunosorbent assay was performed to measure the binding of antibody to AAVrh.74 capsid. Briefly, Immulon-4 HBX 96-well plates were coated with 100 µl of 2×10$^{10}$ vg/ml AAVrh.74, AAV8, and AAV9 viral stock in carbonate buffer (pH 9.4) per well. Plates were sealed and stored overnight at 4° C. Plates were blocked with 100 µl per well of a 5% nonfat dry milk and 1% normal goat serum in PBS for 1 hour at 37° C. The antibody stocks or samples were serially diluted (10-fold) in the blocking solution and 100 µl added in duplicate to both wells coated with AAV particles in carbonate buffer and wells coated with carbonate buffer alone. Non-Human Primate serum at 1:50 dilution was used the positive control for AAV8 and AAV9 while mouse anti-AAVrh74 serum was used positive control for mouse primary antibody. Plates were incubated at RT for 1 hour before and post incubation, wells were washed five times with 200 µl of PBS-T (0.05% Tween). Blocking solution was used again to dilute the secondary antibody, goat anti-mouse IgG-HRP at a 1:10,000 dilution. Wells received 100 µl of the secondary antibody and were incubated at RT for 30 minutes before being washed five times and blotted dry. Tetramethybenzidine substrate (100 µl/well) was added and incubated at RT for 2-3 minutes in the dark, before the addition of 100 µl of 1 NH$_2$SO$_4$ to stop the reaction. The absorbance at 450 nm was measured using the ELISA plate reader.

FIGS. 9A-9C show that all three monoclonal antibodies (7D4B9, 1C4F4, 6E10B5) specifically bound to AAVrh74 with a higher affinity as compared to either AAV8 or AAV9. Positive and negative controls are shown in FIG. 9D. FIG. 9E shows an overlay of the titration curves for 7D4B9, 1C4F4, and 6E10B5. All three antibodies show serotype specific binding to AAVrh74 with comparably less cross-reactivities with AAV8 and/or AAV9.

Example 3

Sandwich ELISA: Determination of Antibodies in Sera

Materials
Capture Antibody=Inventive anti-AAVrh74 mAb
Test sample=serum or plasma, will serve in detection
Antigen=AAVrh74 capsid
Blocking Solution=5% dry milk, 1% goat serum, 100 mL PBS
Wash Buffer=0.05% PBS-Tween
Positive Control=serum known to have anti-AAVrh74 antibodies
Secondary Antibody=anti-human-HRP conjugated antibody
Substrate=TMB
Stop Solution=Sulfuric Acid Method All wells of a 96-well plate are coated overnight with the capture antibody diluted in carbonate buffer at 4 C. The content is discarded, and the plate is blocked with the blocking solution for 1 h at 37 C. Blocking solution is discarded to add AAVrh74 capsid in duplicate on to the capture antibody coated wells. Additionally, carbonate buffer is added to duplicate wells to determine background value. Unbound capsid is discarded and the test serum is added at a starting dilution of 1:25 in blocking solution and serially diluted. Positive control is diluted in blocking solution at a 1:400 dilution. Plate is washed with wash buffer, followed by secondary incubation at a dilution of 1:10,000 in blocking solution. Plate is washed and buffer is discarded, and substrate is added followed by concluding the assay with sulfuric acid. The plate absorbance is read at 450 nm.

Analysis and Results

Absorbance ratio is determined by subtracting the average optical density (OD) of the non-antigen coated wells from the average OD of the antigen coated wells and dividing by the average (OD) of the non-antigen coated wells. A ratio of ≥2.00 is considered a positive antibody response. The end-point titer is determined by identifying the last serum dilution yielding a ratio of ≥2.00. The antibody cutoff is defined at a serum dilution of >1:400.

Example 4

Sandwich ELISA: Determination of Vector Present in a Sample OR Vector Enumeration Materials
Capture Ab: ADK8 clone
Test sample or antigen: anti-AAVrh74 containing samples
Blocking solution: 5% dry milk, 1% goat serum or BSA, 100 mL PBS
Wash Buffer=0.05% PBS-Tween
Detector Antibody: Inventive anti-AAVrh74 mAb (Biotin-conjugated)
Secondary Ab: HRP-conjugated Streptavidin
Substrate: TMB
Stop solution: Sulfuric acid Method The wells of 96-well plate are coated with a desired amount of diluted capture antibody in carbonate buffer at 4 C. AAVrh74 capsid standard and test samples are diluted serially in assay buffer and added in duplicates into the corresponding wells coated with capture antibody. Plates is incubated for 1 h at 37° C. Plate is washed before adding diluted 28D8-biotin antibody (inventive mAb) to all designated wells and incubated for 1 h. Plate is washed, followed by secondary incubation of diluted Strep-HRP (1:5000-1:10000) for 1 h. After washing the plates, ready-to-use TMB into each well and incubated for 10-15 min at RT. The reaction is stopped by adding sulfuric acid into each well and color intensity is measured with a photometer at a wavelength of 450 nm.

Analysis and Result

The amount of capsid present in any given samples will be extrapolated using the OD at 450 and 4-parameter logistic curve (4PL) equation obtained from the standard curve.

Example 5 ElectroChemiLuminiescence Immunoassay (ECLIA) ELISA: Determination of Antibodies in Sera Materials Capture reagent=AAVrh74 capsid or Virus-like particles Detection antibody=sulfo-TAG labeled anti-human IgG antibody Test sample=serum or plasma Positive control=Inventive AAVrh74 mAb Blocking Solution=5% dry milk, 1% goat serum or BSA, 100 mL PBS Wash Buffer=0.05% PBS-Tween Read Buffer=MSD Buffer or equivalent Signal reactor=Tripropylamine or equivalent Method/Principle:

ECL ELISA use electrochemiluminescent labels that are conjugated to detection antibodies. The labels are called SULFO-TAG and allow for ultra-sensitive detection. Electricity is applied to the plate electrodes by an special instrument leading to light emission by SULFO-TAG labels. Light intensity is then measured to quantify analytes in the sample.

Wells are coated with the capture reagent (AAVrh74 capsid) overnight at 4 C. Non-specific binding to the plate is blocked by adding blocking buffer for one hour. Blocking is discarded, followed by addition of diluted test sera, negative, and control samples to the designated wells. Diluted anti-AAVrh74 inventive mAb is used as a positive control. Wells are washed to add detector antibody (diluted anti-human IgG sulfo-TAG). Plate is washed with wash buffer followed by addition of read buffer to each well. After adding read buffer, plate is read or scanned immediately.

Analysis and Results

An electrical current is used to determine the presence of the signal reactor. The signal is relative to the amount of antibody within the serum.

Surface Plasmon Resonance

Introduction/Principle:

Surface plasmon resonance (SPR) is a label-free detection method and a reliable platform in clinical analysis for biomolecular interactions. The technique makes it possible to measure interactions in real-time with high sensitivity and without the need of labels. Surface plasmon resonance occurs when a photon of incident light hits a metal surface (gold surface). At a certain angle of incidence, a portion of the light energy couples through the metal coating with the electrons in the metal surface layer, which then move due to excitation. The electron movements are now called plasmon, and they propagate parallel to the metal surface. The plasmon oscillation in turn generates an electric field from the boundary between the metal surface and sample solution. The defined SPR angle, at which resonance occurs, on the conditions of the constant light source wavelength and metal thin surface, is dependent on the refractive index of the material near the metal surface. Consequently, when there is a small change in the reflective index of the sensing medium (e.g., through biomolecule attachment), plasmon cannot be formed. Detection is thus accomplished by measuring the changes in the reflected light obtained on a detector. In addition, the amount of surface concentration can be quantified by monitoring the reflected light intensity or tracking the resonance angle shifts. Typically, an SPR biosensor has a detection limit on the order of 10 pg/mL.

Basic Method:

Surface plasma resonance is carried out using instrument such as BIAcore™ T200 using HEPES buffer. The inventive mAb is mixed with desired concentration of AAVrh74 and immobilized on a sensor chip by amide coupling. The test analyte (serum sample) are flow through the chip and different dilutions. The change in the refractive index due to binding of AAVrh74-specific antibody present in the serum sample to immobilized AAV will be recorded. The data and graph will be generated using BIAcore software. Standard curve can be generated and the amount of antibody present in the serum can be extrapolated using the graph equation.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

What is claimed is:

1. An isolated antibody or antigen-binding fragment thereof that comprises a heavy chain variable region comprising VH CDR1, VH CDR2, and VH CDR3 domains, and a light chain variable region comprising VL CDR1, VL CDR2, and VL CDR3 domains, wherein:
   a. the VH CDR1 domain comprises an amino acid sequence selected from the group consisting of SEQ ID NO: 33, SEQ ID NO: 39, SEQ ID NO: 46, SEQ ID NO: 52, and SEQ ID NO: 58;
   b. the VH CDR2 domain comprises an amino acid sequence selected from the group consisting of SEQ ID NO: 34, SEQ ID NO: 40, SEQ ID NO: 47, SEQ ID NO: 53, and SEQ ID NO: 59;
   c. the VH CDR3 domain comprises an amino acid sequence selected from the group consisting of SEQ ID NO: 35, SEQ ID NO: 41, SEQ ID NO: 48, SEQ ID NO: 54, and SEQ ID NO: 60;
   d. the VL CDR1 domain comprises an amino acid sequence selected from the group consisting of SEQ ID NO: 36, SEQ ID NO: 42, SEQ ID NO: 49, SEQ ID NO: 55, and SEQ ID NO: 61;
   e. the VL CDR2 domain comprises an amino acid sequence selected from the group consisting of SEQ ID NO: 37, SEQ ID NO: 43, SEQ ID NO: 50, SEQ ID NO: 56, and SEQ ID NO: 62; and
   f. the VL CDR3 domain comprises an amino acid sequence selected from the group consisting of SEQ ID NO: 38, SEQ ID NO: 44, SEQ ID NO: 51, SEQ ID NO: 57, and SEQ ID NO: 63.

2. The isolated antibody or antigen-binding fragment thereof of claim 1, wherein the antibody comprises a heavy chain variable region that comprises VH CDR1, VH CDR2, and VH CDR3 domains, and a light chain variable region that comprises VL CDR1, VL CDR2, and VL CDR3 domains selected from the group consisting of:
   a. a VH CDR1 having the amino acid sequence set forth in SEQ ID NO: 33, a VH CDR2 having the amino acid sequence set forth in SEQ ID NO: 34, a VH CDR3 having the amino acid sequence set forth in SEQ ID NO: 35, a VL CDR1 having the amino acid sequence set forth in SEQ ID NO: 36, a VL CDR2 having the amino acid sequence set forth in SEQ ID NO: 37, and a VL CDR3 having the amino acid sequence set forth in SEQ ID NO: 38;
   b. a VH CDR1 having the amino acid sequence set forth in SEQ ID NO: 39, a VH CDR2 having the amino acid sequence set forth in SEQ ID NO: 40, a VH CDR3 having the amino acid sequence set forth in SEQ ID NO: 41, a VL CDR1 having the amino acid sequence set forth in SEQ ID NO: 42, a VL CDR2 having the amino acid sequence set forth in SEQ ID NO: 43, and a VL CDR3 having the amino acid sequence set forth in SEQ ID NO: 44;
   c. a VH CDR1 having the amino acid sequence set forth in SEQ ID NO: 46, a VH CDR2 having the amino acid sequence set forth in SEQ ID NO: 47, a VH CDR3 having the amino acid sequence set forth in SEQ ID NO: 48, a VL CDR1 having the amino acid sequence set forth in SEQ ID NO: 49, a VL CDR2 having the amino acid sequence set forth in SEQ ID NO: 50, and a VL CDR3 having the amino acid sequence set forth in SEQ ID NO: 51;
   d. a VH CDR1 having the amino acid sequence set forth in SEQ ID NO: 52, a VH CDR2 having the amino acid sequence set forth in SEQ ID NO: 53, a VH CDR3 having the amino acid sequence set forth in SEQ ID NO: 54, a VL CDR1 having the amino acid sequence set forth in SEQ ID NO: 55 a VL CDR2 having the amino acid sequence set forth in SEQ ID NO: 56, and a VL CDR3 having the amino acid sequence set forth in SEQ ID NO: 57; and
   e. a VH CDR1 having the amino acid sequence set forth in SEQ ID NO: 58, a VH CDR2 having the amino acid sequence set forth in SEQ ID NO: 59, a VH CDR3 having the amino acid sequence set forth in SEQ ID NO: 60, a VL CDR1 having the amino acid sequence set forth in SEQ ID NO: 61, a VL CDR2 having the amino acid sequence set forth in SEQ ID NO: 62, and a VL CDR3 having the amino acid sequence set forth in SEQ ID NO: 63.

3. The isolated antibody or antigen-binding fragment thereof of claim 1, wherein the heavy chain variable region of the antibody or antigen binding fragment thereof is selected from the group consisting of SEQ ID NO: 1, SEQ ID NO: 5, SEQ ID NO: 13, SEQ ID NO: 9, and SEQ ID NO: 17.

4. The isolated antibody or antigen-binding fragment thereof of claim 3, wherein the light chain variable region of the antibody or antigen binding fragment thereof is selected from the group consisting of SEQ ID NO: 2, SEQ ID NO: 6, SEQ ID NO: 14, SEQ ID NO: 10, and SEQ ID NO: 18.

5. The isolated antibody or antigen-binding fragment thereof of claim 4, wherein
   a. the heavy chain variable region comprises an amino acid sequence selected from the group consisting of SEQ ID NO: 1, SEQ ID NO: 5, SEQ ID NO: 13, SEQ ID NO: 9, and SEQ ID NO: 17; and b. the light chain variable region comprises an amino acid sequence selected from the group consisting of SEQ ID NO: 2, SEQ ID NO: 6, SEQ ID NO: 14, SEQ ID NO: 10, and SEQ ID NO: 18.

6. The isolated antibody or antigen-binding fragment thereof of claim 5, comprising a heavy chain variable region comprising the amino acid sequence set forth in SEQ ID NO: 1 and a light chain variable region comprising the amino acid sequence set forth in SEQ ID NO: 2.

7. The isolated antibody or antigen-binding fragment thereof of claim 5, comprising a heavy chain variable region comprising the amino acid sequence set forth in SEQ ID NO: 5 and a light chain variable region comprising the amino acid sequence set forth in SEQ ID NO: 6.

8. The isolated antibody or antigen-binding fragment thereof of claim 5, comprising a heavy chain variable region comprising the amino acid sequence set forth in SEQ ID NO: 13 and a light chain variable region comprising the amino acid sequence set forth in SEQ ID NO: 14.

9. The isolated antibody or antigen-binding fragment thereof of 5, comprising a heavy chain variable region comprising the amino acid sequence set forth in SEQ ID NO: 9 and a light chain variable region comprising the amino acid sequence set forth in SEQ ID NO: 10.

10. The isolated antibody or antigen-binding fragment thereof of claim 5, comprising a heavy chain variable region comprising the amino acid sequence set forth in SEQ ID NO: 17 and a light chain variable region comprising the amino acid sequence set forth in SEQ ID NO: 18.

11. The isolated antibody or antigen-binding fragment thereof of claim 1, wherein the antibody or binding fragment thereof binds to a capsid protein of AAV8 and/or AAV9 with less affinity as compared to a capsid protein of AAVrh74.

12. The isolated antibody or antigen-binding fragment thereof of claim 1, wherein the antibody or antigen binding fragment thereof is labeled with a radioactive, enzymatic, or fluorescent group.

13. The isolated antibody or antigen-binding fragment thereof of claim 1, wherein the antibody is a full-length antibody or an antibody fragment selected from the group consisting of Fab, Fab', Fab'-SH, Fd, Fv, dAb, F(ab')2, scFv, bispecific single-chain Fv dimers, diabodies, triabodies, and sxFv genetically fused to the same or a different antibody.

14. The isolated antibody or antigen-binding fragment thereof of claim 1, wherein the antibody is a murine antibody, a chimeric murine/human antibody, a human antibody, an engineered antibody, or a humanized antibody.

15. The isolated antibody or antigen-binding fragment thereof of claim 1, wherein the antibody or antigen binding fragment thereof is a bispecific antibody.

16. The isolated antibody or antigen-binding fragment thereof of claim 1, wherein the antibody or antigen binding fragment thereof is a multispecific antibody.

17. A polynucleotide comprising a nucleic acid sequence that encodes the isolated antibody or antigen-binding fragment thereof of claim 1, wherein the isolated antibody or antigen-binding fragment thereof comprises:
  a. a VH CDR1 domain comprising an amino acid sequence selected from the group consisting of SEQ ID NO: 33, SEQ ID NO: 39, SEQ ID NO: 46, SEQ ID NO: 52, and SEQ ID NO: 58;
  b. a VH CDR2 domain comprising an amino acid sequence selected from the group consisting of SEQ ID NO: 34, SEQ ID NO: 40, SEQ ID NO: 47, SEQ ID NO: 53, and SEQ ID NO: 59;
  c. a VH CDR3 domain comprising an amino acid sequence selected from the group consisting of SEQ ID NO: 35, SEQ ID NO: 41, SEQ ID NO: 48, SEQ ID NO: 54, and SEQ ID NO: 60;
  d. a VL CDR1 domain comprising an amino acid sequence selected from the group consisting of SEQ ID NO: 36, SEQ ID NO: 42, SEQ ID NO: 49, SEQ ID NO: 55, and SEQ ID NO: 61;
  e. a VL CDR2 domain comprising an amino acid sequence selected from the group consisting of SEQ ID NO: 37, SEQ ID NO: 43, SEQ ID NO: 50, SEQ ID NO: 56, and SEQ ID NO: 62; and
  f. a VL CDR3 domain comprising an amino acid sequence selected from the group consisting of SEQ ID NO: 38, SEQ ID NO: 44, SEQ ID NO: 51, SEQ ID NO: 57, and SEQ ID NO: 63.

18. The polynucleotide of claim 17, wherein the polynucleotide comprises a nucleic acid sequence that encodes:
  a. a VH CDR1 having the amino acid sequence set forth in SEQ ID NO: 33, a VH CDR2 having the amino acid sequence set forth in SEQ ID NO: 34, a VH CDR3 having the amino acid sequence set forth in SEQ ID NO: 35, a VL CDR1 having the amino acid sequence set forth in SEQ ID NO: 36, a VL CDR2 having the amino acid sequence set forth in SEQ ID NO: 37, and a VL CDR3 having the amino acid sequence set forth in SEQ ID NO: 38;
  b. a VH CDR1 having the amino acid sequence set forth in SEQ ID NO: 39, a VH CDR2 having the amino acid sequence set forth in SEQ ID NO: 40, a VH CDR3 having the amino acid sequence set forth in SEQ ID NO: 41, a VL CDR1 having the amino acid sequence set forth in SEQ ID NO: 42, a VL CDR2 having the amino acid sequence set forth in SEQ ID NO: 43, and a VL CDR3 having the amino acid sequence set forth in SEQ ID NO: 44;
  c. a VH CDR1 having the amino acid sequence set forth in SEQ ID NO: 46, a VH CDR2 having the amino acid sequence set forth in SEQ ID NO: 47, a VH CDR3 having the amino acid sequence set forth in SEQ ID NO: 48, a VL CDR1 having the amino acid sequence set forth in SEQ ID NO: 49, a VL CDR2 having the amino acid sequence set forth in SEQ ID NO: 50, and a VL CDR3 having the amino acid sequence set forth in SEQ ID NO: 51;
  d. a VH CDR1 having the amino acid sequence set forth in SEQ ID NO: 52, a VH CDR2 having the amino acid sequence set forth in SEQ ID NO: 53, a VH CDR3 having the amino acid sequence set forth in SEQ ID NO: 54, a VL CDR1 having the amino acid sequence set forth in SEQ ID NO: 55 a VL CDR2 having the amino acid sequence set forth in SEQ ID NO: 56, and a VL CDR3 having the amino acid sequence set forth in SEQ ID NO: 57; or
  e. a VH CDR1 having the amino acid sequence set forth in SEQ ID NO: 58, a VH CDR2 having the amino acid sequence set forth in SEQ ID NO: 59, a VH CDR3 having the amino acid sequence set forth in SEQ ID NO: 60, a VL CDR1 having the amino acid sequence set forth in SEQ ID NO: 61, a VL CDR2 having the amino acid sequence set forth in SEQ ID NO: 62, and a VL CDR3 having the amino acid sequence set forth in SEQ ID NO: 63.

19. The polynucleotide of claim 17, wherein the polynucleotide comprises a nucleic acid sequence that encodes a heavy chain variable region and a nucleic acid sequence that encodes a light chain variable region, wherein:

a. the nucleic acid encoding the heavy chain variable region comprises a nucleotide sequence selected from the group consisting of SEQ ID NO: 3; SEQ ID NO: 7; SEQ ID NO: 15; SEQ ID NO: 11; and SEQ ID NO: 19; and
b. the nucleic acid encoding the light chain variable region comprises a nucleotide sequence selected from the group consisting of SEQ ID NO: 4; SEQ ID NO: 8; SEQ ID NO: 16; SEQ ID NO: 12; and SEQ ID NO: 20.

* * * * *

UNITED STATES PATENT AND TRADEMARK OFFICE
CERTIFICATE OF CORRECTION

PATENT NO. : 11,472,866 B2
APPLICATION NO. : 17/478645
DATED : October 18, 2022
INVENTOR(S) : Sohrab Khan, Danielle Griffin and Louise Rodino-Klapac It is certified that error appears in the above-identified patent and that said Letters Patent is hereby corrected as shown below:

In the Specification

In Column 29, Table 4, delete:
"AAGTGTAAGTTACATGCACTGGTTCCAGCAGAAGCCAGGCACTTCTCCCAAACTCTGGATTTATAGCACATCCAACCTGGCTTCTGGAGTCCCTGCTCGCTTCAGTGGCAGTGGATCTGGGACCTCTTACTCTCTCACAATCAGCCGAATGGAGGCTGAAGATGCAGCCACTTATTACTGCCAGCAAAGGAGTTTTTACCCATTCACGTTCGGCTCGGGGACAAAGTTGGAAATAAAACGG
(SEQ ID NO: 12)"

And insert:
--CAAATTGTTCTCACCCAGTCTCCAGCAATCATGTCTGCATCTCCAGGGGAGAAGGTCACCATAACCTGCAGTGCCAGCTCAAGTGTAAGTTACATGCACTGGTTCCAGCAGAAGCCAGGCACTTCTCCCAAACTCTGGATTTATAGCACATCCAACCTGGCTTCTGGAGTCCCTGCTCGCTTCAGTGGCAGTGGATCTGGGACCTCTTACTCTCTCACAATCAGCCGAATGGAGGCTGAAGATGCAGCCACTTATTACTGCCAGCAAAGGAGTTTTTACCCATTCACGTTCGGCTCGGGGACAAAGTTGGAAATAAAACGG
(SEQ ID NO: 12)--, therefor.

Signed and Sealed this
Twenty-first Day of February, 2023

Katherine Kelly Vidal
*Director of the United States Patent and Trademark Office*